(12) United States Patent
Miyazaki

(10) Patent No.: US 8,158,829 B2
(45) Date of Patent: *Apr. 17, 2012

(54) ORGANIC SULFUR COMPOUND AND ITS USE FOR CONTROLLING HARMFUL ARTHROPOD

(75) Inventor: Hiroyuki Miyazaki, Takarazuka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/600,622

(22) PCT Filed: May 16, 2008

(86) PCT No.: PCT/JP2008/059492

§ 371 (c)(1),
(2), (4) Date: Nov. 17, 2009

(87) PCT Pub. No.: WO2008/143333

PCT Pub. Date: Nov. 27, 2008

(65) Prior Publication Data

US 2010/0152289 A1 Jun. 17, 2010

(30) Foreign Application Priority Data

May 18, 2007 (JP) ................................. 2007-132611

(51) Int. Cl.
*C07C 233/00* (2006.01)
*A61K 31/16* (2006.01)

(52) U.S. Cl. ....................................... 564/209; 514/628

(58) Field of Classification Search .................... None
See application file for complete search history.

(56) References Cited

U.S. PATENT DOCUMENTS

| 3,513,172 A | 5/1970 | Brokke et al. |
| 3,654,293 A | 4/1972 | Brokke |
| 3,666,818 A | 5/1972 | Brokke |
| 3,692,912 A | 9/1972 | Brokke |
| 3,697,536 A | 10/1972 | Brokke |
| 3,700,646 A | 10/1972 | Anello et al. |
| 3,780,050 A | 12/1973 | Brokke et al. |
| 3,891,662 A | 6/1975 | Brokke |
| 5,807,899 A | 9/1998 | Bohlmann et al. |
| 6,288,051 B1 | 9/2001 | Bittler et al. |
| 2003/0229050 A1 | 12/2003 | Lahm et al. |
| 2010/0160434 A1* | 6/2010 | Miyazaki ...................... 514/550 |

FOREIGN PATENT DOCUMENTS

| EP | 0134200 A1 | 3/1985 |
| FR | 2516920 A1 * | 5/1983 |
| FR | 2 619 811 A1 | 3/1989 |
| JP | 2004-91785 A | 3/2004 |
| JP | 2004-130306 A | 4/2004 |
| JP | 2005-179321 A | 7/2005 |
| WO | WO 98/07740 A1 | 2/1998 |
| WO | WO 98/25916 A1 | 6/1998 |
| WO | WO 99/33855 A1 | 7/1999 |
| WO | WO 99/42109 A1 | 8/1999 |
| WO | WO 00/03979 A1 | 1/2000 |
| WO | WO 02/40431 A2 | 5/2002 |
| WO | WO 2007/060839 A1 | 5/2007 |

OTHER PUBLICATIONS

Patani et al Chem. Rev. (1996), 96, pp. 3147-3176.*
International Preliminary Report on Patentability and Written Opinion dated Nov. 24, 2009 for Application No. PCT/JP2008/059491.
International Preliminary Report on Patentability and Written Opinion dated Nov. 24, 2009 for Application No. PCT/JP2008/059492.
International Preliminary Report on Patentability and Written Opinion dated Nov. 24, 2009 for Application No. PCT/JP2008/059498.
International Search Report dated Sep. 4, 2008 for Application No. PCT/JP2008/059491.
International Search Report dated Sep. 4, 2008 for Application No. PCT/JP2008/059492.
International Search Report dated Sep. 4, 2008 for Application No. PCT/JP2008/059498.
Database WPI Week 200560; Thomson Scientific, London, GB; AN; 2005-585455; XP002493506.
Bellstein Registry Nos. 6215504, 6236294, 4325236, 6203175, 621969, 8220992.
Benefice et al., "Reactivate Comparee des Perfluoroiodoalcanes (RFI) et des Perfluoroalcoyl-2 I0D0-1 Ethanes (RFCH2CH2I) en Presence de Couple Metal-Lique Zinc-Cuivre Dans un Solvant Dissociant Particulier: Le Sulfolane (RF=CnF2n+1=n pair)," Journal of Fluorine Chemistry, vol. 23, 1983, pp. 47-55.
Brace et al., "Oxidation chemistry of perfluoroalkyl-segmented thiols, disulfides, thiosulfinates and thiosulfonates. The role of the perfluoroalkyl group in searching out new chemistry," Journal of Fluorine Chemistry, vol. 105, 2000, pp. 11-23.
Chemical Abstract, "Fluro type surfactants," XP-002415663.
Dieng et al., "Synthese et Application de Nouveaux Sulfures a Chaine perfluoree," Journal of Fluorine Chemistry. vol. 28, 1985, pp. 341-355.
Dieng et al., "Syntheses et Reactivate Des F-Alkyl Sulfures et Sulfones Actives," Journal of Fluorine Chemistry, vol. 28, 1985, pp. 425-440.

(Continued)

*Primary Examiner* — Kamal Saeed
*Assistant Examiner* — Nyeemah A Grazier
(74) *Attorney, Agent, or Firm* — Birch, Stewart, Kolasch & Birch, LLP

(57) ABSTRACT

There is provided an organic sulfur compound having an excellent controlling effect on harmful arthropods which is represented by formula (I):

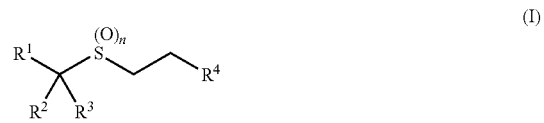

(I)

wherein $R^1$ represents a C3-C6 haloalkyl group having at least one fluorine atom and at least one atom selected from group consisting of a chlorine atom, a bromine atom and an iodine atom, $R^2$ represents a cyano group and the like, $R^3$ represents a hydrogen atom, a halogen atom or a C1-C4 alkyl group, $R^4$ represents a C1-C5 fluoroalkyl group, and n represents 0, 1 or 2.

9 Claims, No Drawings

OTHER PUBLICATIONS

Faurote et al., "Some New Polyfluoroalkyl Halides, H(CF2)nCH2X, and the Reactions of H(CF2)nCH2I with Water, Sulfur and Selenium," Journal of Am. Chem. Soc., vol. 78, 1956, pp. 4999-5001.

Fokin et al., "Some Properties of Fluorine-containing a,B-Unsaturated Sulfones," English Translation from Zhurnal Organicheskol Khimii, vol. 22, No. 2, 1986, pp. 270-276.

Ilin et al., "Comparison of CF3-Substituted Ethylenic Compounds in Reactions with Chlorines of Sulfur," Zhurnal Vses. Khim. Ob-va im. D.I. Mendeieeva, vol. 28, No. 2, 1983, pp. 115-116, including 4-page English translation.

Mir et al., "Reactions of Hexafluoroacetone with Sulfur-Containing Compounds," Inorg. Chem., vol. 19, 1980, pp. 1510-1514.

Naud et al., "Synthesis of terminally perfluorinated long-chain alkanethiols, sulfides and disulfides from the corresponding halides," Journal of Fluorine Chemistry, vol. 104, 2000, pp. 173-183.

Notice of Allowance dated Jun. 3, 2011 for U.S. Appl. No. 12/094,255.

Office Action dated Dec. 8, 2010 for U.S. Appl. No. 12/094,255.

Office Action in Australian Patent Application No. 2006317486 mailed Dec. 14, 2010.

Office Action in European Application No. 06832438.3 mailed Apr. 16, 2009.

Rocaboy et al., "Syntheses, oxidations, and palladium complexes of fluorous dialkyl sulfides: new precursors to highly active catalysts for the Suzuki coupling," Tetrahedron, vol. 58, 2002, pp. 4007-4014.

Serdyuk et al., "Polyfluoroalkylthiotrifluoroacetylketenes," Russian Chemical Bulletin, International Edition, vol. 52, No. 8, 2003, pp. 1854-1858.

Serratrice et al., "Etude RMN Du13 C De Composes Fluoroaliphatiques et de Tensio-Actifs Non Ioniques Perfluoroalkyles," Journal of Fluorine Chemistry, vol. 25, 1984, pp. 275-288.

Shkurak et al., "Activated Addition of Sulfur Chlorides and Sulfenyl Chlorides to Hexafluorodimethylketene," pp. 1261-1268 and pp. 1371-1377 with English Translation.

Sodoyer et al., "Synthese de Nouvelles Sulfones F-Alkylees Saturees et a,B-Insaturees," Journal of Fluorine Chemistry, vol. 22, 1983, pp. 401-419.

Szonyi et al., "Fonctionnalisation Des Iodures de F-Alkyl-2 Ethane par Catalyze Par Transfert de Phase: Importance de Cette Technique en Serie F-Alkylee," Journal of Fluorine Chemistry, vol. 42, 1989, pp. 59-68.

* cited by examiner

ORGANIC SULFUR COMPOUND AND ITS USE FOR CONTROLLING HARMFUL ARTHROPOD

TECHNICAL FIELD

The present invention relates to an organic sulfur compound and a use thereof for controlling harmful arthropods.

BACKGROUND ART

Hitherto, many pesticidal compositions for controlling harmful arthropods have been developed and used practically. Further, JP-A 2004-130306 discloses a certain fluorine-containing organic sulfur compound.

DISCLOSURE OF THE INVENTION

An object of the present invention is to provide a novel compound having an excellent controlling effect on harmful arthropods and its use.

The present inventors have intensively studied to find out a compound having an excellent controlling effect on harmful arthropods. As a result, they have found that an organic sulfur compound represented by the following formula (I) has an excellent controlling effect on harmful arthropods such as harmful insects and harmful mites. Thus, the present invention has been completed.

That is, the present invention provides:

(1) An organic sulfur compound represented by the formula (I):

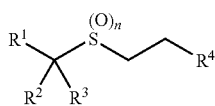

(I)

wherein $R^1$ represents a C3-C6 haloalkyl group having at least one fluorine atom and at least one atom selected from the group consisting of a chlorine atom, a bromine atom and an iodine atom, $R^2$ represents a cyano group, $C(=Q)OR^5$ or $C(=Q)N(R^6)_2$, $R^3$ represents a hydrogen atom, a halogen atom or a C1-C4 alkyl group, $R^4$ represents a C1-C5 fluoroalkyl group, Q represents an oxygen atom or a sulfur atom, $R^5$ represents a C1 to C4 alkyl group, $R^6$'s each independently represent a hydrogen atom or a C1-C4 alkyl group, or two $R^6$'s are bonded to each other at their terminals to form a C2-C7 alkylene group, and n represents 0, 1 or 2 (hereinafter, sometimes, referred to as the compound of the present invention);

(2) The organic sulfur compound according to the above (1), wherein n is 2;

(3) The organic sulfur compound according to the above (1) or (2), wherein Q is an oxygen atom;

(4) The organic sulfur compound according to the above (1) or (2), wherein $R^2$ is a cyano group;

(5) The organic sulfur compound according to the above (1) or (2), wherein $R^2$ is $C(=Q)N(R^6)_2$, and $R^6$'s are each independently a hydrogen atom or a C1-C4 alkyl group;

(6) The organic sulfur compound according to the above (1) or (2), wherein $R^2$ is $C(=Q)N(R^6)_2$, and $R^6$ is a hydrogen atom;

(7) The organic sulfur compound according to any one of the above (1) to (6), wherein $R^3$ is a halogen atom;

(8) A pesticidal composition comprising the organic sulfur compound according to any one of the above (1) to (7) as an effective component;

(9) A method for controlling harmful arthropods comprising applying an effective amount of the organic sulfur compound according to any one of the above (1) to (7) to harmful arthropods or a place where harmful arthropods inhabit;

(10) A use of the organic sulfur compound according to any one of the above (1) to (7) for production of a pesticidal composition; and the like.

BEST MODE FOR CARRYING OUT THE INVENTION

In the present invention, the expression "C1-C4" or the like means the total number of carbon atoms constituting each substituent group.

In the formula (I), examples of the "C3-C6 haloalkyl group having at least one fluorine atom and at least one atom selected from the group consisting of a chlorine atom, a bromine atom and an iodine atom" represented by $R^1$ include (1) a C3-C6 haloalkyl group having at least one fluorine atom and at least one chlorine atom, (2) a C3-C6 haloalkyl group having at least one fluorine atom and at least one bromine atom, and (3) a C3-C6 haloalkyl group having at least one fluorine atom, at least one chlorine atom and at least one bromine atom.

Examples of (1) a C3-C6 haloalkyl group having at least one fluorine atom and at least one chlorine atom include a C3 haloalkyl group such as a 3-chloro-3,3-difluoropropyl group, a 1-chloro-1,3,3,3-tetrafluoropropyl group, a 2,3-dichloro-2,3,3-trifluoropropyl group and a 2,2-dichloro-3,3,3-trifluoropropyl group; a C4 haloalkyl group such as a 2-chloro-2,4,4,4-tetrafluorobutyl group, a 3,4-dichloro-3,4,4-trifluorobutyl group, a 3,3-dichloro-4,4,4-trifluorobutyl group, a 4-chloro-1,1,2,3,3,4,4-heptafluorobutyl group, a 3,3-dichloro-4,4,4-trifluorobutyl group and a 3,4-dichloro-3,4,4-trifluorobutyl group; and a C5 haloalkyl group such as a 5-chloro-2,2,3,4,4,5,5-heptafluoropentyl group, a 4,4-dichloro-5,5,5-trifluoropentyl group and a 4,5-dichloro-4,5,5-trifluoropentyl group.

Examples of (2) a C3-C6 haloalkyl group having at least one fluorine atom and at least one bromine atom include a C3 haloalkyl group such as a 2,2-dibromo-3,3,3-trifluoropropyl group, a 2-bromo-3,3,3-trifluoropropyl group, a 2,3-dibromo-3,3-difluoropropyl group, a 3-bromo-3,3-difluoropropyl group, a 1-bromo-1,3,3,3-tetrafluoropropyl group, a 1-bromo -2,2,3,3,3-pentafluoropropyl group, a 1,3-dibromo-2,2,3,3-tetrafluoropropyl group, a 3-bromo -2,3,3-trifluoropropyl group, a 3-bromo-2,2,3,3-tetrafluoropropyl group, a 2,3-dibromo-2,3,3-trifluoropropyl group and a 3-bromo-3,3-difluoropropyl group; a C4 haloalkyl group such as a 2-bromo-2,4,4,4-tetrafluorobutyl group, a 2-bromo-3,3,4,4,4-pentafluorobutyl group, a 2,4-dibromo-3,3,4,4-tetrafluorobutyl group, a 4-bromo-3,4,4-trifluorobutyl group, a 4-bromo-3,3,4,4-tetrafluorobutyl group, a 3,4-dibromo-3,4,4-trifluorobutyl group group, a 4-bromo-4,4-difluorobutyl group and a 4-bromo -3,3,4,4-tetrafluorobutyl group; a C5 haloalkyl group such as a 5-bromo-4,4,5,5-tetrafluoropentyl group, a 1-bromo-2,2,3,3,4,4,5,5,5-nonafluoropentyl group and a 1,1-dibromo-2,2,3,3,4,4,5,5,5-nonafluoropentyl group; and a C6 haloalkyl group such as a 2-bromo-3,3,4,4,5,5,6,6,6-nonafluorohexyl group and a 2,2-dibromo-3,3,4,4,5,5,6,6,6-nonafluorohexyl group.

Examples of (3) a C3-C6 haloalkyl group having at least one fluorine atom, at least one chlorine atom and at least one bromine atom include a C3 haloalkyl group such as a 3-bromo-2-chloro-3,3-difluoropropyl group and a 3-bromo-2-chloro-2,3,3-trifluoropropyl group; a C4 haloalkyl group such as a 4-bromo-3-chloro-4,4-difluorobutyl group, a 4-bromo-3-chloro-3,4,4-trifluorobutyl group, a 3-chloro-1,4-dibromo-3,4,4-trifluorobutyl group and a 4-bromo-3-chloro-3,4,4-trifluorobutyl group; a C5-C6 haloalkyl group such as a 4-chloro-2,5-dibromo-4,5,5-trifluoropentyl group, a 5-bromo-4-chloro-4,5,5-trifluoropentyl group, a 5-bromo-4-chloro-4,5,5-trifluoropentyl group and a 6-bromo-5-chloro-5,6,6-trifluorohexyl group.

In the present invention, preferred examples of the "C3-C6 haloalkyl group having at least one fluorine atom and at least one atom selected from the group consisting of a chlorine atom, a bromine atom and an iodine atom" include a group represented by the following formula:

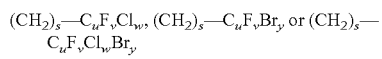

wherein s represents an integer of 0 to 3, u represents an integer of 1 to 3, and v, w and y independently represent an integer of 1 to 6; provided that s+u is 6 or less, and v+w+y=2u+1.

Examples of the "C1-C5 fluoroalkyl group" represented by $R^4$ in the formula (I) include a C1-C2 fluoroalkyl group such as a fluoromethyl group, a difluoromethyl group, a trifluoromethyl group, a 1-fluoroethyl group, a 2-fluoroethyl group, a 1,1-difluoroethyl group, a 2,2-difluoroethyl group, a 2,2,2-trifluoroethyl group and a 1,1,2,2,2-pentafluoroethyl group; a C3 fluoroalkyl group such as a 1-fluoropropyl group, a 1,1-difluoropropyl group, a 2-fluoropropyl group, a 2,2-difluoropropyl group, a 3-fluoropropyl group, a 3,3-difluoropropyl group, a 3,3,3-trifluoropropyl group, a 1,1,2,2,3,3,3-heptafluoropropyl group, a 2,2,3,3,3-pentafluoropropyl group, a 2,2,2-trifluoro-(1-trifluoromethyl)ethyl group, a 1,2,2,2-tetrafluoro-(1-trifluoromethyl)ethyl group and a 2,2,3,3-tetrafluoropropyl group; a C4 fluoroalkyl group such as a 1-fluorobutyl group, a 1,1-difluorobutyl group, a 2-fluorobutyl group, a 2,2-difluorobutyl group, a 3-fluorobutyl group, a 3,3-difluorobutyl group, a 4-fluorobutyl group, a 4,4-difluorobutyl group, a 4,4,4-trifluorobutyl group, a 3,3,4,4,4-pentafluorobutyl group, a 2,2,3,4,4-pentafluorobutyl group and a 2,2,3,3,4,4,4-heptafluorobutyl group; and, a C5 fluoroalkyl group such as a 1-fluoropentyl group, a 1,1-difluoropentyl group, a 2-fluoropentyl group, a 2,2-difluoropentyl group, a 3-fluoropentyl group, a 3,3-difluoropentyl group, a 4-fluoropentyl group, a 4,4-difluoropentyl group, a 5-fluoropentyl group, a 5,5-difluoropentyl group, a 5,5,5-trifluoropentyl group, a 4,4,5,5,5-pentafluoropentyl group, a 3,3,4,4,5,5,5-heptafluoropentyl group, a 2,2,3,3,4,4,5,5-octafluoropentyl group and a 2,2,3,3,4,4,5,5,5-nonafluoropentyl group.

In the present invention, preferred examples of the "C1-C5 fluoroalkyl group" include a group represented by the following formula:

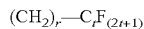

wherein r represents an integer of 0 to 4, and t represents an integer of 1 to 3, provided that r+t is 5 or less.

Examples of the "C1-C4 alkyl group" represented by $R^3$ in the formula (I) include a methyl group, an ethyl group, a propyl group, an isopropyl group, a butyl group, an isobutyl group and a tert-butyl group.

Examples of the "C1-C4 alkyl group" represented by $R^5$ in the formula (I) include a methyl group, an ethyl group, a propyl group, an isopropyl group, a butyl group, an isobutyl group and a tert-butyl group.

Examples of the "C1-C4 alkyl group" represented by $R^6$ in the formula (I) include a methyl group, an ethyl group, a propyl group, an isopropyl group, a butyl group, an isobutyl group and a tert-butyl group.

Examples of the "C2-C7 alkylene group" formed by bonding of two $R^6$'s at their terminals include an ethylene group, a trimethylene group, a tetramethylene group and a hexamethylene group.

Examples of a group represented by $N(R^6)_2$ include acyclic amino groups such as amino group, methylamino group, ethylamino group, propylamino group, 2-propylamino group, butylamino group, isobutylamino group, tert-butylamino group, and dimethylamino group; and cyclic amino groups such as 1-aziridino group, 1-azetidinyl group, 1-pyrrolidinyl group and piperidino group.

Specific examples of the compound of the present invention include:

an organic sulfur compound represented by the formula (I) wherein n is 2;

an organic sulfur compound represented by the formula (I) wherein Q is an oxygen atom;

an organic sulfur compound represented by the formula (I) wherein $R^2$ is $C(=Q)OR^5$ or $C(=Q)N(R^6)_2$;

an organic sulfur compound represented by the formula (I) wherein $R^2$ is $C(=Q)N(R^6)_2$ and $R^6$'s are each independently a hydrogen atom or a C1-C4 alkyl group;

an organic sulfur compound represented by the formula (I) wherein $R^2$ is $C(=Q)N(R^6)_2$ and $R^6$ is a hydrogen atom;

an organic sulfur compound represented by the formula (I) wherein $R^1$ is a group represented by the formula:

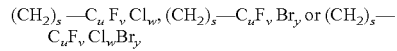

wherein s represents an integer of 0 to 3, u represents an integer of 1 to 3, and v, w and y independently represent an integer of 1 to 6, provided that s+u is 6 or less, and v+w+y=2u+1;

an organic sulfur compound represented by the formula (I) wherein $R^3$ is a hydrogen atom, a fluorine atom, a chlorine atom or an alkyl group;

an organic sulfur compound represented by the formula (I) wherein $R^3$ is a hydrogen atom;

an organic sulfur compound represented by the formula (I) wherein $R^3$ is a halogen atom;

an organic sulfur compound represented by the formula (I) wherein $R^3$ is a fluorine atom or a chlorine atom;

an organic sulfur compound represented by the formula (I) wherein $R^3$ is a methyl group;

an organic sulfur compound represented by the formula (I) wherein $R^4$ is a group represented by the formula:

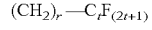

wherein r represents an integer of 0 to 4, and t represents an integer of 1 to 3, provided that r+t is 5 or less;

an organic sulfur compound represented by the formula (I) wherein $R^4$ is a C1-C3 fluoroalkyl group;

an organic sulfur compound represented by the formula (I) wherein $R^4$ is a trifluoromethyl group, a 1,1,2,2,2-pentafluoroethyl group, a 2,2,2-trifluoroethyl group or a 1,1,2,2,3,3,3-heptafluoropropyl group;

an organic sulfur compound represented by the formula (I) wherein $R^4$ is a trifluoromethyl group;

an organic sulfur compound represented by the formula (I) wherein $R^4$ is a 1,1,2,2,2-pentafluoroethyl group;

an organic sulfur compound represented by the formula (I) wherein $R^4$ is a 2,2,2-trifluoroethyl group;

an organic sulfur compound represented by the formula (I) wherein $R^4$ is a 1,1,2,2,3,3,3-heptafluoropropyl group;

an organic sulfur compound represented by the formula (I) wherein Q is an oxygen atom and $R^3$ is a hydrogen atom;

an organic sulfur compound represented by the formula (I) wherein Q is an oxygen atom and $R^3$ is a halogen atom;

an organic sulfur compound represented by the formula (I) wherein Q is an oxygen atom and $R^3$ is a fluorine atom or a chlorine atom;

an organic sulfur compound represented by the formula (I) wherein Q is an oxygen atom and $R^3$ is a methyl group;

an organic sulfur compound represented by the formula (I) wherein $R^2$ is a cyano group;

an organic sulfur compound represented by the formula (I) wherein $R^2$ is a cyano group and $R^3$ is a halogen atom;

an organic sulfur compound represented by the formula (I) wherein $R^2$ is a cyano group and $R^3$ is a fluorine atom or a chlorine atom;

an organic sulfur compound represented by the formula (I) wherein $R^2$ is a cyano group and $R^3$ is a methyl group;

an organic sulfur compound represented by the formula (I) wherein $R^2$ is $C(=Q)OR^5$ or $C(=Q)N(R^6)_2$ and $R^3$ is a hydrogen atom;

an organic sulfur compound represented by the formula (I) wherein $R^2$ is $C(=Q)OR^5$ or $C(=Q)N(R^6)_2$ and $R^3$ is a halogen atom;

an organic sulfur compound represented by the formula (I) wherein $R^2$ is $C(=Q)OR^5$ or $C(=Q)N(R^6)_2$ and $R^3$ is a fluorine atom or a chlorine atom;

an organic sulfur compound represented by the formula (I) wherein $R^2$ is $C(=Q)OR^5$ or $C(=Q)N(R^6)_2$ and $R^3$ is a methyl group;

an organic sulfur compound represented by the formula (I) wherein $R^2$ is $C(=Q)N(R^6)_2$ and $R^3$ is a hydrogen atom;

an organic sulfur compound represented by the formula (I) wherein $R^2$ is $C(=Q)N(R^6)_2$ and $R^3$ is a halogen atom;

an organic sulfur compound represented by the formula (I) wherein $R^2$ is $C(=Q)N(R^6)_2$ and $R^3$ is a fluorine atom or a chlorine atom;

an organic sulfur compound represented by the formula (I) wherein $R^2$ is $C(=Q)N(R^6)_2$ and $R^3$ is a methyl group;

an organic sulfur compound represented by the formula (I) wherein $R^2$ is $C(=Q)N(R^6)_2$, $R^6$ is a hydrogen atom and $R^3$ is a halogen atom;

an organic sulfur compound represented by the formula (I) wherein $R^2$ is $C(=Q)N(R^6)_2$, $R^6$ is a hydrogen atom and $R^3$ is a fluorine atom or a chlorine atom;

an organic sulfur compound represented by the formula (I) wherein $R^2$ is $C(=Q)N(R^6)_2$, $R^6$ is a hydrogen atom and $R^3$ is a methyl group;

an organic sulfur compound represented by the formula (I) wherein n is 2, $R^2$ is a cyano group and $R^3$ is a hydrogen atom;

an organic sulfur compound represented by the formula (I) wherein n is 2, $R^2$ is a cyano group and $R^3$ is a halogen atom;

an organic sulfur compound represented by the formula (I) wherein n is 2, $R^2$ is a cyano group and $R^3$ is a fluorine atom or a chlorine atom;

an organic sulfur compound represented by the formula (I) wherein n is 2, $R^2$ is a cyano group and $R^3$ is a methyl group;

an organic sulfur compound represented by the formula (I) wherein n is 2, $R^2$ is $C(=Q)N(R^6)_2$ and $R^3$ is a hydrogen atom;

an organic sulfur compound represented by the formula (I) wherein n is 2, $R^2$ is $C(=Q)N(R^6)_2$ and $R^3$ is a halogen atom;

an organic sulfur compound represented by the formula (I) wherein n is 2, $R^2$ is $C(=Q)N(R^6)_2$ and $R^3$ is a fluorine atom or a chlorine atom;

an organic sulfur compound represented by the formula (I) wherein n is 2, $R^2$ is $C(=Q)N(R^6)_2$ and $R^3$ is a methyl group;

an organic sulfur compound represented by the formula (I) wherein n is 2, $R^2$ is $C(=Q)N(R^6)_2$, $R^6$ is a hydrogen atom and $R^3$ is a hydrogen atom;

an organic sulfur compound represented by the formula (I) wherein n is 2, $R^2$ is $C(=Q)N(R^6)_2$, $R^6$ is a hydrogen atom and $R^3$ is a halogen atom;

an organic sulfur compound represented by the formula (I) wherein n is 2, $R^2$ is $C(=Q)N(R^6)_2$, $R^6$ is a hydrogen atom and $R^3$ is a fluorine atom or a chlorine atom;

an organic sulfur compound represented by the formula (I) wherein n is 2, $R^2$ is $C(=Q)N(R^6)_2$, R6 is a hydrogen atom and $R^3$ is a methyl group;

an organic sulfur compound represented by the formula (I) wherein $R^1$ is a group represented by the formula:

$$(CH_2)_s-C_uF_vCl_w, (CH_2)_s-C_uF_vBr_y \text{ or } (CH_2)_s-C_uF_vCl_wBr_y$$

wherein s represents an integer of 0 to 3, u represents an integer of 1 to 3, and v, w and y independently represent an integer of 1 to 6, provided that s+u is 6 or less, and v+w+y=2u+1, $R^2$ is a cyano group, $C(=O)OR^5$ or $C(=O)N(R^6)_2$, $R^3$ is a hydrogen atom, a methyl group, an ethyl group, a fluorine atom or a chlorine atom, $R^4$ is a trifluoromethyl group, 1,1,2,2,2-pentafluoroethyl group, 2,2,2-trifluoroethyl group or 1,1,2,2,3,3,3-heptafluoropropyl group, $R^5$ is a methyl group, and $R^6$'s are each independently a hydrogen atom or a methyl group; and an organic sulfur compound represented by the formula (I) wherein $R^1$ is a group represented by the formula:

$$(CH_2)_s-C_uF_vCl_w, \text{ or } (CH_2)_s-C_uF_vBr_y$$

wherein s represents an integer of 0 to 3, u represents an integer of 1 to 3, and v, w and y independently represent an integer of 1 to 6, provided that s+u is 6 or less, and v+w+y=2u+1, $R^2$ is a cyano group, $C(=O)OR^5$ or $C(=O)N(R^6)_2$, $R^3$ is a hydrogen atom or a chlorine atom, $R^4$ is a trifluoromethyl group, $R^5$ is a methyl group, and $R^6$ is a hydrogen atom.

Next, a process for production of the compound of the present invention is explained. The compound of the present invention can be produced, for example, by the following Production Processes 1 to 12.

Production Process 1

Among the compounds of the present invention, a compound (I-2) that is a compound of the formula (I) wherein $R^3$ is a C1-C4 alkyl group can be produced, for example, by reacting a compound (a) with a compound (I-1) as follows:

wherein $R^1$, $R^2$, $R^4$ and n are as defined above, $R^{3-1}$ represents a C1-C4 alkyl group, X represents a leaving group such as a chlorine atom, a bromine atom, an iodine atom, a methanesulfonyloxy group, a p-toluenesulfonyloxy group or a trifluoromethanesulfonyloxy group.

The reaction is usually carried out in a solvent in the presence of a base.

Examples of a solvent used in the reaction include acid amides such as N,N-dimethylformamide, ethers such as diethyl ether and tetrahydrofuran, organic sulfurs such as dimethyl sulfoxide and sulfolane, halogenated hydrocarbons such as chloroform, 1,2-dichloroethane and chlorobenzene, aromatic hydrocarbons such as toluene and xylene, water and a mixture thereof.

Examples of a base used in the reaction include inorganic bases such as sodium hydride, sodium hydroxide, potassium hydroxide and potassium carbonate, alkali metal alkoxides such as sodium methoxide and potassium tert-butoxide, alkali metal amides such as lithium diisopropylamide, and organic bases such as triethylamine, 1,4-diazabicyclo[2.2.2]octane and 1,8-diazabicyclo[5.4.0]-7-undecene.

The amount of the base used in the reaction is usually 1 to 10 mol relative to 1 mol of the compound (I-1).

The amount of the compound (a) used in the reaction is usually 1 to 10 mol relative to 1 mol of the compound (I-1).

The reaction temperature is usually in a range of −100 to 100° C., and the reaction time is usually 1 to 24 hours.

After completion of the reaction, the compound (I-2) can be isolated by post-treatment, for example, by pouring a reaction mixture into water and extracting the resulting mixture with an organic solvent followed by concentration. The isolated compound (I-2) can be further purified by chromatography, recrystallization or the like, if necessary.

Production Process 2

Among the compounds of the present invention, a compound (I-3) that is a compound of the formula (I) wherein $R^3$ is a hydrogen atom or a C1-C4 alkyl group can be produced, for example, by reacting a compound (c) with a compound (d) as follows:

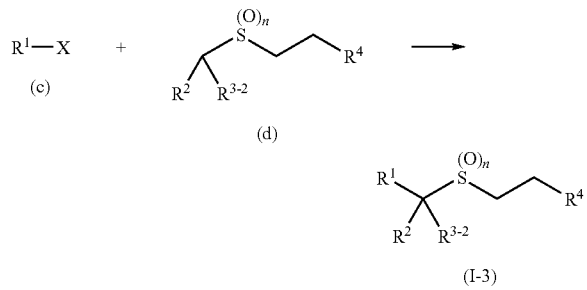

wherein $R^1$, $R^2$, $R^4$, n and X are as defined above, $R^{3-2}$ represents a hydrogen atom or a C1-C4 alkyl group.

The reaction is usually carried out in a solvent in the presence of a base.

Examples of a solvent used in the reaction include acid amides such as N,N-dimethylformamide, ethers such as diethyl ether and tetrahydrofuran, organic sulfurs such as dimethyl sulfoxide and sulfolane, halogenated hydrocarbons such as chloroform, 1,2-dichloroethane and chlorobenzene, aromatic hydrocarbons such as toluene and xylene, water and a mixture thereof.

Examples of a base used in the reaction include inorganic bases such as sodium hydride, sodium hydroxide, potassium hydroxide and potassium carbonate, alkali metal alkoxides such as sodium methoxide and potassium tert-butoxide, alkali metal amides such as lithium diisopropylamide, and organic bases such as triethylamine, 1,4-diazabicyclo[2.2.2]octane and 1,8-diazabicyclo[5.4.0]-7-undecene.

The amount of the base used in the reaction is usually 1 to 10 mol relative to 1 mol of the compound (d).

The amount of compound (c) used in the reaction is usually 1 to 10 mol relative to 1 mol of the compound (d).

The reaction temperature is usually in a range of −100 to 100° C., and the reaction time is usually 1 to 24 hours.

After completion of the reaction, the compound (I-3) can be isolated by post-treatment, for example, by pouring a reaction mixture into water and extracting the resulting mixture with an organic solvent followed by concentration. The isolated compound (I-3) can be further purified by chromatography, recrystallization or the like, if necessary.

Among the compounds of the present invention, a compound (I-4) that is a compound of the formula (I) wherein $R^3$ is a halogen atom, can be produced for example, by the following Production Process 3 or Production Process 4.

Production Process 3

This process comprises reacting a compound (I-1) with a halogenating agent (e) in the presence of a base as follows:

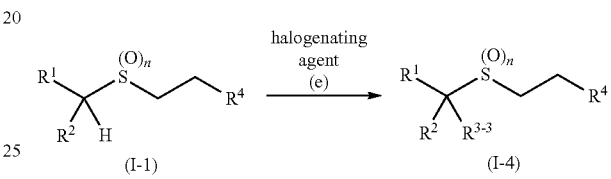

wherein $R^1$, $R^2$, $R^4$ and n are as defined above, $R^{3-3}$ represents a halogen atom.

The reaction is usually carried out in a solvent in the presence of a base.

Examples of a solvent used in the reaction include acid amides such as N,N-dimethylformamide, ethers such as diethyl ether and tetrahydrofuran, organic sulfurs such as dimethyl sulfoxide and sulfolane, halogenated hydrocarbons such as chloroform, 1,2-dichloroethane and chlorobenzene, aromatic hydrocarbons such as toluene and xylene, water and a mixture thereof.

Examples of a base used in the reaction include inorganic bases such as sodium hydride, sodium hydroxide, potassium hydroxide and potassium carbonate, alkali metal alkoxides such as sodium methoxide and potassium tert-butoxide, alkali metal amides such as lithium diisopropylamide, and organic bases such as triethylamine, 1,4-diazabicyclo[2.2.2]octane and 1,8-diazabicyclo[5.4.0]-7-undecene.

The amount of the base used in the reaction is usually 1 to 10 mol relative to 1 mol of the compound (I-1).

Examples of the halogenating agent (e) used in the reaction include halogenated hydrocarbons such as carbon tetrachloride and hexachloroethane, halogens such as fluorine, chlorine, bromine and iodine, halogenated succinimides such as N-chlorosuccinimide, N-bromosuccinimide and N-iodosuccinimide, N-fluoropyridinium salts such as 1-fluoro-2,4,6-trimethylpyridiniumtrifluoromethanesulfonate and 1,1'-difluoro-2,2'-bipyridiniumbis-tetrafluoroborate, and inorganic salts such as copper (II) chloride and copper (II) bromide.

The amount of the halogenating agent (e) used in the reaction is usually 1 to 10 mol relative to 1 mol of the compound (I-1).

The reaction temperature is usually in a range of −100 to 100° C., and the reaction time is usually 1 to 24 hours.

After completion of the reaction, the compound (I-4) can be isolated by post-treatment, for example, by pouring a reaction mixture into water and extracting the resulting mixture with an organic solvent followed by concentration. The isolated compound (I-4) can be further purified by chromatography, recrystallization, or the like, if necessary.

Production Process 4

This process comprises reacting a compound (I-1) with a halogenating agent (f) as follows:

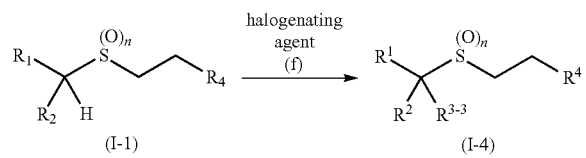

wherein $R^1$, $R^2$, $R^4$, $R^{3-3}$ and n are as defined above.

The reaction can be carried out without any solvent or in a solvent.

Examples of a solvent used in the reaction include halogenated hydrocarbons such as chloroform, carbon tetrachloride, 1,2-dichloroethane and chlorobenzene, aromatic hydrocarbons such as toluene and xylene, aliphatic nitriles such as acetonitrile and propionitrile, aliphatic carboxylic acids such as acetic acid, carbon disulfide, water and a mixture thereof.

Examples of the halogenating agent (f) used in the reaction include halogens such as fluorine, chlorine, bromine and iodine; halogenated sulfur compounds including halogenated hydrogen such as hydrogen fluoride, hydrogen chloride, hydrogen bromide and hydrogen iodide, thionyl chloride, thionyl bromide and sulfuryl chloride; and halogenated phosphorous compounds such as phosphorous trichloride, phosphorous tribromide, phosphorous pentachloride and phosphorous oxychloride.

The amount of the halogenating agent (f) used in the reaction is usually 1 to 10 mol relative to 1 mol of the compound (I-1).

The reaction temperature is usually in a range of −100 to 200° C., and the reaction time is usually 1 to 24 hours.

After completion of the reaction, the compound (I-4) can be isolated by post-treatment, for example, by pouring a reaction mixture into water and extracting the resulting mixture with an organic solvent followed by concentration. The isolated compound (I-4) can be further purified by chromatography, recrystallization or the like, if necessary.

Among the compounds of the present invention, a compound (I-5) that is a compound of the formula (I) wherein $R^2$ is $C(=O)OR^5$ or $C(=O)N(R^6)_2$ can be produced, for example, by the following Production Process 5 or Production Process 6.

Production Process 5

This process comprises reacting a compound (i) with a compound (j) as follows:

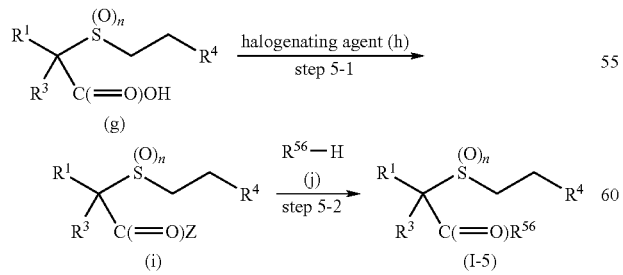

wherein $R^1$, $R^3$, $R^4$ and n are as defined above, Z represents a halogen atom, $R^{56}$ represents $OR^5$ or $N(R^6)_2$ (wherein $R^5$ and $R^6$ are as defined above).

Step 5-1

The compound (i) can be produced by reacting a compound (g) with a halogenating agent (h).

This reaction can be carried out without any solvent or in a solvent.

Examples of a solvent used in the reaction include halogenated hydrocarbons such as chloroform, dichloromethane, 1,2-dichloroethane and chlorobenzene, and aromatic hydrocarbons such as toluene and xylene.

Examples of the halogenating agent (h) used in the reaction include oxalyl chloride, thionyl chloride, thionyl bromide, phosphorous trichloride, phosphorous tribromide and phosphorous pentachloride.

The amount of halogenating agent (h) used in the reaction is usually from 1 mol to a sufficient amount as a solvent relative to 1 mol of the compound (g).

The reaction temperature is usually in a range of −20 to 100° C., and the reaction time is usually 1 to 24 hours.

After completion of the reaction, the compound (i) can be isolated by a treatment such as concentration of a reaction mixture. The isolated compound (i) can be further purified by distillation, or the like.

Step 5-2

The reaction is usually carried out in a solvent in the presence of base.

Examples of a solvent used in the reaction include acid amides such as N,N-dimethylformamide, ethers such as diethyl ether and tetrahydrofuran, organic sulfurs such as dimethyl sulfoxide and sulfolane, halogenated hydrocarbons such as chloroform, 1,2-dichloroethane and chlorobenzene, aromatic hydrocarbons such as toluene and xylene, water and a mixture thereof.

Examples of a base used in the reaction include inorganic bases such as sodium hydride, sodium hydroxide, potassium hydroxide and potassium carbonate, and organic bases such as triethylamine, 1,4-diazabicyclo[2.2.2]octane and 1,8-diazabicyclo[5.4.0]-7-undecene.

The amount of the base used in the reaction is usually 1 to 10 mol relative to 1 mol of the compound (i).

The amount of the compound (j) used in the reaction is usually 1 to 10 mol relative to 1 mol of the compound (i).

The reaction temperature is usually in a range of −20 to 100° C., and the reaction time is usually 1 to 24 hours.

After completion of the reaction, the a compound (I-5) can be isolated by post-treatment, for example, by pouring a reaction mixture into water and extracting the resulting mixture with an organic solvent followed by concentration. The isolated compound (I-5) can be further purified by chromatography, recrystallization or the like, if necessary.

Production Process 6

This process comprises reacting a compound (g) with a compound (j) as follows:

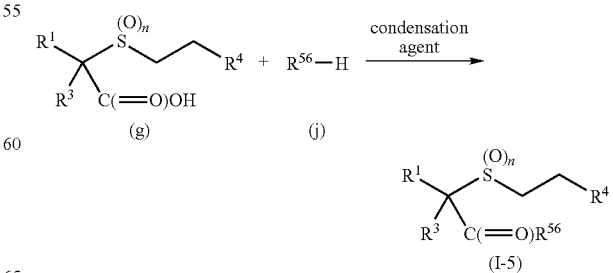

wherein $R^1$, $R^3$, $R^4$, $R^{56}$ and n are as defined above.

The reaction is usually carried out in a solvent in the presence of a condensation agent.

Examples of a solvent used in the reaction include ethers such as diethyl ether and tetrahydrofuran, organic sulfurs such as dimethyl sulfoxide and sulfolane, halogenated hydrocarbons such as chloroform, 1,2-dichloroethane and chlorobenzene, and aromatic hydrocarbons such as toluene and xylene.

Examples of the condensation agent used in the reaction include dicyclohexylcarbodiimide, N-(3-dimethylaminopropyl)-N'-ethylcarbodiimide and carbonyldiimidazole.

The amount of the condensation agent used in the reaction is usually 1 to 10 mol relative to 1 mol of the compound (g).

The amount of the compound (j) used in the reaction is usually 1 to 10 mol relative to 1 mol of the compound (g).

The reaction temperature is usually in a range of −20 to 100° C., and the reaction time is usually 1 to 24 hours.

After completion of the reaction, the compound (I-5) can be isolated by a treatment such as concentration of a reaction mixture. The isolated compound (I-5) can be further purified by chromatography, recrystallization, or the like, if necessary.

Production Process 7

Among the compounds of the present invention, a compound (I-1) that is a compound of the formula (I) wherein $R^3$ is a hydrogen atom can be produced, for example, by reacting a compound (c) with a compound (k) as follows:

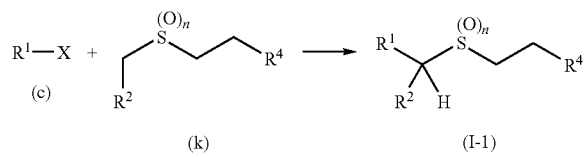

wherein $R^1$, $R^2$, $R^4$, X and n are as defined above.

The reaction is usually carried out in a solvent in the presence of base.

Examples of a solvent used in the reaction include acid amides such as N,N-dimethylformamide, ethers such as diethyl ether and tetrahydrofuran, organic sulfurs such as dimethyl sulfoxide and sulfolane, halogenated hydrocarbons such as chloroform, 1,2-dichloroethane and chlorobenzene, aromatic hydrocarbons such as toluene and xylene, water and a mixture thereof.

Examples of a base used in the reaction include inorganic bases such as sodium hydride, sodium hydroxide, potassium hydroxide and potassium carbonate; alkali metal alkoxides such as sodium methoxide and potassium tert-butoxide, alkali metal amides such as lithium diisopropylamide, and organic bases such as triethylamine, 1,4-diazabicyclo[2.2.2]octane and 1,8-diazabicyclo[5.4.0]-7-undecene.

The amount of the base used in the reaction is usually 1 to 10 mol relative to 1 mol of the compound (k).

The amount of the compound (c) used in the reaction is usually 1 to 10 mol relative to 1 mol of the compound k. The reaction temperature is usually in a range of −100 to 100° C., and the reaction time is usually 1 to 24 hours.

After completion of the reaction, the compound (I-1) can be isolated by post-treatment, for example, by pouring a reaction mixture into water and extracting the resulting mixture with an organic solvent followed by concentration.

The isolated compound (I-1) can be further purified by chromatography, recrystallization, or the like, if necessary.

Production Process 8

Among the compounds of the present invention, a compound (I-8) that is a compound of the formula (I) wherein $R^2$ is $C(=O)N(R^6)_2$ and n is 2 can also be produced by reacting a compound (I-7) that is a compound of the formula (I) wherein $R^2$ is $C(=O)OR^5$ and n is 2 with a compound (p) as follows:

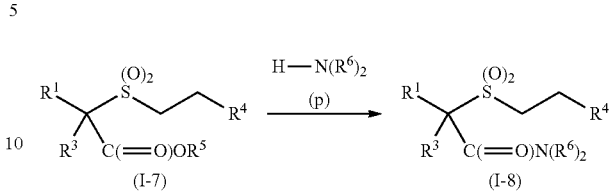

wherein $R^1$, $R^3$, $R^4$, $R^5$ and $R^6$ are as defined above.

The reaction is usually carried out in a solvent.

Examples of a solvent used in the reaction include ethers such as diethyl ether and tetrahydrofuran, organic sulfurs such as dimethyl sulfoxide and sulfolane, halogenated hydrocarbons such as chloroform, 1,2-dichloroethane and chlorobenzene, and aromatic hydrocarbons such as toluene and xylene.

The amount of the compound (p) used in the reaction is usually 1 to 10 mol relative to 1 mol of the compound (I-7).

The reaction temperature is usually in a range of −20 to 100° C., and the reaction time is usually 1 to 24 hours.

After completion of the reaction, the compound (I-8) can be isolated by a treatment such as concentration of a reaction mixture. The isolated compound (I-8) can be further purified by chromatography, recrystallization, or the like, if necessary.

Production Process 9

Among the compounds of the present invention, a compound (I-9) that is a compound of the formula (I) wherein $R^2$ is $C(=S)OR^5$ or $C(=S)N(R^6)_2$ can also be produced by reacting a compound (I-5) that is a compound of the formula (I) wherein $R^2$ is $C(=O)OR^5$ or $C(=O)N(R^6)_2$ with a sulfurizing agent (q) as follows:

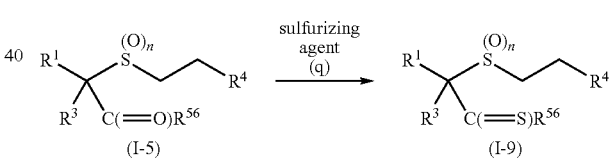

wherein $R^1$, $R^3$, $R^4$, $R^{56}$ and n are as defined above.

The reaction is usually carried out in a solvent.

Examples of a solvent used in the reaction include halogenated hydrocarbons such as chloroform, 1,2-dichloroethane and chlorobenzene, and aromatic hydrocarbons such as toluene and xylene.

Examples of the sulfurizing agent (q) used in the reaction include inorganic sulfur compounds such as hydrogen sulfide, diphosphorus pentasulfide, and organic sulfur compounds such as 2,4-bis(4-methoxyphenyl)-1,3-dithia-2,4-diphosphetane and 2,4-disulfide.

The amount of the sulfurizing agent (q) used in the reaction is usually 0.5 to 10 mol relative to 1 mol of the compound (I-5).

The reaction temperature is usually in a range of 0 to 250° C., and the reaction time is usually 1 to 72 hours.

After completion of the reaction, the compound (I-9) can be isolated by a treatment such as concentration of a reaction mixture. The isolated compound (I-9) can be further purified by chromatography, recrystallization, or the like, if necessary.

Among the compounds of the present invention, a compound (I-10) that is a compound of the formula (I) wherein n is 0 can be produced, for example, by the following Production Process 10 or Production Process 11.

Production Process 10

This process comprises reacting a compound (r) with a compound (m) as follows:

$$\underset{(r)}{R^1\underset{R^2\ R^{3\text{-}2}}{\bigvee}SH} + \underset{(m)}{X\diagdown\diagdown_{R^4}} \longrightarrow \underset{(I\text{-}10)}{R^1\underset{R^2\ R^{3\text{-}2}}{\bigvee}S\diagdown\diagdown_{R^4}}$$

wherein $R^1$, $R^2$, $R^{3\text{-}2}$, $R^4$ and X are as defined above.

The reaction is usually carried out in a solvent in the presence of a base.

Examples of a solvent used in the reaction include acid amides such as N,N-dimethylformamide, ethers such as diethyl ether and tetrahydrofuran, organic sulfurs such as dimethyl sulfoxide and sulfolane, halogenated hydrocarbons such as chloroform, 1,2-dichloroethane and chlorobenzene, aromatic hydrocarbons such as toluene and xylene, water and a mixture thereof.

Examples of a base used in the reaction include inorganic bases such as sodium hydride, sodium hydroxide, potassium hydroxide and potassium carbonate; alkali metal alkoxides such as sodium methoxide and potassium tert-butoxide, alkali metal amides such as lithium diisopropylamide, and organic bases such as triethylamine, 1,4-diazabicyclo[2.2.2]octane and 1,8-diazabicyclo[5.4.0]-7-undecene.

The amount of the base used in the reaction is usually 1 to 10 mol relative to 1 mol of the compound (r).

The amount of the compound (m) used in the reaction is usually 1 to 10 mol relative to 1 mol of the compound (r).

The reaction temperature is usually in a range of −20 to 100° C., and the reaction time is usually 1 to 24 hours.

After completion of the reaction, the compound (I-10) can be isolated by post-treatment, for example, by pouring a reaction mixture into water and extracting the resulting mixture with an organic solvent followed by concentration. The isolated compound (I-10) can be further purified by chromatography, recrystallization, or the like, if necessary.

Production Process 11

This process comprises reacting a compound (s) with a compound (O) as follows:

$$\underset{(s)}{R^1\underset{R^2\ R^{3\text{-}2}}{\bigvee}X} + \underset{(o)}{HS\diagdown\diagdown_{R^4}} \longrightarrow \underset{(I\text{-}10)}{R^1\underset{R^2\ R^{3\text{-}2}}{\bigvee}S\diagdown\diagdown_{R^4}}$$

wherein $R^1$, $R^2$, $R^{3\text{-}2}$, $R^4$, and X are as defined above.

The reaction is usually carried out in a solvent in the presence of a base.

Examples of a solvent used in the reaction include acid amides such as N,N-dimethylformamide, ethers such as diethyl ether and tetrahydrofuran, organic sulfurs such as dimethyl sulfoxide and sulfolane, halogenated hydrocarbons such as chloroform, 1,2-dichloroethane and chlorobenzene, aromatic hydrocarbons such as toluene and xylene, water and a mixture thereof.

Examples of a base used in the reaction include inorganic bases such as sodium hydride, sodium hydroxide, potassium hydroxide and potassium carbonate; alkali metal alkoxides such as sodium methoxide and potassium tert-butoxide, alkali metal amides such as lithium diisopropylamide, and organic bases such as triethylamine, 1,4-diazabicyclo[2.2.2]octane and 1,8-diazabicyclo[5.4.0]-7-undecene.

The amount of the base used in the reaction is usually 1 to 10 mol relative to 1 mol of the compound (o).

The amount of the compound (s) used in the reaction is usually 1 to 10 mol relative to 1 mol of the compound (o).

The reaction temperature is usually in a range of −20 to 100° C., and the reaction time is usually 1 to 24 hours.

After completion of the reaction, the compound (I-10) can be isolated by post-treatment, for example, by pouring a reaction mixture into water and extracting the resulting mixture with an organic solvent followed by concentration. The isolated compound (I-10) can be further purified by chromatography, recrystallization, or the like, if necessary.

Production Process 12

Among the compounds of the present invention, a compound (I-11) that is a compound of the formula (I) wherein n is 1 or 2 can be produced, for example, by oxidizing a compound (I-10) as follows:

$$\underset{(I\text{-}10)}{R^1\underset{R^2\ R^{3\text{-}2}}{\bigvee}S\diagdown\diagdown_{R^4}} \longrightarrow \underset{(I\text{-}11)}{R^1\underset{R^2\ R^{3\text{-}2}}{\bigvee}\overset{(O)_{n'}}{S}\diagdown\diagdown_{R^4}}$$

wherein $R^1$, $R^2$, $R^{3\text{-}2}$ and $R^4$ are as defined above, and n' represents 1 or 2.

The reaction is usually carried out in a solvent in the presence of an oxidizing agent.

Examples of a solvent used in the reaction include alcohols such as methanol and ethanol, halogenated hydrocarbons such as dichloromethane and chloroform, aromatic hydrocarbons such as toluene and xylene, aliphatic carboxylic acids such as acetic acid and trifluoroacetic acid, water and a mixture thereof.

Examples of a oxidant used in the reaction include organic peroxides such as peracetic acid, trifluoroperacetic acid and m-chloroperbenzoic acid, halogen molecules such as chlorine and bromine, halogen-containing imides such as N-chlorosuccinimide, halides such as perchloric acid (or its salt) and periodic acid (or its salt), permanganates such as potassium permanganate, chromates such as potassium chromate, and hydrogen peroxide.

The amount of the oxidizing agent used in the reaction is usually 1 to 10 mol relative to 1 mol of the compound (I-10).

The reaction temperature is usually in a range of −50 to 200° C., and the reaction time is usually 1 to 72 hours.

After completion of the reaction, the compound (I-11) can be isolated by post-treatment, for example, by pouring a reaction mixture into water and extracting the resulting mixture with an organic solvent followed by concentration. The isolated compound (I-11) can be further purified by chromatography, recrystallization, or the like, if necessary.

Next, a process for production of intermediates used for producing the compound of the present invention is explained by reference to Reference production processes.

Reference Production Process 1

The compound (g) can be produced by hydrolyzing a compound (I-6) as follows:

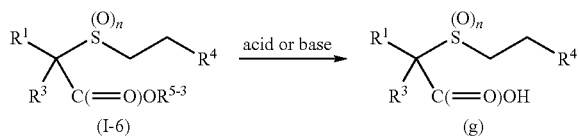

wherein $R^1$, $R^3$, $R^4$ and n are as defined above, and $R^{5-3}$ represents a methyl group or an ethyl group.

The reaction is usually carried out in an organic solvent in the presence of an acid or a base, and water.

Examples of an organic solvent used in the reaction include alcohols such as methanol and ethanol, ethers such as diethyl ether and tetrahydrofuran, organic sulfurs such as dimethyl sulfoxide and sulfolane, halogenated hydrocarbons such as chloroform, 1,2-dichloroethane and chlorobenzene, aromatic hydrocarbons such as toluene and xylene, aliphatic carboxylic acids such as formic acid and acetic acid, and a mixture thereof.

Examples of a base used in the reaction include inorganic bases such as sodium hydroxide and potassium hydroxide.

Examples of an acid used in the reaction include inorganic acids such as hydrochloric acid and sulfuric acid.

The amount of the acid or base used in the reaction is usually 1 to 10 mol relative to 1 mol of the compound (I-6).

The reaction temperature is usually in a range of −20 to 100° C., and the reaction time is usually 1 to 24 hours.

After completion of the reaction, the compound (g) can be isolated by post-treatment, for example, by adding water and/or an acid to a reaction mixture if necessary, and extracting the resulting mixture with an organic solvent followed by concentration. The isolated compound (g) can be further purified by column chromatography, recrystallization or the like, if necessary.

Reference Production Process 2

Among the compounds (d), a compound (d-1) that is a compound (d) wherein $R^{3-2}$ is a C1-C4 alkyl group can be produced, for example, by reacting the compound (a) with the compound (k) as follows:

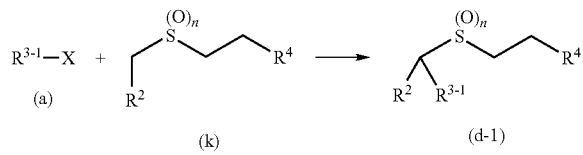

wherein $R^2$, $R^4$, $R^{3-1}$, n and X are as defined above.

The reaction is usually carried out in a solvent in the presence of a base.

Examples of a solvent used in the reaction include acid amides such as N,N-dimethylformamide, ethers such as diethyl ether and tetrahydrofuran, organic sulfurs such as dimethyl sulfoxide and sulfolane, halogenated hydrocarbons such as chloroform, 1,2-dichloroethane and chlorobenzene, aromatic hydrocarbons such as toluene and xylene, water and a mixture thereof.

Examples of a base used in the reaction include inorganic bases such as sodium hydride, sodium hydroxide, potassium hydroxide and potassium carbonate, alkali metal alkoxides such as sodium methoxide and potassium tert-butoxide, alkali metal amides such as lithium diisopropylamide, and organic bases such as triethylamine, 1,4-diazabicyclo[2.2.2]octane and 1,8-diazabicyclo[5.4.0]-7-undecene.

The amount of the base used in the reaction is usually 1 to 10 mol relative to 1 mol of the compound (k).

The amount of the compound (a) used in the reaction is usually 1 to 10 mol relative to 1 mol of the compound (k).

The reaction temperature is usually in a range of −20 to 100° C., and the reaction time is usually 1 to 24 hours. After completion of the reaction, the compound (d-1) can be isolated by post-treatment, for example, by pouring a reaction mixture into water and extracting the resulting Mixture with an organic solvent followed by concentration. The isolated compound (d-1) can be further purified by column chromatography, recrystallization or the like, if necessary.

Reference Production Process 3

Among the compounds (k), a compound (k-1) that is a compound (k) wherein n is 0 and a compound (k-2) that is a compound (k) wherein n is 1 or 2 can be produced by the following scheme:

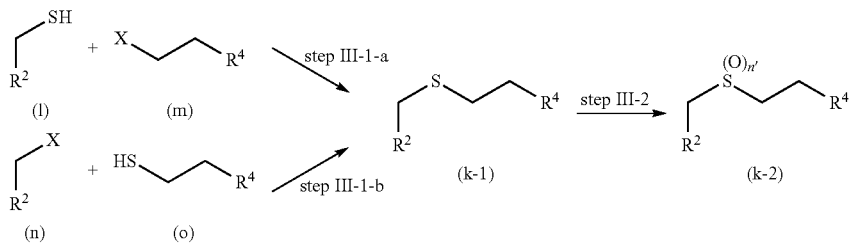

wherein $R^2$, $R^4$, X and n' are as defined above.

Step III-1-a:

The compound (k-1) can be produced, for example, by reacting the compound (l) with the compound (m).

The reaction is usually carried out in a solvent in the presence of a base.

Examples of a solvent used in the reaction include acid amides such as N,N-dimethylformamide, ethers such as diethyl ether and tetrahydrofuran, organic sulfurs such as dimethyl sulfoxide and sulfolane, halogenated hydrocarbons such as chloroform, 1,2-dichloroethane and chlorobenzene, aromatic hydrocarbons such as toluene and xylene, water and a mixture thereof.

Examples of a base used in the reaction include inorganic bases such as sodium hydride, sodium hydroxide, potassium hydroxide and potassium carbonate, alkali metal alkoxides such as sodium methoxide and potassium tert-butoxide, alkali metal amides such as lithium diisopropylamide, and organic bases such as triethylamine, 1,4-diazabicyclo[2.2.2]octane and 1,8-diazabicyclo[5.4.0]-7-undecene.

The amount of the base used in the reaction is usually 1 to 10 mol relative to 1 mol of the compound (l).

The amount of the compound (m) used in the reaction is usually 1 to 10 mol relative to 1 mol of the compound (l).

The reaction temperature is usually in a range of −20 to 100° C., and the reaction time is usually 1 to 24 hours.

After completion of the reaction, the compound (k-1) can be isolated by post-treatment, for example, by pouring a reaction mixture into water and extracting the resulting mixture with an organic solvent followed by concentration. The isolated compound (k-1) can be further purified by column chromatography, recrystallization or the like, if necessary.

Step III-1-b:

The compound (k-1) can also be produced, for example, by reacting the compound (n) with the compound (o).

The reaction is usually carried out in a solvent in the presence of a base.

Examples of a solvent used in the reaction include acid amides such as N,N-dimethylformamide, ethers such as diethyl ether and tetrahydrofuran, organic sulfurs such as dimethyl sulfoxide and sulfolane, halogenated hydrocarbons such as chloroform, 1,2-dichloroethane and chlorobenzene, aromatic hydrocarbons such as toluene and xylene, water and a mixture thereof.

Examples of a base used in the reaction include inorganic bases such as sodium hydride, sodium hydroxide, potassium hydroxide and potassium carbonate, alkali metal alkoxides such as sodium methoxide and potassium tert-butoxide, alkali metal amides such as lithium diisopropylamide, and organic bases such as triethylamine, 1,4-diazabicyclo[2.2.2]octane and 1,8-diazabicyclo[5.4.0]-7-undecene.

The amount of the base used in the reaction is usually 1 to 10 mol relative to 1 mol of the compound (o).

The amount of the compound (n) used in the reaction is usually 1 to 10 mol relative to 1 mol of the compound (o).

The reaction temperature is usually in a range of −20 to 100° C., and the reaction time is usually 1 to 24 hours.

After completion of the reaction, the compound (k-1) can be isolated by post-treatment, for example, by pouring a reaction mixture into water and extracting the resulting mixture with an organic solvent followed by concentration. The isolated compound (k-1) can be further purified by column chromatography, recrystallization or the like, if necessary.

Step III-2:

The compound (k-2) can be produced, for example, by oxidizing the compound (k-1).

The reaction is usually carried out in a solvent in the presence of an oxidizing agent.

Examples of a solvent used in the reaction include alcohols such as methanol and ethanol, halogenated hydrocarbons such as dichloromethane and chloroform, aromatic hydrocarbons such as toluene and xylene, aliphatic carboxylic acids such as acetic acid and trifluoroacetic acid, water and a mixture thereof.

Examples of an oxidizing agent used in the reaction include organic peroxides such as peracetic acid, trifluoroperacetic acid and m-chloroperbenzoic acid, halogen molecules such as chlorine and bromine, halogen-containing imides such as N-chlorosuccinimide, halides such as perchloric acid (or its salt) and periodic acid (or its salt), permagnates such as potassium permanganate, chromates such as potassium chromate, and hydrogen peroxide.

The amount of the oxidizing agent used in the reaction is usually 1 to 10 mol relative to 1 mol of the compound (k-1).

The reaction temperature is usually in a range of −50 to 200° C., and the reaction time is usually 1 to 72 hours.

After completion of the reaction, the compound (k-2) can be isolated by post-treatment, for example, by pouring a reaction mixture into water and extracting the resulting mixture with an organic solvent followed by concentration. The isolated compound (k-2) can be further purified by column chromatography, recrystallization or the like, if necessary.

The above compound (o) and (r) each can be produced, for example, in accordance with a method described in The Journal of Organic Chemistry, 27 (1), p. 93-95 (1962) and HETEROCYCLES, 24 (5), p. 1331-1346 (1986).

The above compound (s) can be produced, for example, in accordance with a method described in The Journal of Organic Chemistry, 18, p. 1112-1116 (1953).

The above compounds (a), (c), (j), (m), (n) and (p) are known or can be produced in accordance with a known method.

Examples of harmful arthropods on which the compound of the present invention exhibits a controlling effect include harmful insects and harmful mites, and more specifically, the following arthropods.

Hemiptera:

Planthoppers (Delphacidae) such as small brown planthopper (*Laodelphax striatellus*), brown rice planthopper (*Nilaparvata lugens*), and white-backed rice planthopper (*Sogatella furcifera*); leafhoppers (Deltocephalidae) such as green rice leafhopper (*Nephotettix cincticeps*), green rice leafhopper (*Nephotettix virescens*), and tea green leafhopper (*Empoasca onukii*); aphids (Aphididae) such as cotton aphid (*Aphis gossypii*), green peach aphid (*Myzus persicae*), cabbage aphid (*Brevicoryne brassicae*), spiraea aphid (*Aphis spiraecola*), potato aphid (*Macrosiphum euphorbiae*), foxglove aphid (*Aulacorthum solani*), oat bird-cherry aphid (*Rhopalosiphum padi*), tropical citrus aphid (*Toxoptera citricidus*), and mealy plum aphid (*Hyalopterus pruni*); stink bugs (Pentatomidae) such as green stink bug (*Nezara antennata*), bean bug (*Riptortus clavatus*), rice bug (*Leptocorisa chinensis*), white spotted spined bug (*Eysarcoris parvus*), and stink bug (*Halyomorpha mista*); whiteflies (Aleyrodidae) such as greenhouse whitefly (*Trialeurodes vaporariorum*), sweetpotato whitefly (*Bemisia tabaci*), citrus whitefly (*Dialeurodes citri*), and citrus spiny white fly (*Aleurocanthus spiniferus*); scales (Coccidae) such as Calfornia red scale (*Aonidiella aurantii*), San Jose scale (*Comstockaspis perniciosa*), citrus north scale (*Unaspis citri*), red wax scale (*Ceroplastes rubens*), cottonycushion scale (*Icerya purchase*), Japanese mealybug (*Planococcus kraunhiae*), Cosmstock mealybug (*Pseudococcus longispinis*), and white peach scale (*Pseudaulacaspis pentagona*); lace bugs (Tingidae); cimices such as *Cimex lectularius*; psyllids (Psyllidae), etc.;

Lepidoptera:

Pyralid moths (Pyralidae) such as rice stem borer (*Chilo suppressalis*), yellow rice borer (*Tryporyza incertulas*), rice leafroller (*Cnaphalocrocis medinalis*), cotton leafroller (*Notarcha derogate*), Indian meal moth (*Plodia interpunctella*), *Maruca testulalis*, cabbage webworm (*Hellula undalis*), and bluegrass webworm (*Pediasia teterrellus*); owlet moths (Noctuidae) such as common cutworm (*Spodoptera litura*), beet armyworm (*Spodoptera exigua*), armyworm (*Pseudaletia separate*), cabbage armywatin (*Mamestra brassicae*), black cutworm (*Agrotis ipsilon*), beet semi-looper (*Plusia nigrisigna*), *Thoricoplusia*spp., *Heliothis*spp., and *Helicoverpa*spp.; white butterflies (Pieridae) such as common white (*Pieris rapae*); tortricid moths (Tortricidae) such as *Adoxophyes*spp., oriental fruit moth (*Grapholita molesta*), soybean pod borer (*Leguminivora glycinivorella*), azuki bean podworm (*Matsumuraeses azukivora*), summer fruit tortrix (*Adoxophyes orana fasciata*), smaller tea tortrix (*Adoxo-*

*phyes* sp.), oriental tea tortrix (*Homona magnanima*), apple tortrix (*Archips fuscocupreanus*), and codling moth (*Cydia pomonella*); leafblotch miners (Gracillariidae) such as tea leafroller (*Caloptilia theivora*), and apple leafminer (*Phyllonorycter ringoneella*); Carposinidae such as peach fruit moth (*Carposina niponensis*); lyonetiid moths (Lyonetiidae) such as *Lyonetia* spp.; tussock moths (Lymantriidae) such as *Lymantria* spp., and *Euproctis* spp.; yponomeutid moths (Yponomeutidae) such as diamondback (*Plutella xylostella*); gelechiid moths (Gelechiidae) such as pink bollworm (*Pectinophora gossypiella*), and potato tubeworm (*Phthorimaea operculella*); tiger moths and allies (Arctiidae) such as fall webworm (*Hyphantria cunea*); tineid moths (Tineidae) such as casemaking clothes moth (*Tinea translucens*), and webbing clothes moth (*Tineola bisselliella*), etc.;

Thysanoptera:

Yellow citrus thrips (*Frankliniella occidentalis*), melon thrips (*Thrips palmi*), yellow tea thrips (*Scirtothrips dorsalis*), onion thrips (*Thrips tabaci*), flower thrips (*Frankliniella intonsa*), etc.;

Diptera:

Culices (Calicidae) such as common mosquito (*Culex pipiens pallens*), *Culex tritaeniorhynchus*, and Southern house mosquito (*Culex quinquefasciatus*); *Aedes* spp. such as yellow fever mosquito (*Aedes aegypti*), and Asian tiger mosquito (*Aedes albopictus*); *Anopheles* spp. such as *Anopheles sinensis*; Chironomidae; Houseflies (Muscidae) such as housefly (*Musca domestica*), and false stable fly (*Muscina stabulans*); blow flies (Calliphoridae); flesh flies (Sarcophagidae); little house flies (Fanniidae); anthomyiid flies (Anthomyiidae) such as seedcorn maggot (*Delia platura*), and onion maggot (*Delia antique*); leafminer flies (Agromyzidae) such as rice leafminer (*Agromyza oryzae*), rice leafminer (*Hydrellia griseola*), tomato leafminer (*Liriomyza sativae*), legume leafminer (*Liriomyza trifolii*), and garden pea leafminer (*Chromatomyia horticola*); gout flies (Chloropidae) such as rice stem maggot (*Chlorops oryzae*); fruit flies (Tephritidae) such as melon fly (*Dacus cucurbitae*), and Meditteranean fruit fly (*Ceratitis capitata*); drosophila flies (Drosophilidae); humpbacked flies (Phoridae) such as *Megaselia spiracularis*; Psychodidae such as *Clogmia albipunctata*; Simuliidae; Tabanidae such as horsefly (*Tabanus trigonus*); stable flies (*Stomoxys cakitrans*), etc.;

Coleoptera:

Corn root worms (*Diabrotica* spp.) such as Western corn root worm (*Diabrotica virgifera virgifera*), and Southern corn root worm (*Diabrotica undecimpunctata howardi*); scarabs (Scarabaeidae) such as cupreous chafer (*Anomala cuprea*), soybean beetle (*Anomala rufocuprea*), and Japanese beetle (*Popillia japonica*); weevils (Curculionidae) such as maize weevil (*Sitophilus zeamais*), rice water weevil (*Lissorhoptrus oryzophilus*), azuki bean weevil (*Callosobruchus chinensis*), rice curculio (*Echinocnemus squameus*), boll weevil (*Anthonomus grandis*), and hunting billbug (*Sphenophorus venatus*); darkling beetles (Tenebrionidae) such as yellow mealworm (*Tenebrio molitor*), and red flour beetle (*Tribolium castaneum*); leaf beetles (Chrysomelidae) such as rice leaf beetle (*Oulema oryzae*), cucurbit leaf beetle (*Aulacophora femoralis*), striped flea beetle (*Phyllotreta striolata*), and Colorado beetle (*Leptinotarsa decemlineata*); dermestid beetles (Dermestidae) such as varied carper beetle (*Anthrenus verbasci*), and hide beetle (*Dermestes maculates*); deathwatch beetles (Anobiidae) such as cigarette beetle (*Lasioderma serricorne*); Epilachna such as twenty-eight-spotted ladybird (*Epilachna vigintioctopunctata*); bark beetles (Scolytidae) such as powder post beetle (*Lyctus brunneus*), and pine shoot beetle (*Tomicus piniperda*); false powderpost beetles (Bostrichidae); spider beetles (Ptinidae); longhorn beetles (Cerambycidae) such as white-spotted longicorn beetle (*Anoplophora malasiaca*); click beetles (*Agriotes* spp.); *Paederus fuscipes*, etc.;

Orthoptera:

Asiatic locust (*Locusta migratoria*), African mole cricket (*Gryllotalpa africana*), rice grasshopper (*Oxya yezoensis*), rice grasshopper (*Oxya japonica*), Grylloidea, etc.;

Shiphonaptera:

Cat flea (*Ctenocephalides felis*), dog flea (*Ctenocephalides canis*), human flea (*Pulex irritans*), oriental rat flea (*Xenopsylla cheopis*), etc.;

Anoplura:

Human body louse (*Pediculus humanus corporis*), crab louse (*Phthirus pubis*), short-nosed cattle louse (*Haematopinus eurysternus*), sheep louse (*Dalmalinia ovis*), hog louse (*Haematopinus suis*), etc.;

Hymenoptera:

Ants (Formicidae) such as *Monomorium pharaosis, Formica fusca japonica*, black house ant (*Ochetellus glaber*), *Pristomyrmex pungens, Pheidole noda*, leaf-cutting ant (*Acromyrmex* spp.), and fire ant (*Solenopsis* spp.); hornets (Vespidae); bethylid wasps (Betylidae); sawflies (Tenthredinidae) such as Cabbage sawfly (*Athalia rosae*), and *Athalia japonica*, etc.;

Blattodea:

Cockroaches (Blattariae) such as German cockroach (*Blattella germanica*), smokybrown cockroach (*Periplaneta fidiginosa*), American cockroach (*Periplaneta americana*), *Periplaneta brunnea*, and oriental cockroach (*Blatta orientalis*); termites (Termitidae) such as subterranean termites such as Japanese subterranean termite (*Reticulitermes speratus*), Formosan subterranean termite (*Coptotermes formosanus*), western drywood teimite (*Incisitermes minor*), Daikoku drywood termite (*Cryptotermes domesticus*), *Odontotermes formosanus, Neotermes koshunesis, Glyptotermes satsumesis, Glyptotermes nakajimai, Glyptotermes fuscus, Glyptotermes kodamai, Glyptotermes kushimensis*, Japanese dampwood termite (*Hodotermopsis japonica*), *Coptotermes guangzhoensis, Reticulitermes miyatakei, Reticulitermes flavipes amamianus, Reticulitermes kanmonensis* (*Reticulitermes* sp.), *Nasutitermes takasagoensis, Pericapritermes nitobei, Sinocapritermes mushae*, etc.;

Acarina:

Spider mites (Tetranychidae) such as two-spotted spider mite (*Tetranychus urticae*), Kanzawa spider mite (*Tetranychus kanzawai*), citrus red mite (*Panonychus citri*), European red mite (*Panonychus ulmi*), and *Oligonychus* spp.; eriophyid mites (Eriophyidae) such as pink citrus rust mite (*Aculops pelekassi*), *Phyllocoptruta citri*, tomato rust mite (*Aculops lycopersici*), purple tea mite (*Calacarus carinatus*), pink tea rust mite (*Acaphylla theavagran*), *Eriophyes chibaensis*, and apple rust mite (*Aculus schlechtendali*); tarosonemid mites (Tarsonemidae) such as broad mite (*Polyphagotarsonemus latus*); false spider mites (Tenuipalpidae) such as *Brevipalpus phenicis*; Tuckerellidae; ticks (Ixodidae) such as *Haemaphysalis longicornis, Haemaphysalis flava*, American dog tick (*Dermacentor variabilis*), *Haemaphysalis flava, Dermacentor taiwanicus*, American dog tick (*Dermacentor variabilis*), *Ixodes ovatus, Ixodes persulcatus*, black legged tick (*Ixodes scapularis*), lone star tick (Amblyomma americanum), *Boophilus microplus*, and *Rhipicephalus sanguineus*; Psoroptidae such as ear mite (*Otodectes cynotis*); itch mites (Sarcoptidae) such as *Sarcoptes scabiei*; folicle mites (Demodicidae) such as dog folicle mite (*Demodex canis*); acarid mites (Acaridae) such as mold mite (*Tyrophagus putrescentiae*), and *Tyrophagus similis*; house dust mites (Pyroglyphidae)

such as *Dermatophagoides farinae*, and *Dermatophagoides ptrenyssnus*; cheyletide mites (Cheyletidae) such as *Cheyletus eruditus, Cheyletus malaccensis*, and *Cheyletus moorei*; parasitoid mites (Dermanyssidae) such as tropical rat mite (*Ornithonyssus bacoti*), northern fowl mite (*Ornithonyssus sylviarum*), and poultry red mite (*Dermanyssus gallinae*); chiggers (Trombiculidae) such as *Leptotrombidium akamushi*; spiders (Araneae) such as Japanese foliage spider (*Chiracanthium japonicum*), redback spider (*Latrodectus hasseltii*), etc.;

Chilopoda: *Thereuonema hilgendorfi, Scolopendra subspinipes*, etc.;

Diplopoda: garden millipede (*Oxidus gracilis*), *Nedyopus tambanus*, etc.;

Isopoda: common pill bug (*Armadillidium vulgare*), etc.;

Gastropoda: *Limax marginatus, Limax flavus*, etc.

Although the pesticidal composition of the present invention may be the compound of the present invention itself, the pesticidal composition of the present invention usually comprises the compound of the present invention in combination with a solid carrier, a liquid carrier and/or a gaseous carrier, and if necessary, a surfactant or other pharmaceutical additives and takes the foam of an emulsion, an oil, a shampoo formulation, a flowable formulation, a powder, a wettable powder, a granule, a paste, a microcapsule, a foam formulation, an aerosol, a carbon dioxide gas preparation, a tablet, a resin preparation or the like. The pesticidal composition of the present invention may be processed into a poison bait, a mosquito coil, an electric mosquito mat, a smoking agent, a fumigant or a sheet, and then be used.

The pesticidal composition of the present invention usually contains 0.1 to 95% by weight of the compound of the present invention.

Examples of the solid carrier include finely-divided powder or granules of clay (e.g., kaolin clay, diatomaceous earth, bentonite, Fubasami clay, acid clay, etc.), synthetic hydrated silicon oxide, talc, ceramics, other inorganic minerals (e.g., sericite, quartz, sulfur, activated carbon, calcium carbonate, hydrated silica, etc.), chemical fertilizers (e.g., ammonium sulfate, ammonium phosphate, ammonium nitrate, ammonium chloride, urea, etc.) and the like.

Examples of the liquid carrier include aromatic or aliphatic hydrocarbons (e.g., xylene, toluene, alkylnaphthalene, phenylxylylethane, kerosene, light oil, hexane, cyclohexane, etc.), halogenated hydrocarbons (e.g., chlorobenzene, dichloromethane, dichloroethane, trichloroethane, etc.), alcohols (e.g., methanol, ethanol, isopropyl alcohol, butanol, hexanol, ethylene glycol, etc.), ethers (e.g., diethyl ether, ethylene glycol dimethyl ether, diethylene glycol monomethyl ether, diethylene glycol monoethyl ether, propylene glycol monomethyl ether, tetrahydrofuran, dioxane, etc.), esters (e.g., ethyl acetate, butyl acetate, etc.), ketones (e.g., acetone, methyl ethyl ketone, methyl isobutyl ketone, cyclohexanone etc.), nitriles (e.g., acetonitrile, isobutyronitrile etc.), sulfoxides (e.g., dimethyl sulfoxide etc.), acid amides (e.g., N,N-dimethylformamide, N,N-dimethylacetamide etc.), pyrrolidones (e.g., N-methyl-2-pyrrolidone, N-octyl-2-pyrrolidone, etc.), propylene carbonate, ethyl lactate, 1,3-dimethyl-2-imidazolidinone, vegetable oils (e.g., soybean oil, cottonseed oil etc.), vegetable essential oils (e.g., orange oil, hyssop oil, lemon oil, etc.), water and the like.

Examples of the gaseous carrier include butane gas, chlorofluorocarbon, LPG (liquefied petroleum gas), dimethyl ether, carbon dioxide gas and the like.

Examples of the surfactant include alkyl sulfate salts, alkyl sulfonate salts, alkylaryl sulfonate salts, alkyl aryl ethers and their polyoxyethylated derivatives, polyethylene glycol ethers, polyhydric alcohol esters, and sugar alcohol derivatives.

Examples of other pharmaceutical additives include a binder, a dispersant, a stabilizer and the like, and specific examples thereof include casein, gelatin, polysaccharides (e.g., starch, gum arabic, cellulose derivatives, alginic acid, etc.), lignin derivatives, bentonite, saccharides, synthetic water-soluble polymers (e.g., polyvinyl alcohol, polyvinylpyrrolidone, polyacrylic acid, etc.), PAP (isopropyl acid phosphate), BHT (2,6-di-tert-butyl-4-methylphenol), BHA (a mixture of 2-tert-butyl-4-methoxyphenol and 3-tert-butyl-4-methoxyphenol), vegetable oils, mineral oils, fatty acids, and fatty acid esters.

Examples of a base material for a resin preparation include vinyl chloride polymers, polyurethane and the like. To the base material, if necessary, a plasticizer such as phthalate (e.g., dimethyl phthalate, dioctyl phthalate, etc.), adipate, stearic acid or the like may be added. The resin preparation is obtained by kneading the compound of the present invention into the base material using a conventional kneading apparatus, followed by molding such as injection molding, extrusion molding, press molding or the like. The resulting resin preparation may be formed into the shape of a plate, a film, a tape, a net, a string or the like via a further step of molding, cutting, or the like, if necessary. These resin preparations may be used, for example, in the form of an animal collar, an animal ear tag, a sheet preparation, a lead, or a horticultural post.

Examples of a base material of a poison bait includes cereal powder, vegetable oil, sugar, crystalline cellulose and the like. To the base material, if necessary, an antioxidant such as dibutylhydroxytoluene or nordihydroguaiaretic acid, a preservative such as dehydroacetic acid, an agent for preventing children or pets from erroneously eating such as hot pepper powder, a pest-attractive perfume such as cheese perfume, onion perfume or peanut oil or the like may be added.

The pesticidal composition of the present invention can be applied, for example, to harmful arthropods directly and/or a place where harmful arthropods inhabit (e.g., plants, animals, soil, etc.).

When the pesticidal composition of the present invention is used for controlling pests in agriculture and forestry, the application amount is usually 1 to 10,000 g/ha, preferably 10 to 500 g/ha of the active ingredient. When the pesticidal composition of the present invention is the form of an emulsion, a wettable powder, a flowable formulation, or a microcapsule, it is usually used after dilution with water so as to have an active ingredient concentration of 0.01 to 1,000 ppm. When the pesticidal composition of the present invention is the form of a powder or a granule, it is usually used as it is. The pesticidal composition of the present invention as it is or as a dilution may be sprayed directly to plants to be protected from harmful arthropods. Alternatively, soil can be treated with the pesticidal composition of the present invention as it is or as a dilution to control harmful arthropods living in the soil. Seedbeds before planting or planting holes or plant feet in planting can be also treated with the pesticidal composition of the present invention as it is or as a dilution. Further, a sheet preparation of the pesticidal composition of the present invention may be applied by winding around plants, disposing in the vicinity of plants, laying on the soil surface at the plant feet, or the like.

The pesticidal composition of the present invention can be used in crop lands such as cultivated lands, paddy fields, lawns and orchards. The pesticidal composition of the present invention may control harmful arthropods in a crop land without causing drug damage to crop plants cultivated in the crop land.

Examples of such crop plants include

Agricultural crops: corn, rice, wheat, barley, rye, oat, sorghum, cotton, soybean, peanut, sarrazin, sugar beet, rapeseed, sunflower, sugar cane, tobacco etc.;

Vegetables: Solanaceae vegetables (eggplant, tomato, green pepper, hot pepper, potato etc.), Cucurbitaceae vegetables (cucumber, pumpkin, zucchini, watermelon, melon etc.), Cruciferae vegetables (Japanese radish, turnip, horseradish, kohlrabi, Chinese cabbage, cabbage, brown mustard, broccoli, cauliflower etc.), Compositae vegetables (burdock, garland chrysanthemum, artichoke, lettuce etc.), Liliaceae vegetables (Welsh onion, onion, garlic, asparagus etc.), Umbelliferae vegetables (carrot, parsley, celery, parsnip etc.), Chenopodiaceae vegetables (spinach, Swiss chard etc.), Labiatae vegetables (Japanese basil, mint, basil etc.), strawberry, sweat potato, yam, aroid etc.;

Flowers and ornamental plants;

Foliage plant;

Fruit trees: pomaceous fruits (apple, common pear, Japanese pear, Chinese quince, quince etc.), stone fleshy fruits (peach, plum, nectarine, Japanese plum, cherry, apricot, prune etc.), citrus plants (Satsuma mandarin, orange, lemon, lime, grapefruit etc.), nuts (chestnut, walnut, hazel nut, almond, pistachio, cashew nut, *macadamia* nut etc.), berry fruits (blueberry, cranberry, blackberry, raspberry etc.), grape, persimmon, olive, loquat, banana, coffee, date, coconut etc.;

Trees other than fruit trees: tea, mulberry, flowering trees and shrubs, street trees (ash tree, birch, dogwood, eucalyptus, ginkgo, lilac, maple tree, oak, poplar, cercis, Chinese sweet gum, plane tree, zelkova, Japanese arborvitae, fir tree, Japanese hemlock, needle juniper, pine, spruce, yew) etc.

The aforementioned crop plants include those to which resistance to a herbicide, such as an HPPD inhibitor such as isoxaflutole, an ALS inhibitor such as imazethapyr or thifensulfuron-methyl, an EPSP synthesizing enzyme inhibitor, a glutamine synthesizing enzyme inhibitor, an acetyl CoA carboxylase inhibitor or bromoxynil, has been imparted by a classical breeding method, a genetic engineering technique or the like.

Examples of the crop plant to which resistance to a herbicide has been imparted by a classical breeding method include Clearfield (registered trademark) canola which is resistant to an imidazolinone herbicide such as imazethapyr, STS soybean which is resistant to a sulfonylurea ALS inhibitor herbicide such as thifensulfuron-methyl, and the like. Examples of the crop plant to which resistance to an acetyl CoA carboxylase inhibitor such as a trioxime or aryloxyphenoxypropionic acid herbicide has been imparted by a classical breeding method include SR corn and the like. For example, crop plants to which resistance to acetyl CoA carboxylase inhibitors has been imparted are found in Proc. Natl. Acad. Sci. USA 1990, 87, p. 7175-7179. In addition, a mutant acetyl CoA carboxylase which is resistant to an acetyl CoA carboxylase inhibitor is known, for example, in Weed Science 53: p. 728-746, 2005. When a gene encoding the mutant acetyl CoA carboxylase is introduced into a crop plant by a genetic engineering technique or when a mutation related to impartation of resistance is introduced into a gene encoding acetyl CoA carboxylase of a crop plant, a crop plant having the resistance to an acetyl CoA carboxylase inhibitor can be produced. Further, nucleic acids for introduction of a base substitution mutation can be introduced into the cell of a crop plant by chimeraplasty (see, Gura T. 1999, Repairing the Genome's Spelling Mistakes, Science 285: 316-318) to induce a site-directed amino acid mutation in the gene which is targeted by an acetyl CoA carboxylase inhibitor or herbicide of the crop plant, and thereby a crop plant resistant to an acetyl CoA carboxylase inhibitor or herbicide can be produced.

Examples of the crop plant to which resistance to a herbicide has been imparted by a genetic engineering technique include corn cultivars having resistance to glyphosate or glufosinate. Some of such corn cultivars are sold under the trade name of RoundupReady (registered trademark), LibertyLink (registered trademark), and the like.

The aforementioned crop plants include those to which ability to produce an insecticidal toxin, for example a selective toxin which is known to be produced by *Bacillus*, has been imparted by a genetic engineering technique.

Examples of the insecticidal toxin which is produced by such a genetically engineered plant include insecticidal proteins derived from *Bacillus cereus* and *Bacillus popilliae*; δ-endotoxins derived from *Bacillus thuringiensis*, such as Cry1Ab, Cry1Ac, Cry1F, Cry1Fa2, Cry2Ab, Cry3A, Cry3Bb1 and Cry9C; insecticidal proteins derived from *Bacillus thuringiensis*, such as VIP 1, VIP 2, VIP 3 and VIP 3A; insecticidal proteins derived from nematodes; toxins produced by animals such as scorpion toxins, spider toxins, bee toxins and insect-specific nerve toxins; fungal toxins; plant lectin; agglutinin; protease inhibitors such as trypsin inhibitors, serine protease inhibitors, patatin, cystatin, and papain inhibitors; ribosome-inactivating proteins (RIP) such as ricin, corn-RIP, abrin, saporin, and briodin; steroid metabolizing enzymes such as 3-hydroxysteroid oxidase, ecdysteroid-UDP-glucosyltransferase, and cholesterol oxidase; ecdysone inhibitors; HMG-COA reductase; ion channel inhibitors such as sodium channel inhibitors and calcium channel inhibitors; juvenile hormone esterase; diuretic hormone receptors; stilbene synthase; bibenzyl syntase; chitinase; and glucanase.

The insecticidal toxin which is produced by such a genetically engineered plant also includes hybrid toxins of different insecticidal proteins, for example, δ-endotoxins such as Cry1Ab, Cry1Ac, Cry1F, Cry1Fa2, Cry2Ab, Cry3A, Cry3Bb1 and Cry9C and insecticidal proteins such as VIP 1, VIP 2, VIP 3 and VIP 3A, and toxins in which a part of amino acids constituting an insecticidal protein is deleted or modified. The hybrid toxin is made by combining different domains of the insecticidal proteins by a genetic engineering technique. An example of the toxin in which a part of amino acids constituting an insecticidal protein is deleted includes Cry1Ab in which a part of amino acids is deleted. An example of the toxin in which a part of amino acids constituting an insecticidal protein is modified includes a toxin in which one or more of amino acids of a naturally occurring toxin are substituted.

The insecticidal toxin and the genetically engineered crop plant having the ability to produce the insecticidal toxin are described, for example, in EP-A-0 374 753, WO 93/07278, WO 95/34656, EP-A-0 427 529, EP-A-451878, WO 03/052073, and the like.

The genetically engineered crop plant having the ability to produce the insecticidal toxin particularly has resistance to attack by a coleopteran pest, dipteran pest or a lepidopteran pest.

Genetically engineered plants which have one or more pest-resistance genes and thereby produce one or more insecticidal toxins are also known, and some of them are commercially available. Examples of such genetically engineered plants include YieldGard (registered trademark) (a corn cultivar expressing Cry1Ab toxin), YieldGard Rootworm (registered trademark) (a corn cultivar expressing Cry3Bb1 toxin), YieldGard Plus (registered trademark) (a corn cultivar expressing Cry1Ab and Cry3Bb1 toxins), Heculex I (registered trademark) (a corn cultivar expressing Cry1Fa2 toxin and phosphinothricin N-acetyltransferase (PAT) for imparting resistance to gluphosinate), NuCOTN33B (registered trademark) (a cotton cultivar expressing Cry1Ac toxin), Bollgard I (registered trademark) (a cotton cultivar expressing Cry1Ac toxin), Bollgard II (registered trademark) (a cotton cultivar expressing Cry1Ac and Cry2Ab toxins), VIPCOT (registered trademark) (a cotton cultivar expressing VIP toxin), NewLeaf (registered trademark) (a potato cultivar expressing Cry3A toxin), NatureGard Agrisure GT Advantage (registered trademark) (GA21 glyphosate-resistance character), Agrisure CB Advantage (registered trademark) (Bt11 corn borer (CB) character), Protecta (registered trademark), and the like.

The aforementioned crop plants include those to which ability to produce an anti-pathogen substance has been imparted by a genetic engineering technique.

Examples of the anti-pathogen substance includes PR proteins (PRPs described in EP-A-0 392 225); ion channel inhibitors such as sodium channel inhibitors, and calcium channel inhibitors (e.g. KP1, KP4, KP6 toxins etc. produced by viruses); stilbene synthase; bibenzyl synthase; chitinase; glucanase; substances produced by microorganisms such as peptide antibiotics, heterocycle-containing antibiotics, and protein factors involved in plant disease-resistance (referred to as plant disease resistance genes and described in WO 03/000906); and the like. Such anti-pathogen substances and genetically engineered plants which produce the anti-pathogen substances are described in EP-A-0 392 225, WO 05/33818, EP-A-0 353 191, and the like.

When the pesticidal composition of the present invention is used for control of epidemic, the application amount is usually 0.001 to 10 mg/m$^3$ of the active ingredient for application to space, and 0.001 to 100 mg/m$^2$ of the active ingredient for application to a plane. The pesticidal composition in the form of an emulsion, a wettable powder or a flowable formulation is usually applied after dilution with water so as to contain usually 0.001 to 10,000 ppm of the active ingredient. The pesticidal composition in the form of an oil, an aerosol, a smoking agent or a poison bait is usually applied as it is.

When the pesticidal composition of the present invention is used for controlling external parasites of livestock such as a cow, a horse, a pig, a sheep, a goat and a chicken, or small animals such as a dog, a cat, a rat and a mouse, it can be applied to said animals by a known method in the veterinary filed. Specifically, when systemic control is intended, the pesticidal composition of the present invention is administered, for example, as a tablet, a mixture with feed, a suppository or an injection (e.g., intramuscularly, subcutaneously, intravenously, intraperitoneally, etc.). When non-systemic control is intended, a method of using the pesticidal composition of the present invention includes spraying, pour-on treatment or a spot-on treatment with the pesticidal composition in the form of an oil or an aqueous liquid, washing an animal with the pesticidal composition in the form of a shampoo formulation, and attachment of a collar or a ear tag made of the pesticidal composition in the form of a resin preparation to an animal. When administered to an animal, the amount of the compound of the present invention is usually in the range of 0.1 to 1,000 mg per 1 kg body weight of the animal.

The pesticidal composition of the present invention may be used in admixture or combination with other insecticides, nematocides, acaricides, fungicides, herbicides, plant growth regulators, synergists, fertilizers, soil conditioners, animal feed, and the like.

Examples of an active ingredient of such insecticide include (1) Organic Phosphorus Compounds:

acephate, aluminum phosphide, butathiofos, cadusafos, chlorethoxyfos, chlorfenvinphos, chlorpyrifos, chlorpyrifos-methyl, cyanophos (CYAP), diazinon, DCIP (dichlorodiisopropyl ether), dichlofenthion (ECP), dichlorvos (DDVP), dimethoate, dimethylvinphos, disulfoton, EPN, ethion, ethoprophos, etrimfos, fenthion (MPP), fenitrothion (MEP), fosthiazate, formothion, hydrogen phosphide, isofenphos, isoxathion, malathion, mesulfenfos, methidathion (DMTP), monocrotophos, naled (BRP), oxydeprofos (ESP), parathion, phosalone, phosmet (PMP), pirimiphos-methyl, pyridafenthion, quinalphos, phenthoate (PAP), profenofos, propaphos, prothiofos, pyraclorfos, salithion, sulprofos, tebupirimfos, temephos, tetrachlorvinphos, terbufos, thiometon, trichlorphon (DEP), vamidothion, phorate, cadusafos, and the like;

(2) Carbamate Compounds:

alanycarb, bendiocarb, benfuracarb, BPMC, carbaryl, carbofuran, carbosulfan, cloethocarb, ethiofencarb, fenobucarb, fenothiocarb, fenoxycarb, furathiocarb, isoprocarb (MIPC), metolcarb, methomyl, methiocarb, NAC, oxamyl, pirimicarb, propoxur (PHC), XMC, thiodicarb, xylylcarb, aldicarb, and the like;

(3) Synthetic Pyrethroid Compounds:

acrinathrin, allethrin, benfluthrin, beta-cyfluthrin, bifenthrin, cycloprothrin, cyfluthrin, cyhalothrin, cypermethrin, empenthrin, deltamethrin, esfenvalerate, ethofenprox, fenpropathrin, fenvalerate, flucythrinate, flufenoprox, flumethrin, fluvalinate, halfenprox, imiprothrin, permethrin, prallethrin, pyrethrins, resmethrin, sigma-cypermethrin, silafluofen, tefluthrin, tralomethrin, transfluthrin, tetramethrin, phenothrin, cyphenothrin, alpha-cypermethrin, zeta-cypermethrin, lambda-cyhalothrin, gamma-cyhalothrin, furamethrin, tau-fluvalinate, metofluthrin, 2,3,5,6-tetrafluoro-4-methylbenzyl 2,2-dimethyl-3-(1-propenyl)cyclopropanecarboxylate, 2,3,5,6-tetrafluoro-4-(methoxymethyl)benzyl 2,2-dimethyl-3-(2-methyl-1-propenyl)cyclopropanecarboxylate, 2,3,5,6-tetrafluoro-4-(methoxymethyl)benzyl 2,2-dimethyl-3-(2-cyano-1-propenyl)cyclopropanecarboxylate, 2,3,5,6-tetrafluoro-4-(methoxymethyl)benzyl 2,2,3,3-tetramethylcyclopropanecarboxylate, and the like;

(4) Nereistoxin Compounds:

cartap, bensultap, thiocyclam, monosultap, bisultap, and the like;

(5) Neonicotinoid Compounds:

imidacloprid, nitenpyram, acetamiprid, thiamethoxam, thiacloprid, dinotefuran, clothianidin, and the like;

(6) Benzoylurea Compounds:

chlorfluazuron, bistrifluoron, diafenthiuron, diflubenzuron, fluazuron, flucycloxuron, flufenoxuron, hexaflumuron, lufenuron, novaluron, noviflumuron, teflubenzuron, triflumuron, triazuron, and the like;

(7) Phenylpyrazole Compounds:

acetoprole, ethiprole, fipronil, vaniliprole, pyriprole, pyrafluprole, and the like;

(8) Bt Toxin Insecticides:

live spores derived from and crystal toxins produced from *Bacillus* thuringiesis and a mixture thereof;

(9) Hydrazine Compounds:

chromafenozide, halofenozide, methoxyfenozide, tebufenozide, and the like;

(10) Organic Chlorine Compounds:
aldrin, dieldrin, dienochlor, endosulfan, methoxychlor, and the like;
(11) Natural Insecticides:
machine oil, nicotine sulfate, and the like;
(12) Other Insecticides:
avermectin-B, bromopropylate, buprofezin, chlorphenapyr, cyromazine, D-D (1,3-dichloropropene), emamectin-benzoate, fenazaquin, flupyrazofos, hydroprene, methoprene, indoxacarb, metoxadiazone, milbemycin-A, pymetrozine, pyridalyl, pyriproxyfen, spinosad, sulfluramid, tolfenpyrad, triazamate, flubendiamide, lepimectin, arsenic acid, benclothiaz, calcium cyanamide, calcium polysulfide, chlordane, DDT, DSP, flufenerim, flonicamid, flurimfen, formetanate, metam-ammonium, metam-sodium, methyl bromide, potassium oleate, protrifenbute, spiromesifen, sulfur, metaflumizone, spirotetramat, pyrifluquinazone, spinetoram, chlorantraniliprole, tralopyril, a compound represented by the following formula (A):

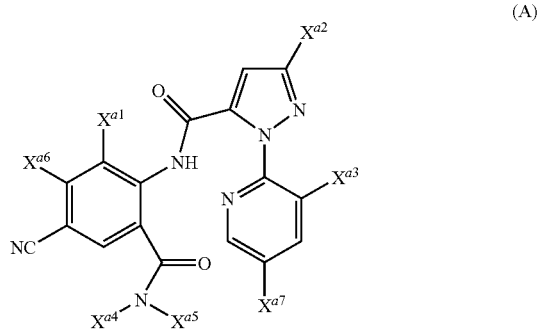

wherein $X^{a1}$ represents methyl, chlorine, bromine or fluorine, $X^{a2}$ represents fluorine, chlorine, bromine, C1-C4 haloalkyl or C1-C4 haloalkoxy, $X^{a3}$ represents fluorine, chlorine or bromine, $X^{a4}$ represents optionally substituted C1-C4 alkyl, optionally substituted C3-C4 alkenyl, optionally substituted C3-C4 alkynyl, optionally substituted C3-C5 cycloalkyl or hydrogen, $X^{a5}$ represents hydrogen or methyl, $X^{a6}$ represents hydrogen, fluorine or chlorine, and $X^{a7}$ represents hydrogen, fluorine or chlorine;
a compound represented by the following formula (B):

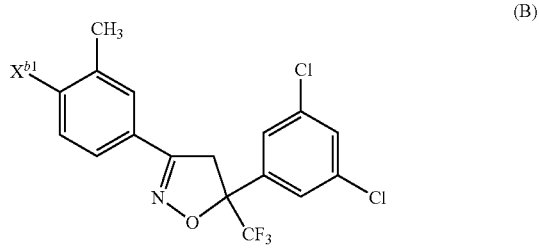

wherein $X^{b1}$ represents $X^{b2}$—NH—C(=O), $X^{b2}$—C(=O)—NH, $X^{b3}$—S(O), optionally substituted pyrrol-1-yl, optionally substituted imidazol-1-yl, optionally substituted pyrazol-1-yl, or optionally substituted 1,2,4-triazol-1-yl, $X^{b2}$ represents optionally substituted C1-C4 haloalkyl such as 2,2,2-trifluoroethyl or optionally substituted C3-C6 cycloalkyl such as cyclopropyl, and $X^{b3}$ represents optionally substituted C1-C4 alkyl such as methyl;

a compound represented by the following formula (C):

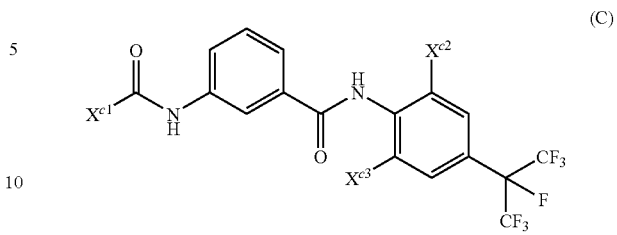

wherein $X^{c1}$ represents optionally substituted C1-C4 alkyl such as 3,3,3-trifluoropropyl, optionally substituted C1-C4 alkoxy such as 2,2,2-trichloroethoxy or optionally substituted phenyl such as phenyl, $X^{c2}$ represents methyl or trifluoromethylthio, and $X^{c3}$ represents methyl or halogen; and the like.

Examples of an active ingredient of the acaricide include acequinocyl, amitraz, benzoximate, bifenazate, bromopropylate, chinomethionat, chlorobenzilate, CPCBS (chlorfenson), clofentezine, cyflumetofen, kelthane (dicofol), etoxazole, fenbutatin oxide, fenothiocarb, fenpyroximate, fluacrypyrim, fluproxyfen, hexythiazox, propargite (BPPS), polynactins, pyridaben, pyrimidifen, tebufenpyrad, tetradifon, spirodiclofen, spiromesifen, spirotetramat, amidoflumet, cyenopyrafen, and the like.

Examples of the nematicide include DCIP, fosthiazate, levamisol hydrochloride, methylisothiocyanate, morantel tartarate, imicyafos, and the like.

Examples of an active ingredient of such fungicide include strobilurin compounds such as azoxystrobin; organophosphate compounds such as tolclofos-methyl; azole compounds such as triflumizole, pefurazoate and difenoconazole; fthalide, flutolanil, validamycin, probenazole, diclomezine, pencycuron, dazomet, kasugamycin, IBP, pyroquilon, oxolinic acid, tricyclazole, ferimzone, mepronil, EDDP, isoprothiolane, carpropamid, diclocymet, furametpyr, fludioxonil, procymidone and diethofencarb.

EXAMPLES

Hereinafter, the present invention will be explained in more detail by the following Production Examples, Formulation Examples and Test Examples, but the present invention is not limited to them.

First, Production Examples of the compound of the present invention is shown.

Production Example 1

To a solution of 5.0 g of 1,2-dichloro-1,1,2-trifluoro-4-iodobutane and 3.8 g of methyl (3,3,3-trifluoropropylsulfonyl)acetate in 100 ml of dimethyl sulfoxide was added 0.7 g of sodium hydride (60% in oil) at room temperature, and the mixture was stirred at the same temperature for 3 days. To the reaction mixture was added 10% hydrochloric acid, and then extracted with ethyl acetate. The organic layer was washed with a saturated sodium chloride aqueous solution, dried over anhydrous magnesium sulfate, and then concentrated under reduced pressure. The obtained residue was subjected to silica gel chromatography to obtain 1.50 g of methyl 5,6-dichloro-5,6,6-trifluoro-2-(3,3,3-trifluoropropylsulfonyl)hexanoate (hereinafter referred to as the present compound (1)).

The Present Compound (1):

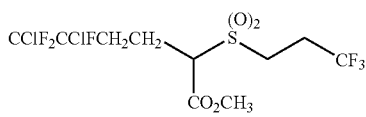

$^1$H-NMR (CDCl$_3$, TMS): δ (ppm) 3.90 (s, 3H), 3.88-3.98 (m, 1H), 3.38-3.54 (m, 2H), 2.23-2.78 (m, 6H).

Production Example 2

To a solution of 1.0 g of the present compound (1) in 30 ml of tetrahydrofuran was added 0.1 g of sodium hydride (60% in oil) at room temperature, and the mixture was stirred at the same temperature for 0.5 hours. To the mixture, 0.3 g of N-chlorosuccinimide was added at room temperature, and stirred for 16 hours. To the reaction mixture was added 10% hydrochloric acid, and then extracted with ethyl acetate. The organic layer was washed with a saturated sodium chloride aqueous solution, dried over anhydrous magnesium sulfate, and then concentrated under reduced pressure. The obtained residue was subjected to silica gel chromatography to obtain 0.85 g of methyl 2,5,6-trichloro-5,6,6-trifluoro-2-(3,3,3-trifluoropropylsulfonyl)hexanoate (hereinafter referred to as the present compound (2)).

The Present Compound (2):

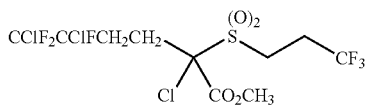

$^1$H-NMR (CDCl$_3$, TMS): δ (ppm) 3.97 (s, 3H), 3.59-3.88 (m, 2H), 2.38-3.08 (m, 6H).

Production Example 3

To a solution of 0.6 g of the present compound (2) in 30 ml of methanol was added 0.6 ml of ammonia (7M methanol solution) at room temperature. The mixture was stirred at the same temperature for 16 hours. The reaction mixture was concentrated under reduced pressure. The obtained residue was subjected to silica gel chromatography to obtain 0.40 g of 2,5,6-trichloro-5,6,6-trifluoro-2-(3,3,3-trifluoropropylsulfonyl)hexanamide (hereinafter referred to as the present compound (3)).

The Present Compound (3):

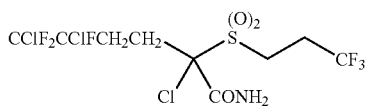

$^1$H-NMR (CDCl$_3$, TMS): δ (ppm) 6.86 (bs, 1H), 5.90 (bs, 1H), 3.34-3.78 (m, 2H), 2.40-3.09 (m, 6H).

Production Example 4

To a solution of 1.2 g of 1,4-dibromo-1,1,2,2-tetrafluorobutane and 1.0 g of methyl (3,3,3-trifluoropropylsulfonyl) acetate in 30 ml of dimethyl sulfoxide was added 0.2 g of sodium hydride (60% in oil) at room temperature. The mixture was stirred at the same temperature for 3 days. To the reaction mixture was added 10% hydrochloric acid, and then extracted with ethyl acetate. The organic layer was washed with a saturated sodium chloride aqueous solution, dried over anhydrous magnesium sulfate, and then concentrated under reduced pressure. The obtained residue was subjected to silica gel chromatography to obtain 0.50 g of methyl 6-bromo-5,5,6,6-tetrafluoro-2-(3,3,3-trifluoropropylsulfonyl)hexanoate (hereinafter referred to as the present compound (4)).

The Present Compound (4):

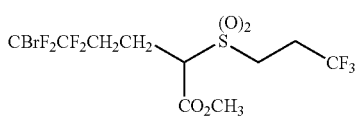

$^1$H-NMR (CDCl$_3$, TMS): δ (ppm) 3.92 (s, 3H), 3.88-3.95 (m, 1H), 3.38-3.52 (m, 2H), 2.63-2.78 (m, 2H), 2.24-2.55 (m, 4H).

Production Example 5

To a solution of 0.4 g of the present compound (4) in 30 ml of dimethyl sulfoxide was added 0.04 g of sodium hydride (60% in oil) at room temperature. The mixture was stirred at the same temperature for 0.5 hours. To the mixture was added 0.4 g of anhydrous copper(II) chloride at room temperature, and stirred for 4 hours. To the reaction mixture was added 10% hydrochloric acid was, and then extracted with ethyl acetate. The organic layer was washed with a saturated sodium chloride aqueous solution, dried over anhydrous magnesium sulfate, and then concentrated under reduced pressure. The obtained residue was subjected to silica gel chromatography to obtain 0.40 g of methyl 6-bromo-2-chloro-5,5,6,6-tetrafluoro-2-(3,3,3-trifluoropropylsulfonyl)hexanoate (hereinafter referred to as the present compound (5)).

The Present Compound (5):

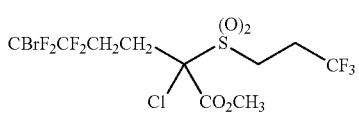

$^1$H-NMR (CDCl$_3$, TMS): δ (ppm) 3.97 (s, 3H), 3.50-3.94 (m, 2H), 2.30-2.92 (m, 6H).

Production Example 6

To a solution of 0.3 g of the present compound (5) in 20 ml of methanol was added 0.2 ml of ammonia (7M methanol solution) at room temperature. The mixture was stirred at the same temperature for 14 hours. The reaction mixture was concentrated under reduced pressure. The obtained residue was subjected to silica gel chromatography to obtain 0.19 g of 6-bromo-2-chloro-5,5,6,6-tetrafluoro-2-(3,3,3-trifluoropropylsulfonyl)hexanamide (hereinafter referred to as the present compound (6)).

The Present Compound (6):

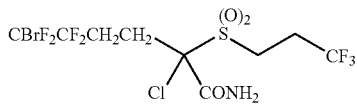

$^1$H-NMR (CDCl$_3$, TMS): δ (ppm) 6.87 (bs, 1H), 5.98 (bs, 1H), 3.38-3.75 (m, 2H), 2.18-2.95 (m, 6H).

Next, specific examples of the compound of the present invention are shown.

A compound represented by the formula (I-A):

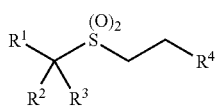

wherein R$^1$, R$^2$, R$^3$ and R$^4$ represent combinations shown in Table 1 to Table 50.

TABLE 1

| R$^1$ | R$^2$ | R$^3$ | R$^4$ |
|---|---|---|---|
| CH$_2$CH$_2$CClFCClF$_2$ | CN | H | CF$_3$ |
| CH$_2$CH$_2$CClFCClF$_2$ | CN | H | CF$_2$CF$_3$ |
| CH$_2$CH$_2$CClFCClF$_2$ | CN | H | CF$_2$CF$_2$CF$_3$ |
| CH$_2$CH$_2$CClFCClF$_2$ | CN | CH$_3$ | CF$_3$ |
| CH$_2$CH$_2$CClFCClF$_2$ | CN | CH$_3$ | CF$_2$CF$_3$ |
| CH$_2$CH$_2$CClFCClF$_2$ | CN | CH$_3$ | CF$_2$CF$_2$CF$_3$ |
| CH$_2$CH$_2$CClFCClF$_2$ | CN | CH$_2$CH$_3$ | CF$_3$ |
| CH$_2$CH$_2$CClFCClF$_2$ | CN | CH$_2$CH$_3$ | CF$_2$CF$_3$ |
| CH$_2$CH$_2$CClFCClF$_2$ | CN | CH$_2$CH$_3$ | CF$_2$CF$_2$CF$_3$ |
| CH$_2$CH$_2$CClFCClF$_2$ | CN | F | CF$_3$ |
| CH$_2$CH$_2$CClFCClF$_2$ | CN | F | CF$_2$CF$_3$ |
| CH$_2$CH$_2$CClFCClF$_2$ | CN | F | CF$_2$CF$_2$CF$_3$ |
| CH$_2$CH$_2$CClFCClF$_2$ | CN | Cl | CF$_3$ |
| CH$_2$CH$_2$CClFCClF$_2$ | CN | Cl | CF$_2$CF$_3$ |
| CH$_2$CH$_2$CClFCClF$_2$ | CN | Cl | CF$_2$CF$_2$CF$_3$ |
| CH$_2$CH$_2$CClFCClF$_2$ | CO$_2$CH$_3$ | H | CF$_3$ |
| CH$_2$CH$_2$CClFCClF$_2$ | CO$_2$CH$_3$ | H | CF$_2$CF$_3$ |
| CH$_2$CH$_2$CClFCClF$_2$ | CO$_2$CH$_3$ | H | CF$_2$CF$_2$CF$_3$ |
| CH$_2$CH$_2$CClFCClF$_2$ | CO$_2$CH$_3$ | CH$_3$ | CF$_3$ |
| CH$_2$CH$_2$CClFCClF$_2$ | CO$_2$CH$_3$ | CH$_3$ | CF$_2$CF$_3$ |
| CH$_2$CH$_2$CClFCClF$_2$ | CO$_2$CH$_3$ | CH$_3$ | CF$_2$CF$_2$CF$_3$ |
| CH$_2$CH$_2$CClFCClF$_2$ | CO$_2$CH$_3$ | CH$_2$CH$_3$ | CF$_3$ |
| CH$_2$CH$_2$CClFCClF$_2$ | CO$_2$CH$_3$ | CH$_2$CH$_3$ | CF$_2$CF$_3$ |
| CH$_2$CH$_2$CClFCClF$_2$ | CO$_2$CH$_3$ | CH$_2$CH$_3$ | CF$_2$CF$_2$CF$_3$ |
| CH$_2$CH$_2$CClFCClF$_2$ | CO$_2$CH$_3$ | F | CF$_3$ |
| CH$_2$CH$_2$CClFCClF$_2$ | CO$_2$CH$_3$ | F | CF$_2$CF$_3$ |
| CH$_2$CH$_2$CClFCClF$_2$ | CO$_2$CH$_3$ | F | CF$_2$CF$_2$CF$_3$ |
| CH$_2$CH$_2$CClFCClF$_2$ | CO$_2$CH$_3$ | Cl | CF$_3$ |
| CH$_2$CH$_2$CClFCClF$_2$ | CO$_2$CH$_3$ | Cl | CF$_2$CF$_3$ |
| CH$_2$CH$_2$CClFCClF$_2$ | CO$_2$CH$_3$ | Cl | CF$_2$CF$_2$CF$_3$ |

TABLE 2

| R$^1$ | R$^2$ | R$^3$ | R$^4$ |
|---|---|---|---|
| CH$_2$CH$_2$CClFCClF$_2$ | CO$_2$C(CH$_3$)$_3$ | H | CF$_3$ |
| CH$_2$CH$_2$CClFCClF$_2$ | CO$_2$C(CH$_3$)$_3$ | H | CF$_2$CF$_3$ |
| CH$_2$CH$_2$CClFCClF$_2$ | CO$_2$C(CH$_3$)$_3$ | H | CF$_2$CF$_2$CF$_3$ |
| CH$_2$CH$_2$CClFCClF$_2$ | CO$_2$C(CH$_3$)$_3$ | CH$_3$ | CF$_3$ |
| CH$_2$CH$_2$CClFCClF$_2$ | CO$_2$C(CH$_3$)$_3$ | CH$_3$ | CF$_2$CF$_3$ |
| CH$_2$CH$_2$CClFCClF$_2$ | CO$_2$C(CH$_3$)$_3$ | CH$_3$ | CF$_2$CF$_2$CF$_3$ |
| CH$_2$CH$_2$CClFCClF$_2$ | CO$_2$C(CH$_3$)$_3$ | CH$_2$CH$_3$ | CF$_3$ |
| CH$_2$CH$_2$CClFCClF$_2$ | CO$_2$C(CH$_3$)$_3$ | CH$_2$CH$_3$ | CF$_2$CF$_3$ |
| CH$_2$CH$_2$CClFCClF$_2$ | CO$_2$C(CH$_3$)$_3$ | CH$_2$CH$_3$ | CF$_2$CF$_2$CF$_3$ |
| CH$_2$CH$_2$CClFCClF$_2$ | CO$_2$C(CH$_3$)$_3$ | F | CF$_3$ |
| CH$_2$CH$_2$CClFCClF$_2$ | CO$_2$C(CH$_3$)$_3$ | F | CF$_2$CF$_3$ |
| CH$_2$CH$_2$CClFCClF$_2$ | CO$_2$C(CH$_3$)$_3$ | F | CF$_2$CF$_2$CF$_3$ |
| CH$_2$CH$_2$CClFCClF$_2$ | CO$_2$C(CH$_3$)$_3$ | Cl | CF$_3$ |
| CH$_2$CH$_2$CClFCClF$_2$ | CO$_2$C(CH$_3$)$_3$ | Cl | CF$_2$CF$_3$ |
| CH$_2$CH$_2$CClFCClF$_2$ | CO$_2$C(CH$_3$)$_3$ | Cl | CF$_2$CF$_2$CF$_3$ |
| CH$_2$CH$_2$CClFCClF$_2$ | CONH$_2$ | H | CF$_3$ |
| CH$_2$CH$_2$CClFCClF$_2$ | CONH$_2$ | H | CF$_2$CF$_3$ |
| CH$_2$CH$_2$CClFCClF$_2$ | CONH$_2$ | H | CF$_2$CF$_2$CF$_3$ |
| CH$_2$CH$_2$CClFCClF$_2$ | CONH$_2$ | CH$_3$ | CF$_3$ |
| CH$_2$CH$_2$CClFCClF$_2$ | CONH$_2$ | CH$_3$ | CF$_2$CF$_3$ |
| CH$_2$CH$_2$CClFCClF$_2$ | CONH$_2$ | CH$_3$ | CF$_2$CF$_2$CF$_3$ |
| CH$_2$CH$_2$CClFCClF$_2$ | CONH$_2$ | CH$_2$CH$_3$ | CF$_3$ |
| CH$_2$CH$_2$CClFCClF$_2$ | CONH$_2$ | CH$_2$CH$_3$ | CF$_2$CF$_3$ |
| CH$_2$CH$_2$CClFCClF$_2$ | CONH$_2$ | CH$_2$CH$_3$ | CF$_2$CF$_2$CF$_3$ |
| CH$_2$CH$_2$CClFCClF$_2$ | CONH$_2$ | F | CF$_3$ |
| CH$_2$CH$_2$CClFCClF$_2$ | CONH$_2$ | F | CF$_2$CF$_3$ |
| CH$_2$CH$_2$CClFCClF$_2$ | CONH$_2$ | F | CF$_2$CF$_2$CF$_3$ |
| CH$_2$CH$_2$CClFCClF$_2$ | CONH$_2$ | Cl | CF$_3$ |
| CH$_2$CH$_2$CClFCClF$_2$ | CONH$_2$ | Cl | CF$_2$CF$_3$ |
| CH$_2$CH$_2$CClFCClF$_2$ | CONH$_2$ | Cl | CF$_2$CF$_2$CF$_3$ |

TABLE 3

| R$^1$ | R$^2$ | R$^3$ | R$^4$ |
|---|---|---|---|
| CH$_2$CH$_2$CClFCClF$_2$ | CONH(CH$_3$) | H | CF$_3$ |
| CH$_2$CH$_2$CClFCClF$_2$ | CONH(CH$_3$) | H | CF$_2$CF$_3$ |
| CH$_2$CH$_2$CClFCClF$_2$ | CONH(CH$_3$) | H | CF$_2$CF$_2$CF$_3$ |
| CH$_2$CH$_2$CClFCClF$_2$ | CONH(CH$_3$) | CH$_3$ | CF$_3$ |
| CH$_2$CH$_2$CClFCClF$_2$ | CONH(CH$_3$) | CH$_3$ | CF$_2$CF$_3$ |
| CH$_2$CH$_2$CClFCClF$_2$ | CONH(CH$_3$) | CH$_3$ | CF$_2$CF$_2$CF$_3$ |
| CH$_2$CH$_2$CClFCClF$_2$ | CONH(CH$_3$) | CH$_2$CH$_3$ | CF$_3$ |
| CH$_2$CH$_2$CClFCClF$_2$ | CONH(CH$_3$) | CH$_2$CH$_3$ | CF$_2$CF$_3$ |
| CH$_2$CH$_2$CClFCClF$_2$ | CONH(CH$_3$) | CH$_2$CH$_3$ | CF$_2$CF$_2$CF$_3$ |
| CH$_2$CH$_2$CClFCClF$_2$ | CONH(CH$_3$) | F | CF$_3$ |
| CH$_2$CH$_2$CClFCClF$_2$ | CONH(CH$_3$) | F | CF$_2$CF$_3$ |
| CH$_2$CH$_2$CClFCClF$_2$ | CONH(CH$_3$) | F | CF$_2$CF$_2$CF$_3$ |
| CH$_2$CH$_2$CClFCClF$_2$ | CONH(CH$_3$) | Cl | CF$_3$ |
| CH$_2$CH$_2$CClFCClF$_2$ | CONH(CH$_3$) | Cl | CF$_2$CF$_3$ |
| CH$_2$CH$_2$CClFCClF$_2$ | CONH(CH$_3$) | Cl | CF$_2$CF$_2$CF$_3$ |
| CH$_2$CH$_2$CClFCClF$_2$ | CONH(CH$_2$CH$_3$) | H | CF$_3$ |
| CH$_2$CH$_2$CClFCClF$_2$ | CONH(CH$_2$CH$_3$) | H | CF$_2$CF$_3$ |
| CH$_2$CH$_2$CClFCClF$_2$ | CONH(CH$_2$CH$_3$) | H | CF$_2$CF$_2$CF$_3$ |
| CH$_2$CH$_2$CClFCClF$_2$ | CONH(CH$_2$CH$_3$) | CH$_3$ | CF$_3$ |
| CH$_2$CH$_2$CClFCClF$_2$ | CONH(CH$_2$CH$_3$) | CH$_3$ | CF$_2$CF$_3$ |
| CH$_2$CH$_2$CClFCClF$_2$ | CONH(CH$_2$CH$_3$) | CH$_3$ | CF$_2$CF$_2$CF$_3$ |
| CH$_2$CH$_2$CClFCClF$_2$ | CONH(CH$_2$CH$_3$) | CH$_2$CH$_3$ | CF$_3$ |
| CH$_2$CH$_2$CClFCClF$_2$ | CONH(CH$_2$CH$_3$) | CH$_2$CH$_3$ | CF$_2$CF$_3$ |
| CH$_2$CH$_2$CClFCClF$_2$ | CONH(CH$_2$CH$_3$) | CH$_2$CH$_3$ | CF$_2$CF$_2$CF$_3$ |
| CH$_2$CH$_2$CClFCClF$_2$ | CONH(CH$_2$CH$_3$) | F | CF$_3$ |
| CH$_2$CH$_2$CClFCClF$_2$ | CONH(CH$_2$CH$_3$) | F | CF$_2$CF$_3$ |
| CH$_2$CH$_2$CClFCClF$_2$ | CONH(CH$_2$CH$_3$) | F | CF$_2$CF$_2$CF$_3$ |
| CH$_2$CH$_2$CClFCClF$_2$ | CONH(CH$_2$CH$_3$) | Cl | CF$_3$ |
| CH$_2$CH$_2$CClFCClF$_2$ | CONH(CH$_2$CH$_3$) | Cl | CF$_2$CF$_3$ |
| CH$_2$CH$_2$CClFCClF$_2$ | CONH(CH$_2$CH$_3$) | Cl | CF$_2$CF$_2$CF$_3$ |

TABLE 4

| R$^1$ | R$^2$ | R$^3$ | R$^4$ |
|---|---|---|---|
| CH$_2$CH$_2$CClFCClF$_2$ | CON(CH$_3$)$_2$ | H | CF$_3$ |
| CH$_2$CH$_2$CClFCClF$_2$ | CON(CH$_3$)$_2$ | H | CF$_2$CF$_3$ |
| CH$_2$CH$_2$CClFCClF$_2$ | CON(CH$_3$)$_2$ | H | CF$_2$CF$_2$CF$_3$ |
| CH$_2$CH$_2$CClFCClF$_2$ | CON(CH$_3$)$_2$ | CH$_3$ | CF$_3$ |
| CH$_2$CH$_2$CClFCClF$_2$ | CON(CH$_3$)$_2$ | CH$_3$ | CF$_2$CF$_3$ |
| CH$_2$CH$_2$CClFCClF$_2$ | CON(CH$_3$)$_2$ | CH$_3$ | CF$_2$CF$_2$CF$_3$ |
| CH$_2$CH$_2$CClFCClF$_2$ | CON(CH$_3$)$_2$ | CH$_2$CH$_3$ | CF$_3$ |
| CH$_2$CH$_2$CClFCClF$_2$ | CON(CH$_3$)$_2$ | CH$_2$CH$_3$ | CF$_2$CF$_3$ |
| CH$_2$CH$_2$CClFCClF$_2$ | CON(CH$_3$)$_2$ | CH$_2$CH$_3$ | CF$_2$CF$_2$CF$_3$ |
| CH$_2$CH$_2$CClFCClF$_2$ | CON(CH$_3$)$_2$ | F | CF$_3$ |
| CH$_2$CH$_2$CClFCClF$_2$ | CON(CH$_3$)$_2$ | F | CF$_2$CF$_3$ |
| CH$_2$CH$_2$CClFCClF$_2$ | CON(CH$_3$)$_2$ | F | CF$_2$CF$_2$CF$_3$ |
| CH$_2$CH$_2$CClFCClF$_2$ | CON(CH$_3$)$_2$ | Cl | CF$_3$ |

TABLE 4-continued

| R¹ | R² | R³ | R⁴ |
|---|---|---|---|
| CH₂CH₂CClFCClF₂ | CON(CH₃)₂ | Cl | CF₂CF₃ |
| CH₂CH₂CClFCClF₂ | CON(CH₃)₂ | Cl | CF₂CF₂CF₃ |
| CH₂CH₂CClFCClF₂ | C(S)OCH₃ | H | CF₃ |
| CH₂CH₂CClFCClF₂ | C(S)OCH₃ | H | CF₂CF₃ |
| CH₂CH₂CClFCClF₂ | C(S)OCH₃ | H | CF₂CF₂CF₃ |
| CH₂CH₂CClFCClF₂ | C(S)OCH₃ | CH₃ | CF₃ |
| CH₂CH₂CClFCClF₂ | C(S)OCH₃ | CH₃ | CF₂CF₃ |
| CH₂CH₂CClFCClF₂ | C(S)OCH₃ | CH₃ | CF₂CF₂CF₃ |
| CH₂CH₂CClFCClF₂ | C(S)OCH₃ | CH₂CH₃ | CF₃ |
| CH₂CH₂CClFCClF₂ | C(S)OCH₃ | CH₂CH₃ | CF₂CF₃ |
| CH₂CH₂CClFCClF₂ | C(S)OCH₃ | CH₂CH₃ | CF₂CF₂CF₃ |
| CH₂CH₂CClFCClF₂ | C(S)OCH₃ | F | CF₃ |
| CH₂CH₂CClFCClF₂ | C(S)OCH₃ | F | CF₂CF₃ |
| CH₂CH₂CClFCClF₂ | C(S)OCH₃ | F | CF₂CF₂CF₃ |
| CH₂CH₂CClFCClF₂ | C(S)OCH₃ | Cl | CF₃ |
| CH₂CH₂CClFCClF₂ | C(S)OCH₃ | Cl | CF₂CF₃ |
| CH₂CH₂CClFCClF₂ | C(S)OCH₃ | Cl | CF₂CF₂CF₃ |

TABLE 5

| R¹ | R² | R³ | R⁴ |
|---|---|---|---|
| CH₂CH₂CClFCClF₂ | C(S)NH₂ | H | CF₃ |
| CH₂CH₂CClFCClF₂ | C(S)NH₂ | H | CF₂CF₃ |
| CH₂CH₂CClFCClF₂ | C(S)NH₂ | H | CF₂CF₂CF₃ |
| CH₂CH₂CClFCClF₂ | C(S)NH₂ | CH₃ | CF₃ |
| CH₂CH₂CClFCClF₂ | C(S)NH₂ | CH₃ | CF₂CF₃ |
| CH₂CH₂CClFCClF₂ | C(S)NH₂ | CH₃ | CF₂CF₂CF₃ |
| CH₂CH₂CClFCClF₂ | C(S)NH₂ | CH₂CH₃ | CF₃ |
| CH₂CH₂CClFCClF₂ | C(S)NH₂ | CH₂CH₃ | CF₂CF₃ |
| CH₂CH₂CClFCClF₂ | C(S)NH₂ | CH₂CH₃ | CF₂CF₂CF₃ |
| CH₂CH₂CClFCClF₂ | C(S)NH₂ | F | CF₃ |
| CH₂CH₂CClFCClF₂ | C(S)NH₂ | F | CF₂CF₃ |
| CH₂CH₂CClFCClF₂ | C(S)NH₂ | F | CF₂CF₂CF₃ |
| CH₂CH₂CClFCClF₂ | C(S)NH₂ | Cl | CF₃ |
| CH₂CH₂CClFCClF₂ | C(S)NH₂ | Cl | CF₂CF₃ |
| CH₂CH₂CClFCClF₂ | C(S)NH₂ | Cl | CF₂CF₂CF₃ |
| CH₂CH₂CClFCClF₂ | C(S)NH(CH₃) | H | CF₃ |
| CH₂CH₂CClFCClF₂ | C(S)NH(CH₃) | H | CF₂CF₃ |
| CH₂CH₂CClFCClF₂ | C(S)NH(CH₃) | H | CF₂CF₂CF₃ |
| CH₂CH₂CClFCClF₂ | C(S)NH(CH₃) | CH₃ | CF₃ |
| CH₂CH₂CClFCClF₂ | C(S)NH(CH₃) | CH₃ | CF₂CF₃ |
| CH₂CH₂CClFCClF₂ | C(S)NH(CH₃) | CH₃ | CF₂CF₂CF₃ |
| CH₂CH₂CClFCClF₂ | C(S)NH(CH₃) | CH₂CH₃ | CF₃ |
| CH₂CH₂CClFCClF₂ | C(S)NH(CH₃) | CH₂CH₃ | CF₂CF₃ |
| CH₂CH₂CClFCClF₂ | C(S)NH(CH₃) | CH₂CH₃ | CF₂CF₂CF₃ |
| CH₂CH₂CClFCClF₂ | C(S)NH(CH₃) | F | CF₃ |
| CH₂CH₂CClFCClF₂ | C(S)NH(CH₃) | F | CF₂CF₃ |
| CH₂CH₂CClFCClF₂ | C(S)NH(CH₃) | F | CF₂CF₂CF₃ |
| CH₂CH₂CClFCClF₂ | C(S)NH(CH₃) | Cl | CF₃ |
| CH₂CH₂CClFCClF₂ | C(S)NH(CH₃) | Cl | CF₂CF₃ |
| CH₂CH₂CClFCClF₂ | C(S)NH(CH₃) | Cl | CF₂CF₂CF₃ |

TABLE 6

| R¹ | R² | R³ | R⁴ |
|---|---|---|---|
| CH₂CH₂CClFCClF₂ | C(S)N(CH₃)₂ | H | CF₃ |
| CH₂CH₂CClFCClF₂ | C(S)N(CH₃)₂ | H | CF₂CF₃ |
| CH₂CH₂CClFCClF₂ | C(S)N(CH₃)₂ | H | CF₂CF₂CF₃ |
| CH₂CH₂CClFCClF₂ | C(S)N(CH₃)₂ | CH₃ | CF₃ |
| CH₂CH₂CClFCClF₂ | C(S)N(CH₃)₂ | CH₃ | CF₂CF₃ |
| CH₂CH₂CClFCClF₂ | C(S)N(CH₃)₂ | CH₃ | CF₂CF₂CF₃ |
| CH₂CH₂CClFCClF₂ | C(S)N(CH₃)₂ | CH₂CH₃ | CF₃ |
| CH₂CH₂CClFCClF₂ | C(S)N(CH₃)₂ | CH₂CH₃ | CF₂CF₃ |
| CH₂CH₂CClFCClF₂ | C(S)N(CH₃)₂ | CH₂CH₃ | CF₂CF₂CF₃ |
| CH₂CH₂CClFCClF₂ | C(S)N(CH₃)₂ | F | CF₃ |
| CH₂CH₂CClFCClF₂ | C(S)N(CH₃)₂ | F | CF₂CF₃ |
| CH₂CH₂CClFCClF₂ | C(S)N(CH₃)₂ | F | CF₂CF₂CF₃ |
| CH₂CH₂CClFCClF₂ | C(S)N(CH₃)₂ | Cl | CF₃ |
| CH₂CH₂CClFCClF₂ | C(S)N(CH₃)₂ | Cl | CF₂CF₃ |
| CH₂CH₂CClFCClF₂ | C(S)N(CH₃)₂ | Cl | CF₂CF₂CF₃ |
| CH₂CH₂CF₂CBrF₂ | CN | H | CF₃ |

TABLE 6-continued

| R¹ | R² | R³ | R⁴ |
|---|---|---|---|
| CH₂CH₂CF₂CBrF₂ | CN | H | CF₂CF₃ |
| CH₂CH₂CF₂CBrF₂ | CN | H | CF₂CF₂CF₃ |
| CH₂CH₂CF₂CBrF₂ | CN | CH₃ | CF₃ |
| CH₂CH₂CF₂CBrF₂ | CN | CH₃ | CF₂CF₃ |
| CH₂CH₂CF₂CBrF₂ | CN | CH₃ | CF₂CF₂CF₃ |
| CH₂CH₂CF₂CBrF₂ | CN | CH₂CH₃ | CF₃ |
| CH₂CH₂CF₂CBrF₂ | CN | CH₂CH₃ | CF₂CF₃ |
| CH₂CH₂CF₂CBrF₂ | CN | CH₂CH₃ | CF₂CF₂CF₃ |
| CH₂CH₂CF₂CBrF₂ | CN | F | CF₃ |
| CH₂CH₂CF₂CBrF₂ | CN | F | CF₂CF₃ |
| CH₂CH₂CF₂CBrF₂ | CN | F | CF₂CF₂CF₃ |
| CH₂CH₂CF₂CBrF₂ | CN | Cl | CF₃ |
| CH₂CH₂CF₂CBrF₂ | CN | Cl | CF₂CF₃ |
| CH₂CH₂CF₂CBrF₂ | CN | Cl | CF₂CF₂CF₃ |

TABLE 7

| R¹ | R² | R³ | R⁴ |
|---|---|---|---|
| CH₂CH₂CF₂CBrF₂ | CO₂CH₃ | H | CF₃ |
| CH₂CH₂CF₂CBrF₂ | CO₂CH₃ | H | CF₂CF₃ |
| CH₂CH₂CF₂CBrF₂ | CO₂CH₃ | H | CF₂CF₂CF₃ |
| CH₂CH₂CF₂CBrF₂ | CO₂CH₃ | CH₃ | CF₃ |
| CH₂CH₂CF₂CBrF₂ | CO₂CH₃ | CH₃ | CF₂CF₃ |
| CH₂CH₂CF₂CBrF₂ | CO₂CH₃ | CH₃ | CF₂CF₂CF₃ |
| CH₂CH₂CF₂CBrF₂ | CO₂CH₃ | CH₂CH₃ | CF₃ |
| CH₂CH₂CF₂CBrF₂ | CO₂CH₃ | CH₂CH₃ | CF₂CF₃ |
| CH₂CH₂CF₂CBrF₂ | CO₂CH₃ | CH₂CH₃ | CF₂CF₂CF₃ |
| CH₂CH₂CF₂CBrF₂ | CO₂CH₃ | F | CF₃ |
| CH₂CH₂CF₂CBrF₂ | CO₂CH₃ | F | CF₂CF₃ |
| CH₂CH₂CF₂CBrF₂ | CO₂CH₃ | F | CF₂CF₂CF₃ |
| CH₂CH₂CF₂CBrF₂ | CO₂CH₃ | Cl | CF₃ |
| CH₂CH₂CF₂CBrF₂ | CO₂CH₃ | Cl | CF₂CF₃ |
| CH₂CH₂CF₂CBrF₂ | CO₂CH₃ | Cl | CF₂CF₂CF₃ |
| CH₂CH₂CF₂CBrF₂ | CO₂C(CH₃)₃ | H | CF₃ |
| CH₂CH₂CF₂CBrF₂ | CO₂C(CH₃)₃ | H | CF₂CF₃ |
| CH₂CH₂CF₂CBrF₂ | CO₂C(CH₃)₃ | H | CF₂CF₂CF₃ |
| CH₂CH₂CF₂CBrF₂ | CO₂C(CH₃)₃ | CH₃ | CF₃ |
| CH₂CH₂CF₂CBrF₂ | CO₂C(CH₃)₃ | CH₃ | CF₂CF₃ |
| CH₂CH₂CF₂CBrF₂ | CO₂C(CH₃)₃ | CH₃ | CF₂CF₂CF₃ |
| CH₂CH₂CF₂CBrF₂ | CO₂C(CH₃)₃ | CH₂CH₃ | CF₃ |
| CH₂CH₂CF₂CBrF₂ | CO₂C(CH₃)₃ | CH₂CH₃ | CF₂CF₃ |
| CH₂CH₂CF₂CBrF₂ | CO₂C(CH₃)₃ | CH₂CH₃ | CF₂CF₂CF₃ |
| CH₂CH₂CF₂CBrF₂ | CO₂C(CH₃)₃ | F | CF₃ |
| CH₂CH₂CF₂CBrF₂ | CO₂C(CH₃)₃ | F | CF₂CF₃ |
| CH₂CH₂CF₂CBrF₂ | CO₂C(CH₃)₃ | F | CF₂CF₂CF₃ |
| CH₂CH₂CF₂CBrF₂ | CO₂C(CH₃)₃ | Cl | CF₃ |
| CH₂CH₂CF₂CBrF₂ | CO₂C(CH₃)₃ | Cl | CF₂CF₃ |
| CH₂CH₂CF₂CBrF₂ | CO₂C(CH₃)₃ | Cl | CF₂CF₂CF₃ |

TABLE 8

| R¹ | R² | R³ | R⁴ |
|---|---|---|---|
| CH₂CH₂CF₂CBrF₂ | CONH₂ | H | CF₃ |
| CH₂CH₂CF₂CBrF₂ | CONH₂ | H | CF₂CF₃ |
| CH₂CH₂CF₂CBrF₂ | CONH₂ | H | CF₂CF₂CF₃ |
| CH₂CH₂CF₂CBrF₂ | CONH₂ | CH₃ | CF₃ |
| CH₂CH₂CF₂CBrF₂ | CONH₂ | CH₃ | CF₂CF₃ |
| CH₂CH₂CF₂CBrF₂ | CONH₂ | CH₃ | CF₂CF₂CF₃ |
| CH₂CH₂CF₂CBrF₂ | CONH₂ | CH₂CH₃ | CF₃ |
| CH₂CH₂CF₂CBrF₂ | CONH₂ | CH₂CH₃ | CF₂CF₃ |
| CH₂CH₂CF₂CBrF₂ | CONH₂ | CH₂CH₃ | CF₂CF₂CF₃ |
| CH₂CH₂CF₂CBrF₂ | CONH₂ | F | CF₃ |
| CH₂CH₂CF₂CBrF₂ | CONH₂ | F | CF₂CF₃ |
| CH₂CH₂CF₂CBrF₂ | CONH₂ | F | CF₂CF₂CF₃ |
| CH₂CH₂CF₂CBrF₂ | CONH₂ | Cl | CF₃ |
| CH₂CH₂CF₂CBrF₂ | CONH₂ | Cl | CF₂CF₃ |
| CH₂CH₂CF₂CBrF₂ | CONH₂ | Cl | CF₂CF₂CF₃ |
| CH₂CH₂CF₂CBrF₂ | CONH(CH₃) | H | CF₃ |
| CH₂CH₂CF₂CBrF₂ | CONH(CH₃) | H | CF₂CF₃ |
| CH₂CH₂CF₂CBrF₂ | CONH(CH₃) | H | CF₂CF₂CF₃ |
| CH₂CH₂CF₂CBrF₂ | CONH(CH₃) | CH₃ | CF₃ |

TABLE 8-continued

| R¹ | R² | R³ | R⁴ |
|---|---|---|---|
| CH₂CH₂CF₂CBrF₂ | CONH(CH₃) | CH₃ | CF₂CF₃ |
| CH₂CH₂CF₂CBrF₂ | CONH(CH₃) | CH₃ | CF₂CF₂CF₃ |
| CH₂CH₂CF₂CBrF₂ | CONH(CH₃) | CH₂CH₃ | CF₃ |
| CH₂CH₂CF₂CBrF₂ | CONH(CH₃) | CH₂CH₃ | CF₂CF₃ |
| CH₂CH₂CF₂CBrF₂ | CONH(CH₃) | CH₂CH₃ | CF₂CF₂CF₃ |
| CH₂CH₂CF₂CBrF₂ | CONH(CH₃) | F | CF₃ |
| CH₂CH₂CF₂CBrF₂ | CONH(CH₃) | F | CF₂CF₃ |
| CH₂CH₂CF₂CBrF₂ | CONH(CH₃) | F | CF₂CF₂CF₃ |
| CH₂CH₂CF₂CBrF₂ | CONH(CH₃) | Cl | CF₃ |
| CH₂CH₂CF₂CBrF₂ | CONH(CH₃) | Cl | CF₂CF₃ |
| CH₂CH₂CF₂CBrF₂ | CONH(CH₃) | Cl | CF₂CF₂CF₃ |

TABLE 9

| R¹ | R² | R³ | R⁴ |
|---|---|---|---|
| CH₂CH₂CF₂CBrF₂ | CONH(CH₂CH₃) | H | CF₃ |
| CH₂CH₂CF₂CBrF₂ | CONH(CH₂CH₃) | H | CF₂CF₃ |
| CH₂CH₂CF₂CBrF₂ | CONH(CH₂CH₃) | H | CF₂CF₂CF₃ |
| CH₂CH₂CF₂CBrF₂ | CONH(CH₂CH₃) | CH₃ | CF₃ |
| CH₂CH₂CF₂CBrF₂ | CONH(CH₂CH₃) | CH₃ | CF₂CF₃ |
| CH₂CH₂CF₂CBrF₂ | CONH(CH₂CH₃) | CH₃ | CF₂CF₂CF₃ |
| CH₂CH₂CF₂CBrF₂ | CONH(CH₂CH₃) | CH₂CH₃ | CF₃ |
| CH₂CH₂CF₂CBrF₂ | CONH(CH₂CH₃) | CH₂CH₃ | CF₂CF₃ |
| CH₂CH₂CF₂CBrF₂ | CONH(CH₂CH₃) | CH₂CH₃ | CF₂CF₂CF₃ |
| CH₂CH₂CF₂CBrF₂ | CONH(CH₂CH₃) | F | CF₃ |
| CH₂CH₂CF₂CBrF₂ | CONH(CH₂CH₃) | F | CF₂CF₃ |
| CH₂CH₂CF₂CBrF₂ | CONH(CH₂CH₃) | F | CF₂CF₂CF₃ |
| CH₂CH₂CF₂CBrF₂ | CONH(CH₂CH₃) | Cl | CF₃ |
| CH₂CH₂CF₂CBrF₂ | CONH(CH₂CH₃) | Cl | CF₂CF₃ |
| CH₂CH₂CF₂CBrF₂ | CONH(CH₂CH₃) | Cl | CF₂CF₂CF₃ |
| CH₂CH₂CF₂CBrF₂ | CON(CH₃)₂ | H | CF₃ |
| CH₂CH₂CF₂CBrF₂ | CON(CH₃)₂ | H | CF₂CF₃ |
| CH₂CH₂CF₂CBrF₂ | CON(CH₃)₂ | H | CF₂CF₂CF₃ |
| CH₂CH₂CF₂CBrF₂ | CON(CH₃)₂ | CH₃ | CF₃ |
| CH₂CH₂CF₂CBrF₂ | CON(CH₃)₂ | CH₃ | CF₂CF₃ |
| CH₂CH₂CF₂CBrF₂ | CON(CH₃)₂ | CH₃ | CF₂CF₂CF₃ |
| CH₂CH₂CF₂CBrF₂ | CON(CH₃)₂ | CH₂CH₃ | CF₃ |
| CH₂CH₂CF₂CBrF₂ | CON(CH₃)₂ | CH₂CH₃ | CF₂CF₃ |
| CH₂CH₂CF₂CBrF₂ | CON(CH₃)₂ | CH₂CH₃ | CF₂CF₂CF₃ |
| CH₂CH₂CF₂CBrF₂ | CON(CH₃)₂ | F | CF₃ |
| CH₂CH₂CF₂CBrF₂ | CON(CH₃)₂ | F | CF₂CF₃ |
| CH₂CH₂CF₂CBrF₂ | CON(CH₃)₂ | F | CF₂CF₂CF₃ |
| CH₂CH₂CF₂CBrF₂ | CON(CH₃)₂ | Cl | CF₃ |
| CH₂CH₂CF₂CBrF₂ | CON(CH₃)₂ | Cl | CF₂CF₃ |
| CH₂CH₂CF₂CBrF₂ | CON(CH₃)₂ | Cl | CF₂CF₂CF₃ |

TABLE 10

| R¹ | R² | R³ | R⁴ |
|---|---|---|---|
| CH₂CH₂CF₂CBrF₂ | C(S)OCH₃ | H | CF₃ |
| CH₂CH₂CF₂CBrF₂ | C(S)OCH₃ | H | CF₂CF₃ |
| CH₂CH₂CF₂CBrF₂ | C(S)OCH₃ | H | CF₂CF₂CF₃ |
| CH₂CH₂CF₂CBrF₂ | C(S)OCH₃ | CH₃ | CF₃ |
| CH₂CH₂CF₂CBrF₂ | C(S)OCH₃ | CH₃ | CF₂CF₃ |
| CH₂CH₂CF₂CBrF₂ | C(S)OCH₃ | CH₃ | CF₂CF₂CF₃ |
| CH₂CH₂CF₂CBrF₂ | C(S)OCH₃ | CH₂CH₃ | CF₃ |
| CH₂CH₂CF₂CBrF₂ | C(S)OCH₃ | CH₂CH₃ | CF₂CF₃ |
| CH₂CH₂CF₂CBrF₂ | C(S)OCH₃ | CH₂CH₃ | CF₂CF₂CF₃ |
| CH₂CH₂CF₂CBrF₂ | C(S)OCH₃ | F | CF₃ |
| CH₂CH₂CF₂CBrF₂ | C(S)OCH₃ | F | CF₂CF₃ |
| CH₂CH₂CF₂CBrF₂ | C(S)OCH₃ | F | CF₂CF₂CF₃ |
| CH₂CH₂CF₂CBrF₂ | C(S)OCH₃ | Cl | CF₃ |
| CH₂CH₂CF₂CBrF₂ | C(S)OCH₃ | Cl | CF₂CF₃ |
| CH₂CH₂CF₂CBrF₂ | C(S)OCH₃ | Cl | CF₂CF₂CF₃ |
| CH₂CH₂CF₂CBrF₂ | C(S)NH₂ | H | CF₃ |
| CH₂CH₂CF₂CBrF₂ | C(S)NH₂ | H | CF₂CF₃ |
| CH₂CH₂CF₂CBrF₂ | C(S)NH₂ | H | CF₂CF₂CF₃ |
| CH₂CH₂CF₂CBrF₂ | C(S)NH₂ | CH₃ | CF₃ |
| CH₂CH₂CF₂CBrF₂ | C(S)NH₂ | CH₃ | CF₂CF₃ |
| CH₂CH₂CF₂CBrF₂ | C(S)NH₂ | CH₃ | CF₂CF₂CF₃ |
| CH₂CH₂CF₂CBrF₂ | C(S)NH₂ | CH₂CH₃ | CF₃ |

TABLE 10-continued

| R¹ | R² | R³ | R⁴ |
|---|---|---|---|
| CH₂CH₂CF₂CBrF₂ | C(S)NH₂ | CH₂CH₃ | CF₂CF₃ |
| CH₂CH₂CF₂CBrF₂ | C(S)NH₂ | CH₂CH₃ | CF₂CF₂CF₃ |
| CH₂CH₂CF₂CBrF₂ | C(S)NH₂ | F | CF₃ |
| CH₂CH₂CF₂CBrF₂ | C(S)NH₂ | F | CF₂CF₃ |
| CH₂CH₂CF₂CBrF₂ | C(S)NH₂ | F | CF₂CF₂CF₃ |
| CH₂CH₂CF₂CBrF₂ | C(S)NH₂ | Cl | CF₃ |
| CH₂CH₂CF₂CBrF₂ | C(S)NH₂ | Cl | CF₂CF₃ |
| CH₂CH₂CF₂CBrF₂ | C(S)NH₂ | Cl | CF₂CF₂CF₃ |

TABLE 11

| R¹ | R² | R³ | R⁴ |
|---|---|---|---|
| CH₂CH₂CF₂CBrF₂ | C(S)NH(CH₃) | H | CF₃ |
| CH₂CH₂CF₂CBrF₂ | C(S)NH(CH₃) | H | CF₂CF₃ |
| CH₂CH₂CF₂CBrF₂ | C(S)NH(CH₃) | H | CF₂CF₂CF₃ |
| CH₂CH₂CF₂CBrF₂ | C(S)NH(CH₃) | CH₃ | CF₃ |
| CH₂CH₂CF₂CBrF₂ | C(S)NH(CH₃) | CH₃ | CF₂CF₃ |
| CH₂CH₂CF₂CBrF₂ | C(S)NH(CH₃) | CH₃ | CF₂CF₂CF₃ |
| CH₂CH₂CF₂CBrF₂ | C(S)NH(CH₃) | CH₂CH₃ | CF₃ |
| CH₂CH₂CF₂CBrF₂ | C(S)NH(CH₃) | CH₂CH₃ | CF₂CF₃ |
| CH₂CH₂CF₂CBrF₂ | C(S)NH(CH₃) | CH₂CH₃ | CF₂CF₂CF₃ |
| CH₂CH₂CF₂CBrF₂ | C(S)NH(CH₃) | F | CF₃ |
| CH₂CH₂CF₂CBrF₂ | C(S)NH(CH₃) | F | CF₂CF₃ |
| CH₂CH₂CF₂CBrF₂ | C(S)NH(CH₃) | F | CF₂CF₂CF₃ |
| CH₂CH₂CF₂CBrF₂ | C(S)NH(CH₃) | Cl | CF₃ |
| CH₂CH₂CF₂CBrF₂ | C(S)NH(CH₃) | Cl | CF₂CF₃ |
| CH₂CH₂CF₂CBrF₂ | C(S)NH(CH₃) | Cl | CF₂CF₂CF₃ |
| CH₂CH₂CF₂CBrF₂ | C(S)N(CH₃)₂ | H | CF₃ |
| CH₂CH₂CF₂CBrF₂ | C(S)N(CH₃)₂ | H | CF₂CF₃ |
| CH₂CH₂CF₂CBrF₂ | C(S)N(CH₃)₂ | H | CF₂CF₂CF₃ |
| CH₂CH₂CF₂CBrF₂ | C(S)N(CH₃)₂ | CH₃ | CF₃ |
| CH₂CH₂CF₂CBrF₂ | C(S)N(CH₃)₂ | CH₃ | CF₂CF₃ |
| CH₂CH₂CF₂CBrF₂ | C(S)N(CH₃)₂ | CH₃ | CF₂CF₂CF₃ |
| CH₂CH₂CF₂CBrF₂ | C(S)N(CH₃)₂ | CH₂CH₃ | CF₃ |
| CH₂CH₂CF₂CBrF₂ | C(S)N(CH₃)₂ | CH₂CH₃ | CF₂CF₃ |
| CH₂CH₂CF₂CBrF₂ | C(S)N(CH₃)₂ | CH₂CH₃ | CF₂CF₂CF₃ |
| CH₂CH₂CF₂CBrF₂ | C(S)N(CH₃)₂ | F | CF₃ |
| CH₂CH₂CF₂CBrF₂ | C(S)N(CH₃)₂ | F | CF₂CF₃ |
| CH₂CH₂CF₂CBrF₂ | C(S)N(CH₃)₂ | F | CF₂CF₂CF₃ |
| CH₂CH₂CF₂CBrF₂ | C(S)N(CH₃)₂ | Cl | CF₃ |
| CH₂CH₂CF₂CBrF₂ | C(S)N(CH₃)₂ | Cl | CF₂CF₃ |
| CH₂CH₂CF₂CBrF₂ | C(S)N(CH₃)₂ | Cl | CF₂CF₂CF₃ |

TABLE 12

| R¹ | R² | R³ | R⁴ |
|---|---|---|---|
| CH₂CH₂CBrFCBrF₂ | CN | H | CF₃ |
| CH₂CH₂CBrFCBrF₂ | CN | H | CF₂CF₃ |
| CH₂CH₂CBrFCBrF₂ | CN | H | CF₂CF₂CF₃ |
| CH₂CH₂CBrFCBrF₂ | CN | CH₃ | CF₃ |
| CH₂CH₂CBrFCBrF₂ | CN | CH₃ | CF₂CF₃ |
| CH₂CH₂CBrFCBrF₂ | CN | CH₃ | CF₂CF₂CF₃ |
| CH₂CH₂CBrFCBrF₂ | CN | CH₂CH₃ | CF₃ |
| CH₂CH₂CBrFCBrF₂ | CN | CH₂CH₃ | CF₂CF₃ |
| CH₂CH₂CBrFCBrF₂ | CN | CH₂CH₃ | CF₂CF₂CF₃ |
| CH₂CH₂CBrFCBrF₂ | CN | F | CF₃ |
| CH₂CH₂CBrFCBrF₂ | CN | F | CF₂CF₃ |
| CH₂CH₂CBrFCBrF₂ | CN | F | CF₂CF₂CF₃ |
| CH₂CH₂CBrFCBrF₂ | CN | Cl | CF₃ |
| CH₂CH₂CBrFCBrF₂ | CN | Cl | CF₂CF₃ |
| CH₂CH₂CBrFCBrF₂ | CN | Cl | CF₂CF₂CF₃ |
| CH₂CH₂CBrFCBrF₂ | CO₂CH₃ | H | CF₃ |
| CH₂CH₂CBrFCBrF₂ | CO₂CH₃ | H | CF₂CF₃ |
| CH₂CH₂CBrFCBrF₂ | CO₂CH₃ | H | CF₂CF₂CF₃ |
| CH₂CH₂CBrFCBrF₂ | CO₂CH₃ | CH₃ | CF₃ |
| CH₂CH₂CBrFCBrF₂ | CO₂CH₃ | CH₃ | CF₂CF₃ |
| CH₂CH₂CBrFCBrF₂ | CO₂CH₃ | CH₃ | CF₂CF₂CF₃ |
| CH₂CH₂CBrFCBrF₂ | CO₂CH₃ | CH₂CH₃ | CF₃ |
| CH₂CH₂CBrFCBrF₂ | CO₂CH₃ | CH₂CH₃ | CF₂CF₃ |
| CH₂CH₂CBrFCBrF₂ | CO₂CH₃ | CH₂CH₃ | CF₂CF₂CF₃ |
| CH₂CH₂CBrFCBrF₂ | CO₂CH₃ | F | CF₃ |

TABLE 12-continued

| R¹ | R² | R³ | R⁴ |
|---|---|---|---|
| CH₂CH₂CBrFCBrF₂ | CO₂CH₃ | F | CF₂CF₃ |
| CH₂CH₂CBrFCBrF₂ | CO₂CH₃ | F | CF₂CF₂CF₃ |
| CH₂CH₂CBrFCBrF₂ | CO₂CH₃ | Cl | CF₃ |
| CH₂CH₂CBrFCBrF₂ | CO₂CH₃ | Cl | CF₂CF₃ |
| CH₂CH₂CBrFCBrF₂ | CO₂CH₃ | Cl | CF₂CF₂CF₃ |

TABLE 13

| R¹ | R² | R³ | R⁴ |
|---|---|---|---|
| CH₂CH₂CBrFCBrF₂ | CO₂C(CH₃)₃ | H | CF₃ |
| CH₂CH₂CBrFCBrF₂ | CO₂C(CH₃)₃ | H | CF₂CF₃ |
| CH₂CH₂CBrFCBrF₂ | CO₂C(CH₃)₃ | H | CF₂CF₂CF₃ |
| CH₂CH₂CBrFCBrF₂ | CO₂C(CH₃)₃ | CH₃ | CF₃ |
| CH₂CH₂CBrFCBrF₂ | CO₂C(CH₃)₃ | CH₃ | CF₂CF₃ |
| CH₂CH₂CBrFCBrF₂ | CO₂C(CH₃)₃ | CH₃ | CF₂CF₂CF₃ |
| CH₂CH₂CBrFCBrF₂ | CO₂C(CH₃)₃ | CH₂CH₃ | CF₃ |
| CH₂CH₂CBrFCBrF₂ | CO₂C(CH₃)₃ | CH₂CH₃ | CF₂CF₃ |
| CH₂CH₂CBrFCBrF₂ | CO₂C(CH₃)₃ | CH₂CH₃ | CF₂CF₂CF₃ |
| CH₂CH₂CBrFCBrF₂ | CO₂C(CH₃)₃ | F | CF₃ |
| CH₂CH₂CBrFCBrF₂ | CO₂C(CH₃)₃ | F | CF₂CF₃ |
| CH₂CH₂CBrFCBrF₂ | CO₂C(CH₃)₃ | F | CF₂CF₂CF₃ |
| CH₂CH₂CBrFCBrF₂ | CO₂C(CH₃)₃ | Cl | CF₃ |
| CH₂CH₂CBrFCBrF₂ | CO₂C(CH₃)₃ | Cl | CF₂CF₃ |
| CH₂CH₂CBrFCBrF₂ | CO₂C(CH₃)₃ | Cl | CF₂CF₂CF₃ |
| CH₂CH₂CBrFCBrF₂ | CONH₂ | H | CF₃ |
| CH₂CH₂CBrFCBrF₂ | CONH₂ | H | CF₂CF₃ |
| CH₂CH₂CBrFCBrF₂ | CONH₂ | H | CF₂CF₂CF₃ |
| CH₂CH₂CBrFCBrF₂ | CONH₂ | CH₃ | CF₃ |
| CH₂CH₂CBrFCBrF₂ | CONH₂ | CH₃ | CF₂CF₃ |
| CH₂CH₂CBrFCBrF₂ | CONH₂ | CH₃ | CF₂CF₂CF₃ |
| CH₂CH₂CBrFCBrF₂ | CONH₂ | CH₂CH₃ | CF₃ |
| CH₂CH₂CBrFCBrF₂ | CONH₂ | CH₂CH₃ | CF₂CF₃ |
| CH₂CH₂CBrFCBrF₂ | CONH₂ | CH₂CH₃ | CF₂CF₂CF₃ |
| CH₂CH₂CBrFCBrF₂ | CONH₂ | F | CF₃ |
| CH₂CH₂CBrFCBrF₂ | CONH₂ | F | CF₂CF₃ |
| CH₂CH₂CBrFCBrF₂ | CONH₂ | F | CF₂CF₂CF₃ |
| CH₂CH₂CBrFCBrF₂ | CONH₂ | Cl | CF₃ |
| CH₂CH₂CBrFCBrF₂ | CONH₂ | Cl | CF₂CF₃ |
| CH₂CH₂CBrFCBrF₂ | CONH₂ | Cl | CF₂CF₂CF₃ |

TABLE 14

| R¹ | R² | R³ | R⁴ |
|---|---|---|---|
| CH₂CH₂CBrFCBrF₂ | CONH(CH₃) | H | CF₃ |
| CH₂CH₂CBrFCBrF₂ | CONH(CH₃) | H | CF₂CF₃ |
| CH₂CH₂CBrFCBrF₂ | CONH(CH₃) | H | CF₂CF₂CF₃ |
| CH₂CH₂CBrFCBrF₂ | CONH(CH₃) | CH₃ | CF₃ |
| CH₂CH₂CBrFCBrF₂ | CONH(CH₃) | CH₃ | CF₂CF₃ |
| CH₂CH₂CBrFCBrF₂ | CONH(CH₃) | CH₃ | CF₂CF₂CF₃ |
| CH₂CH₂CBrFCBrF₂ | CONH(CH₃) | CH₂CH₃ | CF₃ |
| CH₂CH₂CBrFCBrF₂ | CONH(CH₃) | CH₂CH₃ | CF₂CF₃ |
| CH₂CH₂CBrFCBrF₂ | CONH(CH₃) | CH₂CH₃ | CF₂CF₂CF₃ |
| CH₂CH₂CBrFCBrF₂ | CONH(CH₃) | F | CF₃ |
| CH₂CH₂CBrFCBrF₂ | CONH(CH₃) | F | CF₂CF₃ |
| CH₂CH₂CBrFCBrF₂ | CONH(CH₃) | F | CF₂CF₂CF₃ |
| CH₂CH₂CBrFCBrF₂ | CONH(CH₃) | Cl | CF₃ |
| CH₂CH₂CBrFCBrF₂ | CONH(CH₃) | Cl | CF₂CF₃ |
| CH₂CH₂CBrFCBrF₂ | CONH(CH₃) | Cl | CF₂CF₂CF₃ |
| CH₂CH₂CBrFCBrF₂ | CONH(CH₂CH₃) | H | CF₃ |
| CH₂CH₂CBrFCBrF₂ | CONH(CH₂CH₃) | H | CF₂CF₃ |
| CH₂CH₂CBrFCBrF₂ | CONH(CH₂CH₃) | H | CF₂CF₂CF₃ |
| CH₂CH₂CBrFCBrF₂ | CONH(CH₂CH₃) | CH₃ | CF₃ |
| CH₂CH₂CBrFCBrF₂ | CONH(CH₂CH₃) | CH₃ | CF₂CF₃ |
| CH₂CH₂CBrFCBrF₂ | CONH(CH₂CH₃) | CH₃ | CF₂CF₂CF₃ |
| CH₂CH₂CBrFCBrF₂ | CONH(CH₂CH₃) | CH₂CH₃ | CF₃ |
| CH₂CH₂CBrFCBrF₂ | CONH(CH₂CH₃) | CH₂CH₃ | CF₂CF₃ |
| CH₂CH₂CBrFCBrF₂ | CONH(CH₂CH₃) | CH₂CH₃ | CF₂CF₂CF₃ |
| CH₂CH₂CBrFCBrF₂ | CONH(CH₂CH₃) | F | CF₃ |
| CH₂CH₂CBrFCBrF₂ | CONH(CH₂CH₃) | F | CF₂CF₃ |
| CH₂CH₂CBrFCBrF₂ | CONH(CH₂CH₃) | F | CF₂CF₂CF₃ |
| CH₂CH₂CBrFCBrF₂ | CONH(CH₂CH₃) | Cl | CF₃ |

TABLE 14-continued

| R¹ | R² | R³ | R⁴ |
|---|---|---|---|
| CH₂CH₂CBrFCBrF₂ | CONH(CH₂CH₃) | Cl | CF₂CF₃ |
| CH₂CH₂CBrFCBrF₂ | CONH(CH₂CH₃) | Cl | CF₂CF₂CF₃ |

TABLE 15

| R¹ | R² | R³ | R⁴ |
|---|---|---|---|
| CH₂CH₂CBrFCBrF₂ | CON(CH₃)₂ | H | CF₃ |
| CH₂CH₂CBrFCBrF₂ | CON(CH₃)₂ | H | CF₂CF₃ |
| CH₂CH₂CBrFCBrF₂ | CON(CH₃)₂ | H | CF₂CF₂CF₃ |
| CH₂CH₂CBrFCBrF₂ | CON(CH₃)₂ | CH₃ | CF₃ |
| CH₂CH₂CBrFCBrF₂ | CON(CH₃)₂ | CH₃ | CF₂CF₃ |
| CH₂CH₂CBrFCBrF₂ | CON(CH₃)₂ | CH₃ | CF₂CF₂CF₃ |
| CH₂CH₂CBrFCBrF₂ | CON(CH₃)₂ | CH₂CH₃ | CF₃ |
| CH₂CH₂CBrFCBrF₂ | CON(CH₃)₂ | CH₂CH₃ | CF₂CF₃ |
| CH₂CH₂CBrFCBrF₂ | CON(CH₃)₂ | CH₂CH₃ | CF₂CF₂CF₃ |
| CH₂CH₂CBrFCBrF₂ | CON(CH₃)₂ | F | CF₃ |
| CH₂CH₂CBrFCBrF₂ | CON(CH₃)₂ | F | CF₂CF₃ |
| CH₂CH₂CBrFCBrF₂ | CON(CH₃)₂ | F | CF₂CF₂CF₃ |
| CH₂CH₂CBrFCBrF₂ | CON(CH₃)₂ | Cl | CF₃ |
| CH₂CH₂CBrFCBrF₂ | CON(CH₃)₂ | Cl | CF₂CF₃ |
| CH₂CH₂CBrFCBrF₂ | CON(CH₃)₂ | Cl | CF₂CF₂CF₃ |
| CH₂CH₂CBrFCBrF₂ | C(S)OCH₃ | H | CF₃ |
| CH₂CH₂CBrFCBrF₂ | C(S)OCH₃ | H | CF₂CF₃ |
| CH₂CH₂CBrFCBrF₂ | C(S)OCH₃ | H | CF₂CF₂CF₃ |
| CH₂CH₂CBrFCBrF₂ | C(S)OCH₃ | CH₃ | CF₃ |
| CH₂CH₂CBrFCBrF₂ | C(S)OCH₃ | CH₃ | CF₂CF₃ |
| CH₂CH₂CBrFCBrF₂ | C(S)OCH₃ | CH₃ | CF₂CF₂CF₃ |
| CH₂CH₂CBrFCBrF₂ | C(S)OCH₃ | CH₂CH₃ | CF₃ |
| CH₂CH₂CBrFCBrF₂ | C(S)OCH₃ | CH₂CH₃ | CF₂CF₃ |
| CH₂CH₂CBrFCBrF₂ | C(S)OCH₃ | CH₂CH₃ | CF₂CF₂CF₃ |
| CH₂CH₂CBrFCBrF₂ | C(S)OCH₃ | F | CF₃ |
| CH₂CH₂CBrFCBrF₂ | C(S)OCH₃ | F | CF₂CF₃ |
| CH₂CH₂CBrFCBrF₂ | C(S)OCH₃ | F | CF₂CF₂CF₃ |
| CH₂CH₂CBrFCBrF₂ | C(S)OCH₃ | Cl | CF₃ |
| CH₂CH₂CBrFCBrF₂ | C(S)OCH₃ | Cl | CF₂CF₃ |
| CH₂CH₂CBrFCBrF₂ | C(S)OCH₃ | Cl | CF₂CF₂CF₃ |

TABLE 16

| R¹ | R² | R³ | R⁴ |
|---|---|---|---|
| CH₂CH₂CBrFCBrF₂ | C(S)NH₂ | H | CF₃ |
| CH₂CH₂CBrFCBrF₂ | C(S)NH₂ | H | CF₂CF₃ |
| CH₂CH₂CBrFCBrF₂ | C(S)NH₂ | H | CF₂CF₂CF₃ |
| CH₂CH₂CBrFCBrF₂ | C(S)NH₂ | CH₃ | CF₃ |
| CH₂CH₂CBrFCBrF₂ | C(S)NH₂ | CH₃ | CF₂CF₃ |
| CH₂CH₂CBrFCBrF₂ | C(S)NH₂ | CH₃ | CF₂CF₂CF₃ |
| CH₂CH₂CBrFCBrF₂ | C(S)NH₂ | CH₂CH₃ | CF₃ |
| CH₂CH₂CBrFCBrF₂ | C(S)NH₂ | CH₂CH₃ | CF₂CF₃ |
| CH₂CH₂CBrFCBrF₂ | C(S)NH₂ | CH₂CH₃ | CF₂CF₂CF₃ |
| CH₂CH₂CBrFCBrF₂ | C(S)NH₂ | F | CF₃ |
| CH₂CH₂CBrFCBrF₂ | C(S)NH₂ | F | CF₂CF₃ |
| CH₂CH₂CBrFCBrF₂ | C(S)NH₂ | F | CF₂CF₂CF₃ |
| CH₂CH₂CBrFCBrF₂ | C(S)NH₂ | Cl | CF₃ |
| CH₂CH₂CBrFCBrF₂ | C(S)NH₂ | Cl | CF₂CF₃ |
| CH₂CH₂CBrFCBrF₂ | C(S)NH₂ | Cl | CF₂CF₂CF₃ |
| CH₂CH₂CBrFCBrF₂ | C(S)NH(CH₃) | H | CF₃ |
| CH₂CH₂CBrFCBrF₂ | C(S)NH(CH₃) | H | CF₂CF₃ |
| CH₂CH₂CBrFCBrF₂ | C(S)NH(CH₃) | H | CF₂CF₂CF₃ |
| CH₂CH₂CBrFCBrF₂ | C(S)NH(CH₃) | CH₃ | CF₃ |
| CH₂CH₂CBrFCBrF₂ | C(S)NH(CH₃) | CH₃ | CF₂CF₃ |
| CH₂CH₂CBrFCBrF₂ | C(S)NH(CH₃) | CH₃ | CF₂CF₂CF₃ |
| CH₂CH₂CBrFCBrF₂ | C(S)NH(CH₃) | CH₂CH₃ | CF₃ |
| CH₂CH₂CBrFCBrF₂ | C(S)NH(CH₃) | CH₂CH₃ | CF₂CF₃ |
| CH₂CH₂CBrFCBrF₂ | C(S)NH(CH₃) | CH₂CH₃ | CF₂CF₂CF₃ |
| CH₂CH₂CBrFCBrF₂ | C(S)NH(CH₃) | F | CF₃ |
| CH₂CH₂CBrFCBrF₂ | C(S)NH(CH₃) | F | CF₂CF₃ |
| CH₂CH₂CBrFCBrF₂ | C(S)NH(CH₃) | F | CF₂CF₂CF₃ |
| CH₂CH₂CBrFCBrF₂ | C(S)NH(CH₃) | Cl | CF₃ |
| CH₂CH₂CBrFCBrF₂ | C(S)NH(CH₃) | Cl | CF₂CF₃ |
| CH₂CH₂CBrFCBrF₂ | C(S)NH(CH₃) | Cl | CF₂CF₂CF₃ |

TABLE 17

| R¹ | R² | R³ | R⁴ |
|---|---|---|---|
| CH₂CH₂CBrFCBrF₂ | C(S)N(CH₃)₂ | H | CF₃ |
| CH₂CH₂CBrFCBrF₂ | C(S)N(CH₃)₂ | H | CF₂CF₃ |
| CH₂CH₂CBrFCBrF₂ | C(S)N(CH₃)₂ | H | CF₂CF₂CF₃ |
| CH₂CH₂CBrFCBrF₂ | C(S)N(CH₃)₂ | CH₃ | CF₃ |
| CH₂CH₂CBrFCBrF₂ | C(S)N(CH₃)₂ | CH₃ | CF₂CF₃ |
| CH₂CH₂CBrFCBrF₂ | C(S)N(CH₃)₂ | CH₃ | CF₂CF₂CF₃ |
| CH₂CH₂CBrFCBrF₂ | C(S)N(CH₃)₂ | CH₂CH₃ | CF₃ |
| CH₂CH₂CBrFCBrF₂ | C(S)N(CH₃)₂ | CH₂CH₃ | CF₂CF₃ |
| CH₂CH₂CBrFCBrF₂ | C(S)N(CH₃)₂ | CH₂CH₃ | CF₂CF₂CF₃ |
| CH₂CH₂CBrFCBrF₂ | C(S)N(CH₃)₂ | F | CF₃ |
| CH₂CH₂CBrFCBrF₂ | C(S)N(CH₃)₂ | F | CF₂CF₃ |
| CH₂CH₂CBrFCBrF₂ | C(S)N(CH₃)₂ | F | CF₂CF₂CF₃ |
| CH₂CH₂CBrFCBrF₂ | C(S)N(CH₃)₂ | Cl | CF₃ |
| CH₂CH₂CBrFCBrF₂ | C(S)N(CH₃)₂ | Cl | CF₂CF₃ |
| CH₂CH₂CBrFCBrF₂ | C(S)N(CH₃)₂ | Cl | CF₂CF₂CF₃ |
| CH₂CH₂CClF₂ | CN | H | CF₃ |
| CH₂CH₂CClF₂ | CN | H | CF₂CF₃ |
| CH₂CH₂CClF₂ | CN | H | CF₂CF₂CF₃ |
| CH₂CH₂CClF₂ | CN | CH₃ | CF₃ |
| CH₂CH₂CClF₂ | CN | CH₃ | CF₂CF₃ |
| CH₂CH₂CClF₂ | CN | CH₃ | CF₂CF₂CF₃ |
| CH₂CH₂CClF₂ | CN | CH₂CH₃ | CF₃ |
| CH₂CH₂CClF₂ | CN | CH₂CH₃ | CF₂CF₃ |
| CH₂CH₂CClF₂ | CN | CH₂CH₃ | CF₂CF₂CF₃ |
| CH₂CH₂CClF₂ | CN | F | CF₃ |
| CH₂CH₂CClF₂ | CN | F | CF₂CF₃ |
| CH₂CH₂CClF₂ | CN | F | CF₂CF₂CF₃ |
| CH₂CH₂CClF₂ | CN | Cl | CF₃ |
| CH₂CH₂CClF₂ | CN | Cl | CF₂CF₃ |
| CH₂CH₂CClF₂ | CN | Cl | CF₂CF₂CF₃ |

TABLE 18

| R¹ | R² | R³ | R⁴ |
|---|---|---|---|
| CH₂CH₂CClF₂ | CO₂CH₃ | H | CF₃ |
| CH₂CH₂CClF₂ | CO₂CH₃ | H | CF₂CF₃ |
| CH₂CH₂CClF₂ | CO₂CH₃ | H | CF₂CF₂CF₃ |
| CH₂CH₂CClF₂ | CO₂CH₃ | CH₃ | CF₃ |
| CH₂CH₂CClF₂ | CO₂CH₃ | CH₃ | CF₂CF₃ |
| CH₂CH₂CClF₂ | CO₂CH₃ | CH₃ | CF₂CF₂CF₃ |
| CH₂CH₂CClF₂ | CO₂CH₃ | CH₂CH₃ | CF₃ |
| CH₂CH₂CClF₂ | CO₂CH₃ | CH₂CH₃ | CF₂CF₃ |
| CH₂CH₂CClF₂ | CO₂CH₃ | CH₂CH₃ | CF₂CF₂CF₃ |
| CH₂CH₂CClF₂ | CO₂CH₃ | F | CF₃ |
| CH₂CH₂CClF₂ | CO₂CH₃ | F | CF₂CF₃ |
| CH₂CH₂CClF₂ | CO₂CH₃ | F | CF₂CF₂CF₃ |
| CH₂CH₂CClF₂ | CO₂CH₃ | Cl | CF₃ |
| CH₂CH₂CClF₂ | CO₂CH₃ | Cl | CF₂CF₃ |
| CH₂CH₂CClF₂ | CO₂CH₃ | Cl | CF₂CF₂CF₃ |
| CH₂CH₂CClF₂ | CO₂C(CH₃)₃ | H | CF₃ |
| CH₂CH₂CClF₂ | CO₂C(CH₃)₃ | H | CF₂CF₃ |
| CH₂CH₂CClF₂ | CO₂C(CH₃)₃ | H | CF₂CF₂CF₃ |
| CH₂CH₂CClF₂ | CO₂C(CH₃)₃ | CH₃ | CF₃ |
| CH₂CH₂CClF₂ | CO₂C(CH₃)₃ | CH₃ | CF₂CF₃ |
| CH₂CH₂CClF₂ | CO₂C(CH₃)₃ | CH₃ | CF₂CF₂CF₃ |
| CH₂CH₂CClF₂ | CO₂C(CH₃)₃ | CH₂CH₃ | CF₃ |
| CH₂CH₂CClF₂ | CO₂C(CH₃)₃ | CH₂CH₃ | CF₂CF₃ |
| CH₂CH₂CClF₂ | CO₂C(CH₃)₃ | CH₂CH₃ | CF₂CF₂CF₃ |
| CH₂CH₂CClF₂ | CO₂C(CH₃)₃ | F | CF₃ |
| CH₂CH₂CClF₂ | CO₂C(CH₃)₃ | F | CF₂CF₃ |
| CH₂CH₂CClF₂ | CO₂C(CH₃)₃ | F | CF₂CF₂CF₃ |
| CH₂CH₂CClF₂ | CO₂C(CH₃)₃ | Cl | CF₃ |
| CH₂CH₂CClF₂ | CO₂C(CH₃)₃ | Cl | CF₂CF₃ |
| CH₂CH₂CClF₂ | CO₂C(CH₃)₃ | Cl | CF₂CF₂CF₃ |

TABLE 19

| R¹ | R² | R³ | R⁴ |
|---|---|---|---|
| CH₂CH₂CClF₂ | CONH₂ | H | CF₃ |
| CH₂CH₂CClF₂ | CONH₂ | H | CF₂CF₃ |
| CH₂CH₂CClF₂ | CONH₂ | H | CF₂CF₂CF₃ |
| CH₂CH₂CClF₂ | CONH₂ | CH₃ | CF₃ |
| CH₂CH₂CClF₂ | CONH₂ | CH₃ | CF₂CF₃ |
| CH₂CH₂CClF₂ | CONH₂ | CH₃ | CF₂CF₂CF₃ |
| CH₂CH₂CClF₂ | CONH₂ | CH₂CH₃ | CF₃ |
| CH₂CH₂CClF₂ | CONH₂ | CH₂CH₃ | CF₂CF₃ |
| CH₂CH₂CClF₂ | CONH₂ | CH₂CH₃ | CF₂CF₂CF₃ |
| CH₂CH₂CClF₂ | CONH₂ | F | CF₃ |
| CH₂CH₂CClF₂ | CONH₂ | F | CF₂CF₃ |
| CH₂CH₂CClF₂ | CONH₂ | F | CF₂CF₂CF₃ |
| CH₂CH₂CClF₂ | CONH₂ | Cl | CF₃ |
| CH₂CH₂CClF₂ | CONH₂ | Cl | CF₂CF₃ |
| CH₂CH₂CClF₂ | CONH₂ | Cl | CF₂CF₂CF₃ |
| CH₂CH₂CClF₂ | CONH(CH₃) | H | CF₃ |
| CH₂CH₂CClF₂ | CONH(CH₃) | H | CF₂CF₃ |
| CH₂CH₂CClF₂ | CONH(CH₃) | H | CF₂CF₂CF₃ |
| CH₂CH₂CClF₂ | CONH(CH₃) | CH₃ | CF₃ |
| CH₂CH₂CClF₂ | CONH(CH₃) | CH₃ | CF₂CF₃ |
| CH₂CH₂CClF₂ | CONH(CH₃) | CH₃ | CF₂CF₂CF₃ |
| CH₂CH₂CClF₂ | CONH(CH₃) | CH₂CH₃ | CF₃ |
| CH₂CH₂CClF₂ | CONH(CH₃) | CH₂CH₃ | CF₂CF₃ |
| CH₂CH₂CClF₂ | CONH(CH₃) | CH₂CH₃ | CF₂CF₂CF₃ |
| CH₂CH₂CClF₂ | CONH(CH₃) | F | CF₃ |
| CH₂CH₂CClF₂ | CONH(CH₃) | F | CF₂CF₃ |
| CH₂CH₂CClF₂ | CONH(CH₃) | F | CF₂CF₂CF₃ |
| CH₂CH₂CClF₂ | CONH(CH₃) | Cl | CF₃ |
| CH₂CH₂CClF₂ | CONH(CH₃) | Cl | CF₂CF₃ |
| CH₂CH₂CClF₂ | CONH(CH₃) | Cl | CF₂CF₂CF₃ |

TABLE 20

| R¹ | R² | R³ | R⁴ |
|---|---|---|---|
| CH₂CH₂CClF₂ | CONH(CH₂CH₃) | H | CF₃ |
| CH₂CH₂CClF₂ | CONH(CH₂CH₃) | H | CF₂CF₃ |
| CH₂CH₂CClF₂ | CONH(CH₂CH₃) | H | CF₂CF₂CF₃ |
| CH₂CH₂CClF₂ | CONH(CH₂CH₃) | CH₃ | CF₃ |
| CH₂CH₂CClF₂ | CONH(CH₂CH₃) | CH₃ | CF₂CF₃ |
| CH₂CH₂CClF₂ | CONH(CH₂CH₃) | CH₃ | CF₂CF₂CF₃ |
| CH₂CH₂CClF₂ | CONH(CH₂CH₃) | CH₂CH₃ | CF₃ |
| CH₂CH₂CClF₂ | CONH(CH₂CH₃) | CH₂CH₃ | CF₂CF₃ |
| CH₂CH₂CClF₂ | CONH(CH₂CH₃) | CH₂CH₃ | CF₂CF₂CF₃ |
| CH₂CH₂CClF₂ | CONH(CH₂CH₃) | F | CF₃ |
| CH₂CH₂CClF₂ | CONH(CH₂CH₃) | F | CF₂CF₃ |
| CH₂CH₂CClF₂ | CONH(CH₂CH₃) | F | CF₂CF₂CF₃ |
| CH₂CH₂CClF₂ | CONH(CH₂CH₃) | Cl | CF₃ |
| CH₂CH₂CClF₂ | CONH(CH₂CH₃) | Cl | CF₂CF₃ |
| CH₂CH₂CClF₂ | CONH(CH₂CH₃) | Cl | CF₂CF₂CF₃ |
| CH₂CH₂CClF₂ | CON(CH₃)₂ | H | CF₃ |
| CH₂CH₂CClF₂ | CON(CH₃)₂ | H | CF₂CF₃ |
| CH₂CH₂CClF₂ | CON(CH₃)₂ | H | CF₂CF₂CF₃ |
| CH₂CH₂CClF₂ | CON(CH₃)₂ | CH₃ | CF₃ |
| CH₂CH₂CClF₂ | CON(CH₃)₂ | CH₃ | CF₂CF₃ |
| CH₂CH₂CClF₂ | CON(CH₃)₂ | CH₃ | CF₂CF₂CF₃ |
| CH₂CH₂CClF₂ | CON(CH₃)₂ | CH₂CH₃ | CF₃ |
| CH₂CH₂CClF₂ | CON(CH₃)₂ | CH₂CH₃ | CF₂CF₃ |
| CH₂CH₂CClF₂ | CON(CH₃)₂ | CH₂CH₃ | CF₂CF₂CF₃ |
| CH₂CH₂CClF₂ | CON(CH₃)₂ | F | CF₃ |
| CH₂CH₂CClF₂ | CON(CH₃)₂ | F | CF₂CF₃ |
| CH₂CH₂CClF₂ | CON(CH₃)₂ | F | CF₂CF₂CF₃ |
| CH₂CH₂CClF₂ | CON(CH₃)₂ | Cl | CF₃ |
| CH₂CH₂CClF₂ | CON(CH₃)₂ | Cl | CF₂CF₃ |
| CH₂CH₂CClF₂ | CON(CH₃)₂ | Cl | CF₂CF₂CF₃ |

TABLE 21

| R¹ | R² | R³ | R⁴ |
|---|---|---|---|
| CH₂CH₂CClF₂ | C(S)OCH₃ | H | CF₃ |
| CH₂CH₂CClF₂ | C(S)OCH₃ | H | CF₂CF₃ |
| CH₂CH₂CClF₂ | C(S)OCH₃ | H | CF₂CF₂CF₃ |
| CH₂CH₂CClF₂ | C(S)OCH₃ | CH₃ | CF₃ |
| CH₂CH₂CClF₂ | C(S)OCH₃ | CH₃ | CF₂CF₃ |
| CH₂CH₂CClF₂ | C(S)OCH₃ | CH₃ | CF₂CF₂CF₃ |

TABLE 21-continued

| R¹ | R² | R³ | R⁴ |
|---|---|---|---|
| $CH_2CH_2CClF_2$ | $C(S)OCH_3$ | $CH_2CH_3$ | $CF_3$ |
| $CH_2CH_2CClF_2$ | $C(S)OCH_3$ | $CH_2CH_3$ | $CF_2CF_3$ |
| $CH_2CH_2CClF_2$ | $C(S)OCH_3$ | $CH_2CH_3$ | $CF_2CF_2CF_3$ |
| $CH_2CH_2CClF_2$ | $C(S)OCH_3$ | F | $CF_3$ |
| $CH_2CH_2CClF_2$ | $C(S)OCH_3$ | F | $CF_2CF_3$ |
| $CH_2CH_2CClF_2$ | $C(S)OCH_3$ | F | $CF_2CF_2CF_3$ |
| $CH_2CH_2CClF_2$ | $C(S)OCH_3$ | Cl | $CF_3$ |
| $CH_2CH_2CClF_2$ | $C(S)OCH_3$ | Cl | $CF_2CF_3$ |
| $CH_2CH_2CClF_2$ | $C(S)OCH_3$ | Cl | $CF_2CF_2CF_3$ |
| $CH_2CH_2CClF_2$ | $C(S)NH_2$ | H | $CF_3$ |
| $CH_2CH_2CClF_2$ | $C(S)NH_2$ | H | $CF_2CF_3$ |
| $CH_2CH_2CClF_2$ | $C(S)NH_2$ | H | $CF_2CF_2CF_3$ |
| $CH_2CH_2CClF_2$ | $C(S)NH_2$ | $CH_3$ | $CF_3$ |
| $CH_2CH_2CClF_2$ | $C(S)NH_2$ | $CH_3$ | $CF_2CF_3$ |
| $CH_2CH_2CClF_2$ | $C(S)NH_2$ | $CH_3$ | $CF_2CF_2CF_3$ |
| $CH_2CH_2CClF_2$ | $C(S)NH_2$ | $CH_2CH_3$ | $CF_3$ |
| $CH_2CH_2CClF_2$ | $C(S)NH_2$ | $CH_2CH_3$ | $CF_2CF_3$ |
| $CH_2CH_2CClF_2$ | $C(S)NH_2$ | $CH_2CH_3$ | $CF_2CF_2CF_3$ |
| $CH_2CH_2CClF_2$ | $C(S)NH_2$ | F | $CF_3$ |
| $CH_2CH_2CClF_2$ | $C(S)NH_2$ | F | $CF_2CF_3$ |
| $CH_2CH_2CClF_2$ | $C(S)NH_2$ | F | $CF_2CF_2CF_3$ |
| $CH_2CH_2CClF_2$ | $C(S)NH_2$ | Cl | $CF_3$ |
| $CH_2CH_2CClF_2$ | $C(S)NH_2$ | Cl | $CF_2CF_3$ |
| $CH_2CH_2CClF_2$ | $C(S)NH_2$ | Cl | $CF_2CF_2CF_3$ |

TABLE 22

| R¹ | R² | R³ | R⁴ |
|---|---|---|---|
| $CH_2CH_2CClF_2$ | $C(S)NH(CH_3)$ | H | $CF_3$ |
| $CH_2CH_2CClF_2$ | $C(S)NH(CH_3)$ | H | $CF_2CF_3$ |
| $CH_2CH_2CClF_2$ | $C(S)NH(CH_3)$ | H | $CF_2CF_2CF_3$ |
| $CH_2CH_2CClF_2$ | $C(S)NH(CH_3)$ | $CH_3$ | $CF_3$ |
| $CH_2CH_2CClF_2$ | $C(S)NH(CH_3)$ | $CH_3$ | $CF_2CF_3$ |
| $CH_2CH_2CClF_2$ | $C(S)NH(CH_3)$ | $CH_3$ | $CF_2CF_2CF_3$ |
| $CH_2CH_2CClF_2$ | $C(S)NH(CH_3)$ | $CH_2CH_3$ | $CF_3$ |
| $CH_2CH_2CClF_2$ | $C(S)NH(CH_3)$ | $CH_2CH_3$ | $CF_2CF_3$ |
| $CH_2CH_2CClF_2$ | $C(S)NH(CH_3)$ | $CH_2CH_3$ | $CF_2CF_2CF_3$ |
| $CH_2CH_2CClF_2$ | $C(S)NH(CH_3)$ | F | $CF_3$ |
| $CH_2CH_2CClF_2$ | $C(S)NH(CH_3)$ | F | $CF_2CF_3$ |
| $CH_2CH_2CClF_2$ | $C(S)NH(CH_3)$ | F | $CF_2CF_2CF_3$ |
| $CH_2CH_2CClF_2$ | $C(S)NH(CH_3)$ | Cl | $CF_3$ |
| $CH_2CH_2CClF_2$ | $C(S)NH(CH_3)$ | Cl | $CF_2CF_3$ |
| $CH_2CH_2CClF_2$ | $C(S)NH(CH_3)$ | Cl | $CF_2CF_2CF_3$ |
| $CH_2CH_2CClF_2$ | $C(S)N(CH_3)_2$ | H | $CF_3$ |
| $CH_2CH_2CClF_2$ | $C(S)N(CH_3)_2$ | H | $CF_2CF_3$ |
| $CH_2CH_2CClF_2$ | $C(S)N(CH_3)_2$ | H | $CF_2CF_2CF_3$ |
| $CH_2CH_2CClF_2$ | $C(S)N(CH_3)_2$ | $CH_3$ | $CF_3$ |
| $CH_2CH_2CClF_2$ | $C(S)N(CH_3)_2$ | $CH_3$ | $CF_2CF_3$ |
| $CH_2CH_2CClF_2$ | $C(S)N(CH_3)_2$ | $CH_3$ | $CF_2CF_2CF_3$ |
| $CH_2CH_2CClF_2$ | $C(S)N(CH_3)_2$ | $CH_2CH_3$ | $CF_3$ |
| $CH_2CH_2CClF_2$ | $C(S)N(CH_3)_2$ | $CH_2CH_3$ | $CF_2CF_3$ |
| $CH_2CH_2CClF_2$ | $C(S)N(CH_3)_2$ | $CH_2CH_3$ | $CF_2CF_2CF_3$ |
| $CH_2CH_2CClF_2$ | $C(S)N(CH_3)_2$ | F | $CF_3$ |
| $CH_2CH_2CClF_2$ | $C(S)N(CH_3)_2$ | F | $CF_2CF_3$ |
| $CH_2CH_2CClF_2$ | $C(S)N(CH_3)_2$ | F | $CF_2CF_2CF_3$ |
| $CH_2CH_2CClF_2$ | $C(S)N(CH_3)_2$ | Cl | $CF_3$ |
| $CH_2CH_2CClF_2$ | $C(S)N(CH_3)_2$ | Cl | $CF_2CF_3$ |
| $CH_2CH_2CClF_2$ | $C(S)N(CH_3)_2$ | Cl | $CF_2CF_2CF_3$ |

TABLE 23

| R¹ | R² | R³ | R⁴ |
|---|---|---|---|
| $CH_2CH_2CBrF_2$ | CN | H | $CF_3$ |
| $CH_2CH_2CBrF_2$ | CN | H | $CF_2CF_3$ |
| $CH_2CH_2CBrF_2$ | CN | H | $CF_2CF_2CF_3$ |
| $CH_2CH_2CBrF_2$ | CN | $CH_3$ | $CF_3$ |
| $CH_2CH_2CBrF_2$ | CN | $CH_3$ | $CF_2CF_3$ |
| $CH_2CH_2CBrF_2$ | CN | $CH_3$ | $CF_2CF_2CF_3$ |
| $CH_2CH_2CBrF_2$ | CN | $CH_2CH_3$ | $CF_3$ |
| $CH_2CH_2CBrF_2$ | CN | $CH_2CH_3$ | $CF_2CF_3$ |
| $CH_2CH_2CBrF_2$ | CN | $CH_2CH_3$ | $CF_2CF_2CF_3$ |

TABLE 23-continued

| R¹ | R² | R³ | R⁴ |
|---|---|---|---|
| $CH_2CH_2CBrF_2$ | CN | F | $CF_3$ |
| $CH_2CH_2CBrF_2$ | CN | F | $CF_2CF_3$ |
| $CH_2CH_2CBrF_2$ | CN | F | $CF_2CF_2CF_3$ |
| $CH_2CH_2CBrF_2$ | CN | Cl | $CF_3$ |
| $CH_2CH_2CBrF_2$ | CN | Cl | $CF_2CF_3$ |
| $CH_2CH_2CBrF_2$ | CN | Cl | $CF_2CF_2CF_3$ |
| $CH_2CH_2CBrF_2$ | $CO_2CH_3$ | H | $CF_3$ |
| $CH_2CH_2CBrF_2$ | $CO_2CH_3$ | H | $CF_2CF_3$ |
| $CH_2CH_2CBrF_2$ | $CO_2CH_3$ | H | $CF_2CF_2CF_3$ |
| $CH_2CH_2CBrF_2$ | $CO_2CH_3$ | $CH_3$ | $CF_3$ |
| $CH_2CH_2CBrF_2$ | $CO_2CH_3$ | $CH_3$ | $CF_2CF_3$ |
| $CH_2CH_2CBrF_2$ | $CO_2CH_3$ | $CH_3$ | $CF_2CF_2CF_3$ |
| $CH_2CH_2CBrF_2$ | $CO_2CH_3$ | $CH_2CH_3$ | $CF_3$ |
| $CH_2CH_2CBrF_2$ | $CO_2CH_3$ | $CH_2CH_3$ | $CF_2CF_3$ |
| $CH_2CH_2CBrF_2$ | $CO_2CH_3$ | $CH_2CH_3$ | $CF_2CF_2CF_3$ |
| $CH_2CH_2CBrF_2$ | $CO_2CH_3$ | F | $CF_3$ |
| $CH_2CH_2CBrF_2$ | $CO_2CH_3$ | F | $CF_2CF_3$ |
| $CH_2CH_2CBrF_2$ | $CO_2CH_3$ | F | $CF_2CF_2CF_3$ |
| $CH_2CH_2CBrF_2$ | $CO_2CH_3$ | Cl | $CF_3$ |
| $CH_2CH_2CBrF_2$ | $CO_2CH_3$ | Cl | $CF_2CF_3$ |
| $CH_2CH_2CBrF_2$ | $CO_2CH_3$ | Cl | $CF_2CF_2CF_3$ |

TABLE 24

| R¹ | R² | R³ | R⁴ |
|---|---|---|---|
| $CH_2CH_2CBrF_2$ | $CO_2C(CH_3)_3$ | H | $CF_3$ |
| $CH_2CH_2CBrF_2$ | $CO_2C(CH_3)_3$ | H | $CF_2CF_3$ |
| $CH_2CH_2CBrF_2$ | $CO_2C(CH_3)_3$ | H | $CF_2CF_2CF_3$ |
| $CH_2CH_2CBrF_2$ | $CO_2C(CH_3)_3$ | $CH_3$ | $CF_3$ |
| $CH_2CH_2CBrF_2$ | $CO_2C(CH_3)_3$ | $CH_3$ | $CF_2CF_3$ |
| $CH_2CH_2CBrF_2$ | $CO_2C(CH_3)_3$ | $CH_3$ | $CF_2CF_2CF_3$ |
| $CH_2CH_2CBrF_2$ | $CO_2C(CH_3)_3$ | $CH_2CH_3$ | $CF_3$ |
| $CH_2CH_2CBrF_2$ | $CO_2C(CH_3)_3$ | $CH_2CH_3$ | $CF_2CF_3$ |
| $CH_2CH_2CBrF_2$ | $CO_2C(CH_3)_3$ | $CH_2CH_3$ | $CF_2CF_2CF_3$ |
| $CH_2CH_2CBrF_2$ | $CO_2C(CH_3)_3$ | F | $CF_3$ |
| $CH_2CH_2CBrF_2$ | $CO_2C(CH_3)_3$ | F | $CF_2CF_3$ |
| $CH_2CH_2CBrF_2$ | $CO_2C(CH_3)_3$ | F | $CF_2CF_2CF_3$ |
| $CH_2CH_2CBrF_2$ | $CO_2C(CH_3)_3$ | Cl | $CF_3$ |
| $CH_2CH_2CBrF_2$ | $CO_2C(CH_3)_3$ | Cl | $CF_2CF_3$ |
| $CH_2CH_2CBrF_2$ | $CO_2C(CH_3)_3$ | Cl | $CF_2CF_2CF_3$ |
| $CH_2CH_2CBrF_2$ | $CONH_2$ | H | $CF_3$ |
| $CH_2CH_2CBrF_2$ | $CONH_2$ | H | $CF_2CF_3$ |
| $CH_2CH_2CBrF_2$ | $CONH_2$ | H | $CF_2CF_2CF_3$ |
| $CH_2CH_2CBrF_2$ | $CONH_2$ | $CH_3$ | $CF_3$ |
| $CH_2CH_2CBrF_2$ | $CONH_2$ | $CH_3$ | $CF_2CF_3$ |
| $CH_2CH_2CBrF_2$ | $CONH_2$ | $CH_3$ | $CF_2CF_2CF_3$ |
| $CH_2CH_2CBrF_2$ | $CONH_2$ | $CH_2CH_3$ | $CF_3$ |
| $CH_2CH_2CBrF_2$ | $CONH_2$ | $CH_2CH_3$ | $CF_2CF_3$ |
| $CH_2CH_2CBrF_2$ | $CONH_2$ | $CH_2CH_3$ | $CF_2CF_2CF_3$ |
| $CH_2CH_2CBrF_2$ | $CONH_2$ | F | $CF_3$ |
| $CH_2CH_2CBrF_2$ | $CONH_2$ | F | $CF_2CF_3$ |
| $CH_2CH_2CBrF_2$ | $CONH_2$ | F | $CF_2CF_2CF_3$ |
| $CH_2CH_2CBrF_2$ | $CONH_2$ | Cl | $CF_3$ |
| $CH_2CH_2CBrF_2$ | $CONH_2$ | Cl | $CF_2CF_3$ |
| $CH_2CH_2CBrF_2$ | $CONH_2$ | Cl | $CF_2CF_2CF_3$ |

TABLE 25

| R¹ | R² | R³ | R⁴ |
|---|---|---|---|
| $CH_2CH_2CBrF_2$ | $CONH(CH_3)$ | H | $CF_3$ |
| $CH_2CH_2CBrF_2$ | $CONH(CH_3)$ | H | $CF_2CF_3$ |
| $CH_2CH_2CBrF_2$ | $CONH(CH_3)$ | H | $CF_2CF_2CF_3$ |
| $CH_2CH_2CBrF_2$ | $CONH(CH_3)$ | $CH_3$ | $CF_3$ |
| $CH_2CH_2CBrF_2$ | $CONH(CH_3)$ | $CH_3$ | $CF_2CF_3$ |
| $CH_2CH_2CBrF_2$ | $CONH(CH_3)$ | $CH_3$ | $CF_2CF_2CF_3$ |
| $CH_2CH_2CBrF_2$ | $CONH(CH_3)$ | $CH_2CH_3$ | $CF_3$ |
| $CH_2CH_2CBrF_2$ | $CONH(CH_3)$ | $CH_2CH_3$ | $CF_2CF_3$ |
| $CH_2CH_2CBrF_2$ | $CONH(CH_3)$ | $CH_2CH_3$ | $CF_2CF_2CF_3$ |
| $CH_2CH_2CBrF_2$ | $CONH(CH_3)$ | F | $CF_3$ |
| $CH_2CH_2CBrF_2$ | $CONH(CH_3)$ | F | $CF_2CF_3$ |
| $CH_2CH_2CBrF_2$ | $CONH(CH_3)$ | F | $CF_2CF_2CF_3$ |

TABLE 25-continued

| R¹ | R² | R³ | R⁴ |
|---|---|---|---|
| CH₂CH₂CBrF₂ | CONH(CH₃) | Cl | CF₃ |
| CH₂CH₂CBrF₂ | CONH(CH₃) | Cl | CF₂CF₃ |
| CH₂CH₂CBrF₂ | CONH(CH₃) | Cl | CF₂CF₂CF₃ |
| CH₂CH₂CBrF₂ | CONH(CH₂CH₃) | H | CF₃ |
| CH₂CH₂CBrF₂ | CONH(CH₂CH₃) | H | CF₂CF₃ |
| CH₂CH₂CBrF₂ | CONH(CH₂CH₃) | H | CF₂CF₂CF₃ |
| CH₂CH₂CBrF₂ | CONH(CH₂CH₃) | CH₃ | CF₃ |
| CH₂CH₂CBrF₂ | CONH(CH₂CH₃) | CH₃ | CF₂CF₃ |
| CH₂CH₂CBrF₂ | CONH(CH₂CH₃) | CH₃ | CF₂CF₂CF₃ |
| CH₂CH₂CBrF₂ | CONH(CH₂CH₃) | CH₂CH₃ | CF₃ |
| CH₂CH₂CBrF₂ | CONH(CH₂CH₃) | CH₂CH₃ | CF₂CF₃ |
| CH₂CH₂CBrF₂ | CONH(CH₂CH₃) | CH₂CH₃ | CF₂CF₂CF₃ |
| CH₂CH₂CBrF₂ | CONH(CH₂CH₃) | F | CF₃ |
| CH₂CH₂CBrF₂ | CONH(CH₂CH₃) | F | CF₂CF₃ |
| CH₂CH₂CBrF₂ | CONH(CH₂CH₃) | F | CF₂CF₂CF₃ |
| CH₂CH₂CBrF₂ | CONH(CH₂CH₃) | Cl | CF₃ |
| CH₂CH₂CBrF₂ | CONH(CH₂CH₃) | Cl | CF₂CF₃ |
| CH₂CH₂CBrF₂ | CONH(CH₂CH₃) | Cl | CF₂CF₂CF₃ |

TABLE 26

| R¹ | R² | R³ | R⁴ |
|---|---|---|---|
| CH₂CH₂CBrF₂ | CON(CH₃)₂ | H | CF₃ |
| CH₂CH₂CBrF₂ | CON(CH₃)₂ | H | CF₂CF₃ |
| CH₂CH₂CBrF₂ | CON(CH₃)₂ | H | CF₂CF₂CF₃ |
| CH₂CH₂CBrF₂ | CON(CH₃)₂ | CH₃ | CF₃ |
| CH₂CH₂CBrF₂ | CON(CH₃)₂ | CH₃ | CF₂CF₃ |
| CH₂CH₂CBrF₂ | CON(CH₃)₂ | CH₃ | CF₂CF₂CF₃ |
| CH₂CH₂CBrF₂ | CON(CH₃)₂ | CH₂CH₃ | CF₃ |
| CH₂CH₂CBrF₂ | CON(CH₃)₂ | CH₂CH₃ | CF₂CF₃ |
| CH₂CH₂CBrF₂ | CON(CH₃)₂ | CH₂CH₃ | CF₂CF₂CF₃ |
| CH₂CH₂CBrF₂ | CON(CH₃)₂ | F | CF₃ |
| CH₂CH₂CBrF₂ | CON(CH₃)₂ | F | CF₂CF₃ |
| CH₂CH₂CBrF₂ | CON(CH₃)₂ | F | CF₂CF₂CF₃ |
| CH₂CH₂CBrF₂ | CON(CH₃)₂ | Cl | CF₃ |
| CH₂CH₂CBrF₂ | CON(CH₃)₂ | Cl | CF₂CF₃ |
| CH₂CH₂CBrF₂ | CON(CH₃)₂ | Cl | CF₂CF₂CF₃ |
| CH₂CH₂CBrF₂ | C(S)OCH₃ | H | CF₃ |
| CH₂CH₂CBrF₂ | C(S)OCH₃ | H | CF₂CF₃ |
| CH₂CH₂CBrF₂ | C(S)OCH₃ | H | CF₂CF₂CF₃ |
| CH₂CH₂CBrF₂ | C(S)OCH₃ | CH₃ | CF₃ |
| CH₂CH₂CBrF₂ | C(S)OCH₃ | CH₃ | CF₂CF₃ |
| CH₂CH₂CBrF₂ | C(S)OCH₃ | CH₃ | CF₂CF₂CF₃ |
| CH₂CH₂CBrF₂ | C(S)OCH₃ | CH₂CH₃ | CF₃ |
| CH₂CH₂CBrF₂ | C(S)OCH₃ | CH₂CH₃ | CF₂CF₃ |
| CH₂CH₂CBrF₂ | C(S)OCH₃ | CH₂CH₃ | CF₂CF₂CF₃ |
| CH₂CH₂CBrF₂ | C(S)OCH₃ | F | CF₃ |
| CH₂CH₂CBrF₂ | C(S)OCH₃ | F | CF₂CF₃ |
| CH₂CH₂CBrF₂ | C(S)OCH₃ | F | CF₂CF₂CF₃ |
| CH₂CH₂CBrF₂ | C(S)OCH₃ | Cl | CF₃ |
| CH₂CH₂CBrF₂ | C(S)OCH₃ | Cl | CF₂CF₃ |
| CH₂CH₂CBrF₂ | C(S)OCH₃ | Cl | CF₂CF₂CF₃ |

TABLE 27

| R¹ | R² | R³ | R⁴ |
|---|---|---|---|
| CH₂CH₂CBrF₂ | C(S)NH₂ | H | CF₃ |
| CH₂CH₂CBrF₂ | C(S)NH₂ | H | CF₂CF₃ |
| CH₂CH₂CBrF₂ | C(S)NH₂ | H | CF₂CF₂CF₃ |
| CH₂CH₂CBrF₂ | C(S)NH₂ | CH₃ | CF₃ |
| CH₂CH₂CBrF₂ | C(S)NH₂ | CH₃ | CF₂CF₃ |
| CH₂CH₂CBrF₂ | C(S)NH₂ | CH₃ | CF₂CF₂CF₃ |
| CH₂CH₂CBrF₂ | C(S)NH₂ | CH₂CH₃ | CF₃ |
| CH₂CH₂CBrF₂ | C(S)NH₂ | CH₂CH₃ | CF₂CF₃ |
| CH₂CH₂CBrF₂ | C(S)NH₂ | CH₂CH₃ | CF₂CF₂CF₃ |
| CH₂CH₂CBrF₂ | C(S)NH₂ | F | CF₃ |
| CH₂CH₂CBrF₂ | C(S)NH₂ | F | CF₂CF₃ |
| CH₂CH₂CBrF₂ | C(S)NH₂ | F | CF₂CF₂CF₃ |
| CH₂CH₂CBrF₂ | C(S)NH₂ | Cl | CF₃ |
| CH₂CH₂CBrF₂ | C(S)NH₂ | Cl | CF₂CF₃ |
| CH₂CH₂CBrF₂ | C(S)NH₂ | Cl | CF₂CF₂CF₃ |

TABLE 27-continued

| R¹ | R² | R³ | R⁴ |
|---|---|---|---|
| CH₂CH₂CBrF₂ | C(S)NH(CH₃) | H | CF₃ |
| CH₂CH₂CBrF₂ | C(S)NH(CH₃) | H | CF₂CF₃ |
| CH₂CH₂CBrF₂ | C(S)NH(CH₃) | H | CF₂CF₂CF₃ |
| CH₂CH₂CBrF₂ | C(S)NH(CH₃) | CH₃ | CF₃ |
| CH₂CH₂CBrF₂ | C(S)NH(CH₃) | CH₃ | CF₂CF₃ |
| CH₂CH₂CBrF₂ | C(S)NH(CH₃) | CH₃ | CF₂CF₂CF₃ |
| CH₂CH₂CBrF₂ | C(S)NH(CH₃) | CH₂CH₃ | CF₃ |
| CH₂CH₂CBrF₂ | C(S)NH(CH₃) | CH₂CH₃ | CF₂CF₃ |
| CH₂CH₂CBrF₂ | C(S)NH(CH₃) | CH₂CH₃ | CF₂CF₂CF₃ |
| CH₂CH₂CBrF₂ | C(S)NH(CH₃) | F | CF₃ |
| CH₂CH₂CBrF₂ | C(S)NH(CH₃) | F | CF₂CF₃ |
| CH₂CH₂CBrF₂ | C(S)NH(CH₃) | F | CF₂CF₂CF₃ |
| CH₂CH₂CBrF₂ | C(S)NH(CH₃) | Cl | CF₃ |
| CH₂CH₂CBrF₂ | C(S)NH(CH₃) | Cl | CF₂CF₃ |
| CH₂CH₂CBrF₂ | C(S)NH(CH₃) | Cl | CF₂CF₂CF₃ |

TABLE 28

| R¹ | R² | R³ | R⁴ |
|---|---|---|---|
| CH₂CH₂CBrF₂ | C(S)N(CH₃)₂ | H | CF₃ |
| CH₂CH₂CBrF₂ | C(S)N(CH₃)₂ | H | CF₂CF₃ |
| CH₂CH₂CBrF₂ | C(S)N(CH₃)₂ | H | CF₂CF₂CF₃ |
| CH₂CH₂CBrF₂ | C(S)N(CH₃)₂ | CH₃ | CF₃ |
| CH₂CH₂CBrF₂ | C(S)N(CH₃)₂ | CH₃ | CF₂CF₃ |
| CH₂CH₂CBrF₂ | C(S)N(CH₃)₂ | CH₃ | CF₂CF₂CF₃ |
| CH₂CH₂CBrF₂ | C(S)N(CH₃)₂ | CH₂CH₃ | CF₃ |
| CH₂CH₂CBrF₂ | C(S)N(CH₃)₂ | CH₂CH₃ | CF₂CF₃ |
| CH₂CH₂CBrF₂ | C(S)N(CH₃)₂ | CH₂CH₃ | CF₂CF₂CF₃ |
| CH₂CH₂CBrF₂ | C(S)N(CH₃)₂ | F | CF₃ |
| CH₂CH₂CBrF₂ | C(S)N(CH₃)₂ | F | CF₂CF₃ |
| CH₂CH₂CBrF₂ | C(S)N(CH₃)₂ | F | CF₂CF₂CF₃ |
| CH₂CH₂CBrF₂ | C(S)N(CH₃)₂ | Cl | CF₃ |
| CH₂CH₂CBrF₂ | C(S)N(CH₃)₂ | Cl | CF₂CF₃ |
| CH₂CH₂CBrF₂ | C(S)N(CH₃)₂ | Cl | CF₂CF₂CF₃ |
| CH₂CH₂CH₂CBrF₂ | CN | H | CF₃ |
| CH₂CH₂CH₂CBrF₂ | CN | H | CF₂CF₃ |
| CH₂CH₂CH₂CBrF₂ | CN | H | CF₂CF₂CF₃ |
| CH₂CH₂CH₂CBrF₂ | CN | CH₃ | CF₃ |
| CH₂CH₂CH₂CBrF₂ | CN | CH₃ | CF₂CF₃ |
| CH₂CH₂CH₂CBrF₂ | CN | CH₃ | CF₂CF₂CF₃ |
| CH₂CH₂CH₂CBrF₂ | CN | CH₂CH₃ | CF₃ |
| CH₂CH₂CH₂CBrF₂ | CN | CH₂CH₃ | CF₂CF₃ |
| CH₂CH₂CH₂CBrF₂ | CN | CH₂CH₃ | CF₂CF₂CF₃ |
| CH₂CH₂CH₂CBrF₂ | CN | F | CF₃ |
| CH₂CH₂CH₂CBrF₂ | CN | F | CF₂CF₃ |
| CH₂CH₂CH₂CBrF₂ | CN | F | CF₂CF₂CF₃ |
| CH₂CH₂CH₂CBrF₂ | CN | Cl | CF₃ |
| CH₂CH₂CH₂CBrF₂ | CN | Cl | CF₂CF₃ |
| CH₂CH₂CH₂CBrF₂ | CN | Cl | CF₂CF₂CF₃ |

TABLE 29

| R¹ | R² | R³ | R⁴ |
|---|---|---|---|
| CH₂CH₂CH₂CBrF₂ | CO₂CH₃ | H | CF₃ |
| CH₂CH₂CH₂CBrF₂ | CO₂CH₃ | H | CF₂CF₃ |
| CH₂CH₂CH₂CBrF₂ | CO₂CH₃ | H | CF₂CF₂CF₃ |
| CH₂CH₂CH₂CBrF₂ | CO₂CH₃ | CH₃ | CF₃ |
| CH₂CH₂CH₂CBrF₂ | CO₂CH₃ | CH₃ | CF₂CF₃ |
| CH₂CH₂CH₂CBrF₂ | CO₂CH₃ | CH₃ | CF₂CF₂CF₃ |
| CH₂CH₂CH₂CBrF₂ | CO₂CH₃ | CH₂CH₃ | CF₃ |
| CH₂CH₂CH₂CBrF₂ | CO₂CH₃ | CH₂CH₃ | CF₂CF₃ |
| CH₂CH₂CH₂CBrF₂ | CO₂CH₃ | CH₂CH₃ | CF₂CF₂CF₃ |
| CH₂CH₂CH₂CBrF₂ | CO₂CH₃ | F | CF₃ |
| CH₂CH₂CH₂CBrF₂ | CO₂CH₃ | F | CF₂CF₃ |
| CH₂CH₂CH₂CBrF₂ | CO₂CH₃ | F | CF₂CF₂CF₃ |
| CH₂CH₂CH₂CBrF₂ | CO₂CH₃ | Cl | CF₃ |
| CH₂CH₂CH₂CBrF₂ | CO₂CH₃ | Cl | CF₂CF₃ |
| CH₂CH₂CH₂CBrF₂ | CO₂CH₃ | Cl | CF₂CF₂CF₃ |
| CH₂CH₂CH₂CBrF₂ | CO₂C(CH₃)₃ | H | CF₃ |
| CH₂CH₂CH₂CBrF₂ | CO₂C(CH₃)₃ | H | CF₂CF₃ |
| CH₂CH₂CH₂CBrF₂ | CO₂C(CH₃)₃ | H | CF₂CF₂CF₃ |

TABLE 29-continued

| R¹ | R² | R³ | R⁴ |
| --- | --- | --- | --- |
| CH₂CH₂CH₂CBrF₂ | CO₂C(CH₃)₃ | CH₃ | CF₃ |
| CH₂CH₂CH₂CBrF₂ | CO₂C(CH₃)₃ | CH₃ | CF₂CF₃ |
| CH₂CH₂CH₂CBrF₂ | CO₂C(CH₃)₃ | CH₃ | CF₂CF₂CF₃ |
| CH₂CH₂CH₂CBrF₂ | CO₂C(CH₃)₃ | CH₂CH₃ | CF₃ |
| CH₂CH₂CH₂CBrF₂ | CO₂C(CH₃)₃ | CH₂CH₃ | CF₂CF₃ |
| CH₂CH₂CH₂CBrF₂ | CO₂C(CH₃)₃ | CH₂CH₃ | CF₂CF₂CF₃ |
| CH₂CH₂CH₂CBrF₂ | CO₂C(CH₃)₃ | F | CF₃ |
| CH₂CH₂CH₂CBrF₂ | CO₂C(CH₃)₃ | F | CF₂CF₃ |
| CH₂CH₂CH₂CBrF₂ | CO₂C(CH₃)₃ | F | CF₂CF₂CF₃ |
| CH₂CH₂CH₂CBrF₂ | CO₂C(CH₃)₃ | Cl | CF₃ |
| CH₂CH₂CH₂CBrF₂ | CO₂C(CH₃)₃ | Cl | CF₂CF₃ |
| CH₂CH₂CH₂CBrF₂ | CO₂C(CH₃)₃ | Cl | CF₂CF₂CF₃ |

TABLE 30

| R¹ | R² | R³ | R⁴ |
| --- | --- | --- | --- |
| CH₂CH₂CH₂CBrF₂ | CONH₂ | H | CF₃ |
| CH₂CH₂CH₂CBrF₂ | CONH₂ | H | CF₂CF₃ |
| CH₂CH₂CH₂CBrF₂ | CONH₂ | H | CF₂CF₂CF₃ |
| CH₂CH₂CH₂CBrF₂ | CONH₂ | CH₃ | CF₃ |
| CH₂CH₂CH₂CBrF₂ | CONH₂ | CH₃ | CF₂CF₃ |
| CH₂CH₂CH₂CBrF₂ | CONH₂ | CH₃ | CF₂CF₂CF₃ |
| CH₂CH₂CH₂CBrF₂ | CONH₂ | CH₂CH₃ | CF₃ |
| CH₂CH₂CH₂CBrF₂ | CONH₂ | CH₂CH₃ | CF₂CF₃ |
| CH₂CH₂CH₂CBrF₂ | CONH₂ | CH₂CH₃ | CF₂CF₂CF₃ |
| CH₂CH₂CH₂CBrF₂ | CONH₂ | F | CF₃ |
| CH₂CH₂CH₂CBrF₂ | CONH₂ | F | CF₂CF₃ |
| CH₂CH₂CH₂CBrF₂ | CONH₂ | F | CF₂CF₂CF₃ |
| CH₂CH₂CH₂CBrF₂ | CONH₂ | Cl | CF₃ |
| CH₂CH₂CH₂CBrF₂ | CONH₂ | Cl | CF₂CF₃ |
| CH₂CH₂CH₂CBrF₂ | CONH₂ | Cl | CF₂CF₂CF₃ |
| CH₂CH₂CH₂CBrF₂ | CONH(CH₃) | H | CF₃ |
| CH₂CH₂CH₂CBrF₂ | CONH(CH₃) | H | CF₂CF₃ |
| CH₂CH₂CH₂CBrF₂ | CONH(CH₃) | H | CF₂CF₂CF₃ |
| CH₂CH₂CH₂CBrF₂ | CONH(CH₃) | CH₃ | CF₃ |
| CH₂CH₂CH₂CBrF₂ | CONH(CH₃) | CH₃ | CF₂CF₃ |
| CH₂CH₂CH₂CBrF₂ | CONH(CH₃) | CH₃ | CF₂CF₂CF₃ |
| CH₂CH₂CH₂CBrF₂ | CONH(CH₃) | CH₂CH₃ | CF₃ |
| CH₂CH₂CH₂CBrF₂ | CONH(CH₃) | CH₂CH₃ | CF₂CF₃ |
| CH₂CH₂CH₂CBrF₂ | CONH(CH₃) | CH₂CH₃ | CF₂CF₂CF₃ |
| CH₂CH₂CH₂CBrF₂ | CONH(CH₃) | F | CF₃ |
| CH₂CH₂CH₂CBrF₂ | CONH(CH₃) | F | CF₂CF₃ |
| CH₂CH₂CH₂CBrF₂ | CONH(CH₃) | F | CF₂CF₂CF₃ |
| CH₂CH₂CH₂CBrF₂ | CONH(CH₃) | Cl | CF₃ |
| CH₂CH₂CH₂CBrF₂ | CONH(CH₃) | Cl | CF₂CF₃ |
| CH₂CH₂CH₂CBrF₂ | CONH(CH₃) | Cl | CF₂CF₂CF₃ |

TABLE 31

| R¹ | R² | R³ | R⁴ |
| --- | --- | --- | --- |
| CH₂CH₂CH₂CBrF₂ | CONH(CH₂CH₃) | H | CF₃ |
| CH₂CH₂CH₂CBrF₂ | CONH(CH₂CH₃) | H | CF₂CF₃ |
| CH₂CH₂CH₂CBrF₂ | CONH(CH₂CH₃) | H | CF₂CF₂CF₃ |
| CH₂CH₂CH₂CBrF₂ | CONH(CH₂CH₃) | CH₃ | CF₃ |
| CH₂CH₂CH₂CBrF₂ | CONH(CH₂CH₃) | CH₃ | CF₂CF₃ |
| CH₂CH₂CH₂CBrF₂ | CONH(CH₂CH₃) | CH₃ | CF₂CF₂CF₃ |
| CH₂CH₂CH₂CBrF₂ | CONH(CH₂CH₃) | CH₂CH₃ | CF₃ |
| CH₂CH₂CH₂CBrF₂ | CONH(CH₂CH₃) | CH₂CH₃ | CF₂CF₃ |
| CH₂CH₂CH₂CBrF₂ | CONH(CH₂CH₃) | CH₂CH₃ | CF₂CF₂CF₃ |
| CH₂CH₂CH₂CBrF₂ | CONH(CH₂CH₃) | F | CF₃ |
| CH₂CH₂CH₂CBrF₂ | CONH(CH₂CH₃) | F | CF₂CF₃ |
| CH₂CH₂CH₂CBrF₂ | CONH(CH₂CH₃) | F | CF₂CF₂CF₃ |
| CH₂CH₂CH₂CBrF₂ | CONH(CH₂CH₃) | Cl | CF₃ |
| CH₂CH₂CH₂CBrF₂ | CONH(CH₂CH₃) | Cl | CF₂CF₃ |
| CH₂CH₂CH₂CBrF₂ | CONH(CH₂CH₃) | Cl | CF₂CF₂CF₃ |
| CH₂CH₂CH₂CBrF₂ | CON(CH₃)₂ | H | CF₃ |
| CH₂CH₂CH₂CBrF₂ | CON(CH₃)₂ | H | CF₂CF₃ |
| CH₂CH₂CH₂CBrF₂ | CON(CH₃)₂ | H | CF₂CF₂CF₃ |
| CH₂CH₂CH₂CBrF₂ | CON(CH₃)₂ | CH₃ | CF₃ |
| CH₂CH₂CH₂CBrF₂ | CON(CH₃)₂ | CH₃ | CF₂CF₃ |
| CH₂CH₂CH₂CBrF₂ | CON(CH₃)₂ | CH₃ | CF₂CF₂CF₃ |
| CH₂CH₂CH₂CBrF₂ | CON(CH₃)₂ | CH₂CH₃ | CF₃ |
| CH₂CH₂CH₂CBrF₂ | CON(CH₃)₂ | CH₂CH₃ | CF₂CF₃ |
| CH₂CH₂CH₂CBrF₂ | CON(CH₃)₂ | CH₂CH₃ | CF₂CF₂CF₃ |
| CH₂CH₂CH₂CBrF₂ | CON(CH₃)₂ | F | CF₃ |
| CH₂CH₂CH₂CBrF₂ | CON(CH₃)₂ | F | CF₂CF₃ |
| CH₂CH₂CH₂CBrF₂ | CON(CH₃)₂ | F | CF₂CF₂CF₃ |
| CH₂CH₂CH₂CBrF₂ | CON(CH₃)₂ | Cl | CF₃ |
| CH₂CH₂CH₂CBrF₂ | CON(CH₃)₂ | Cl | CF₂CF₃ |
| CH₂CH₂CH₂CBrF₂ | CON(CH₃)₂ | Cl | CF₂CF₂CF₃ |

TABLE 32

| R¹ | R² | R³ | R⁴ |
| --- | --- | --- | --- |
| CH₂CH₂CH₂CBrF₂ | C(S)OCH₃ | H | CF₃ |
| CH₂CH₂CH₂CBrF₂ | C(S)OCH₃ | H | CF₂CF₃ |
| CH₂CH₂CH₂CBrF₂ | C(S)OCH₃ | H | CF₂CF₂CF₃ |
| CH₂CH₂CH₂CBrF₂ | C(S)OCH₃ | CH₃ | CF₃ |
| CH₂CH₂CH₂CBrF₂ | C(S)OCH₃ | CH₃ | CF₂CF₃ |
| CH₂CH₂CH₂CBrF₂ | C(S)OCH₃ | CH₃ | CF₂CF₂CF₃ |
| CH₂CH₂CH₂CBrF₂ | C(S)OCH₃ | CH₂CH₃ | CF₃ |
| CH₂CH₂CH₂CBrF₂ | C(S)OCH₃ | CH₂CH₃ | CF₂CF₃ |
| CH₂CH₂CH₂CBrF₂ | C(S)OCH₃ | CH₂CH₃ | CF₂CF₂CF₃ |
| CH₂CH₂CH₂CBrF₂ | C(S)OCH₃ | F | CF₃ |
| CH₂CH₂CH₂CBrF₂ | C(S)OCH₃ | F | CF₂CF₃ |
| CH₂CH₂CH₂CBrF₂ | C(S)OCH₃ | F | CF₂CF₂CF₃ |
| CH₂CH₂CH₂CBrF₂ | C(S)OCH₃ | Cl | CF₃ |
| CH₂CH₂CH₂CBrF₂ | C(S)OCH₃ | Cl | CF₂CF₃ |
| CH₂CH₂CH₂CBrF₂ | C(S)OCH₃ | Cl | CF₂CF₂CF₃ |
| CH₂CH₂CH₂CBrF₂ | C(S)NH₂ | H | CF₃ |
| CH₂CH₂CH₂CBrF₂ | C(S)NH₂ | H | CF₂CF₃ |
| CH₂CH₂CH₂CBrF₂ | C(S)NH₂ | H | CF₂CF₂CF₃ |
| CH₂CH₂CH₂CBrF₂ | C(S)NH₂ | CH₃ | CF₃ |
| CH₂CH₂CH₂CBrF₂ | C(S)NH₂ | CH₃ | CF₂CF₃ |
| CH₂CH₂CH₂CBrF₂ | C(S)NH₂ | CH₃ | CF₂CF₂CF₃ |
| CH₂CH₂CH₂CBrF₂ | C(S)NH₂ | CH₂CH₃ | CF₃ |
| CH₂CH₂CH₂CBrF₂ | C(S)NH₂ | CH₂CH₃ | CF₂CF₃ |
| CH₂CH₂CH₂CBrF₂ | C(S)NH₂ | CH₂CH₃ | CF₂CF₂CF₃ |
| CH₂CH₂CH₂CBrF₂ | C(S)NH₂ | F | CF₃ |
| CH₂CH₂CH₂CBrF₂ | C(S)NH₂ | F | CF₂CF₃ |
| CH₂CH₂CH₂CBrF₂ | C(S)NH₂ | F | CF₂CF₂CF₃ |
| CH₂CH₂CH₂CBrF₂ | C(S)NH₂ | Cl | CF₃ |
| CH₂CH₂CH₂CBrF₂ | C(S)NH₂ | Cl | CF₂CF₃ |
| CH₂CH₂CH₂CBrF₂ | C(S)NH₂ | Cl | CF₂CF₂CF₃ |

TABLE 33

| R¹ | R² | R³ | R⁴ |
| --- | --- | --- | --- |
| CH₂CH₂CH₂CBrF₂ | C(S)NH(CH₃) | H | CF₃ |
| CH₂CH₂CH₂CBrF₂ | C(S)NH(CH₃) | H | CF₂CF₃ |
| CH₂CH₂CH₂CBrF₂ | C(S)NH(CH₃) | H | CF₂CF₂CF₃ |
| CH₂CH₂CH₂CBrF₂ | C(S)NH(CH₃) | CH₃ | CF₃ |
| CH₂CH₂CH₂CBrF₂ | C(S)NH(CH₃) | CH₃ | CF₂CF₃ |
| CH₂CH₂CH₂CBrF₂ | C(S)NH(CH₃) | CH₃ | CF₂CF₂CF₃ |
| CH₂CH₂CH₂CBrF₂ | C(S)NH(CH₃) | CH₂CH₃ | CF₃ |
| CH₂CH₂CH₂CBrF₂ | C(S)NH(CH₃) | CH₂CH₃ | CF₂CF₃ |
| CH₂CH₂CH₂CBrF₂ | C(S)NH(CH₃) | CH₂CH₃ | CF₂CF₂CF₃ |
| CH₂CH₂CH₂CBrF₂ | C(S)NH(CH₃) | F | CF₃ |
| CH₂CH₂CH₂CBrF₂ | C(S)NH(CH₃) | F | CF₂CF₃ |
| CH₂CH₂CH₂CBrF₂ | C(S)NH(CH₃) | F | CF₂CF₂CF₃ |
| CH₂CH₂CH₂CBrF₂ | C(S)NH(CH₃) | Cl | CF₃ |
| CH₂CH₂CH₂CBrF₂ | C(S)NH(CH₃) | Cl | CF₂CF₃ |
| CH₂CH₂CH₂CBrF₂ | C(S)NH(CH₃) | Cl | CF₂CF₂CF₃ |
| CH₂CH₂CH₂CBrF₂ | C(S)N(CH₃)₂ | H | CF₃ |
| CH₂CH₂CH₂CBrF₂ | C(S)N(CH₃)₂ | H | CF₂CF₃ |
| CH₂CH₂CH₂CBrF₂ | C(S)N(CH₃)₂ | H | CF₂CF₂CF₃ |
| CH₂CH₂CH₂CBrF₂ | C(S)N(CH₃)₂ | CH₃ | CF₃ |
| CH₂CH₂CH₂CBrF₂ | C(S)N(CH₃)₂ | CH₃ | CF₂CF₃ |
| CH₂CH₂CH₂CBrF₂ | C(S)N(CH₃)₂ | CH₃ | CF₂CF₂CF₃ |
| CH₂CH₂CH₂CBrF₂ | C(S)N(CH₃)₂ | CH₂CH₃ | CF₃ |
| CH₂CH₂CH₂CBrF₂ | C(S)N(CH₃)₂ | CH₂CH₃ | CF₂CF₃ |
| CH₂CH₂CH₂CBrF₂ | C(S)N(CH₃)₂ | CH₂CH₃ | CF₂CF₂CF₃ |

TABLE 33-continued

| R¹ | R² | R³ | R⁴ |
|---|---|---|---|
| CH₂CH₂CH₂CBrF₂ | C(S)N(CH₃)₂ | F | CF₃ |
| CH₂CH₂CH₂CBrF₂ | C(S)N(CH₃)₂ | F | CF₂CF₃ |
| CH₂CH₂CH₂CBrF₂ | C(S)N(CH₃)₂ | F | CF₂CF₂CF₃ |
| CH₂CH₂CH₂CBrF₂ | C(S)N(CH₃)₂ | Cl | CF₃ |
| CH₂CH₂CH₂CBrF₂ | C(S)N(CH₃)₂ | Cl | CF₂CF₃ |
| CH₂CH₂CH₂CBrF₂ | C(S)N(CH₃)₂ | Cl | CF₂CF₂CF₃ |

TABLE 34

| R¹ | R² | R³ | R⁴ |
|---|---|---|---|
| CH₂CH₂CH₂CClFCClF₂ | CN | H | CF₃ |
| CH₂CH₂CH₂CClFCClF₂ | CN | H | CF₂CF₃ |
| CH₂CH₂CH₂CClFCClF₂ | CN | H | CF₂CF₂CF₃ |
| CH₂CH₂CH₂CClFCClF₂ | CN | CH₃ | CF₃ |
| CH₂CH₂CH₂CClFCClF₂ | CN | CH₃ | CF₂CF₃ |
| CH₂CH₂CH₂CClFCClF₂ | CN | CH₃ | CF₂CF₂CF₃ |
| CH₂CH₂CH₂CClFCClF₂ | CN | CH₂CH₃ | CF₃ |
| CH₂CH₂CH₂CClFCClF₂ | CN | CH₂CH₃ | CF₂CF₃ |
| CH₂CH₂CH₂CClFCClF₂ | CN | CH₂CH₃ | CF₂CF₂CF₃ |
| CH₂CH₂CH₂CClFCClF₂ | CN | F | CF₃ |
| CH₂CH₂CH₂CClFCClF₂ | CN | F | CF₂CF₃ |
| CH₂CH₂CH₂CClFCClF₂ | CN | F | CF₂CF₂CF₃ |
| CH₂CH₂CH₂CClFCClF₂ | CN | Cl | CF₃ |
| CH₂CH₂CH₂CClFCClF₂ | CN | Cl | CF₂CF₃ |
| CH₂CH₂CH₂CClFCClF₂ | CN | Cl | CF₂CF₂CF₃ |
| CH₂CH₂CH₂CClFCClF₂ | CO₂CH₃ | H | CF₃ |
| CH₂CH₂CH₂CClFCClF₂ | CO₂CH₃ | H | CF₂CF₃ |
| CH₂CH₂CH₂CClFCClF₂ | CO₂CH₃ | H | CF₂CF₂CF₃ |
| CH₂CH₂CH₂CClFCClF₂ | CO₂CH₃ | CH₃ | CF₃ |
| CH₂CH₂CH₂CClFCClF₂ | CO₂CH₃ | CH₃ | CF₂CF₃ |
| CH₂CH₂CH₂CClFCClF₂ | CO₂CH₃ | CH₃ | CF₂CF₂CF₃ |
| CH₂CH₂CH₂CClFCClF₂ | CO₂CH₃ | CH₂CH₃ | CF₃ |
| CH₂CH₂CH₂CClFCClF₂ | CO₂CH₃ | CH₂CH₃ | CF₂CF₃ |
| CH₂CH₂CH₂CClFCClF₂ | CO₂CH₃ | CH₂CH₃ | CF₂CF₂CF₃ |
| CH₂CH₂CH₂CClFCClF₂ | CO₂CH₃ | F | CF₃ |
| CH₂CH₂CH₂CClFCClF₂ | CO₂CH₃ | F | CF₂CF₃ |
| CH₂CH₂CH₂CClFCClF₂ | CO₂CH₃ | F | CF₂CF₂CF₃ |
| CH₂CH₂CH₂CClFCClF₂ | CO₂CH₃ | Cl | CF₃ |
| CH₂CH₂CH₂CClFCClF₂ | CO₂CH₃ | Cl | CF₂CF₃ |
| CH₂CH₂CH₂CClFCClF₂ | CO₂CH₃ | Cl | CF₂CF₂CF₃ |

TABLE 35

| R¹ | R² | R³ | R⁴ |
|---|---|---|---|
| CH₂CH₂CH₂CClFCClF₂ | CO₂C(CH₃)₃ | H | CF₃ |
| CH₂CH₂CH₂CClFCClF₂ | CO₂C(CH₃)₃ | H | CF₂CF₃ |
| CH₂CH₂CH₂CClFCClF₂ | CO₂C(CH₃)₃ | H | CF₂CF₂CF₃ |
| CH₂CH₂CH₂CClFCClF₂ | CO₂C(CH₃)₃ | CH₃ | CF₃ |
| CH₂CH₂CH₂CClFCClF₂ | CO₂C(CH₃)₃ | CH₃ | CF₂CF₃ |
| CH₂CH₂CH₂CClFCClF₂ | CO₂C(CH₃)₃ | CH₃ | CF₂CF₂CF₃ |
| CH₂CH₂CH₂CClFCClF₂ | CO₂C(CH₃)₃ | CH₂CH₃ | CF₃ |
| CH₂CH₂CH₂CClFCClF₂ | CO₂C(CH₃)₃ | CH₂CH₃ | CF₂CF₃ |
| CH₂CH₂CH₂CClFCClF₂ | CO₂C(CH₃)₃ | CH₂CH₃ | CF₂CF₂CF₃ |
| CH₂CH₂CH₂CClFCClF₂ | CO₂C(CH₃)₃ | F | CF₃ |
| CH₂CH₂CH₂CClFCClF₂ | CO₂C(CH₃)₃ | F | CF₂CF₃ |
| CH₂CH₂CH₂CClFCClF₂ | CO₂C(CH₃)₃ | F | CF₂CF₂CF₃ |
| CH₂CH₂CH₂CClFCClF₂ | CO₂C(CH₃)₃ | Cl | CF₃ |
| CH₂CH₂CH₂CClFCClF₂ | CO₂C(CH₃)₃ | Cl | CF₂CF₃ |
| CH₂CH₂CH₂CClFCClF₂ | CO₂C(CH₃)₃ | Cl | CF₂CF₂CF₃ |
| CH₂CH₂CH₂CClFCClF₂ | CONH₂ | H | CF₃ |
| CH₂CH₂CH₂CClFCClF₂ | CONH₂ | H | CF₂CF₃ |
| CH₂CH₂CH₂CClFCClF₂ | CONH₂ | H | CF₂CF₂CF₃ |
| CH₂CH₂CH₂CClFCClF₂ | CONH₂ | CH₃ | CF₃ |
| CH₂CH₂CH₂CClFCClF₂ | CONH₂ | CH₃ | CF₂CF₃ |
| CH₂CH₂CH₂CClFCClF₂ | CONH₂ | CH₃ | CF₂CF₂CF₃ |
| CH₂CH₂CH₂CClFCClF₂ | CONH₂ | CH₂CH₃ | CF₃ |
| CH₂CH₂CH₂CClFCClF₂ | CONH₂ | CH₂CH₃ | CF₂CF₃ |
| CH₂CH₂CH₂CClFCClF₂ | CONH₂ | CH₂CH₃ | CF₂CF₂CF₃ |
| CH₂CH₂CH₂CClFCClF₂ | CONH₂ | F | CF₃ |
| CH₂CH₂CH₂CClFCClF₂ | CONH₂ | F | CF₂CF₃ |
| CH₂CH₂CH₂CClFCClF₂ | CONH₂ | F | CF₂CF₂CF₃ |

TABLE 35-continued

| R¹ | R² | R³ | R⁴ |
|---|---|---|---|
| CH₂CH₂CH₂CClFCClF₂ | CONH₂ | Cl | CF₃ |
| CH₂CH₂CH₂CClFCClF₂ | CONH₂ | Cl | CF₂CF₃ |
| CH₂CH₂CH₂CClFCClF₂ | CONH₂ | Cl | CF₂CF₂CF₃ |

TABLE 36

| R¹ | R² | R³ | R⁴ |
|---|---|---|---|
| CH₂CH₂CH₂CClFCClF₂ | CONH(CH₃) | H | CF₃ |
| CH₂CH₂CH₂CClFCClF₂ | CONH(CH₃) | H | CF₂CF₃ |
| CH₂CH₂CH₂CClFCClF₂ | CONH(CH₃) | H | CF₂CF₂CF₃ |
| CH₂CH₂CH₂CClFCClF₂ | CONH(CH₃) | CH₃ | CF₃ |
| CH₂CH₂CH₂CClFCClF₂ | CONH(CH₃) | CH₃ | CF₂CF₃ |
| CH₂CH₂CH₂CClFCClF₂ | CONH(CH₃) | CH₃ | CF₂CF₂CF₃ |
| CH₂CH₂CH₂CClFCClF₂ | CONH(CH₃) | CH₂CH₃ | CF₃ |
| CH₂CH₂CH₂CClFCClF₂ | CONH(CH₃) | CH₂CH₃ | CF₂CF₃ |
| CH₂CH₂CH₂CClFCClF₂ | CONH(CH₃) | CH₂CH₃ | CF₂CF₂CF₃ |
| CH₂CH₂CH₂CClFCClF₂ | CONH(CH₃) | F | CF₃ |
| CH₂CH₂CH₂CClFCClF₂ | CONH(CH₃) | F | CF₂CF₃ |
| CH₂CH₂CH₂CClFCClF₂ | CONH(CH₃) | F | CF₂CF₂CF₃ |
| CH₂CH₂CH₂CClFCClF₂ | CONH(CH₃) | Cl | CF₃ |
| CH₂CH₂CH₂CClFCClF₂ | CONH(CH₃) | Cl | CF₂CF₃ |
| CH₂CH₂CH₂CClFCClF₂ | CONH(CH₃) | Cl | CF₂CF₂CF₃ |
| CH₂CH₂CH₂CClFCClF₂ | CONH(CH₂CH₃) | H | CF₃ |
| CH₂CH₂CH₂CClFCClF₂ | CONH(CH₂CH₃) | H | CF₂CF₃ |
| CH₂CH₂CH₂CClFCClF₂ | CONH(CH₂CH₃) | H | CF₂CF₂CF₃ |
| CH₂CH₂CH₂CClFCClF₂ | CONH(CH₂CH₃) | CH₃ | CF₃ |
| CH₂CH₂CH₂CClFCClF₂ | CONH(CH₂CH₃) | CH₃ | CF₂CF₃ |
| CH₂CH₂CH₂CClFCClF₂ | CONH(CH₂CH₃) | CH₃ | CF₂CF₂CF₃ |
| CH₂CH₂CH₂CClFCClF₂ | CONH(CH₂CH₃) | CH₂CH₃ | CF₃ |
| CH₂CH₂CH₂CClFCClF₂ | CONH(CH₂CH₃) | CH₂CH₃ | CF₂CF₃ |
| CH₂CH₂CH₂CClFCClF₂ | CONH(CH₂CH₃) | CH₂CH₃ | CF₂CF₂CF₃ |
| CH₂CH₂CH₂CClFCClF₂ | CONH(CH₂CH₃) | F | CF₃ |
| CH₂CH₂CH₂CClFCClF₂ | CONH(CH₂CH₃) | F | CF₂CF₃ |
| CH₂CH₂CH₂CClFCClF₂ | CONH(CH₂CH₃) | F | CF₂CF₂CF₃ |
| CH₂CH₂CH₂CClFCClF₂ | CONH(CH₂CH₃) | Cl | CF₃ |
| CH₂CH₂CH₂CClFCClF₂ | CONH(CH₂CH₃) | Cl | CF₂CF₃ |
| CH₂CH₂CH₂CClFCClF₂ | CONH(CH₂CH₃) | Cl | CF₂CF₂CF₃ |

TABLE 37

| R¹ | R² | R³ | R⁴ |
|---|---|---|---|
| CH₂CH₂CH₂CClFCClF₂ | CON(CH₃)₂ | H | CF₃ |
| CH₂CH₂CH₂CClFCClF₂ | CON(CH₃)₂ | H | CF₂CF₃ |
| CH₂CH₂CH₂CClFCClF₂ | CON(CH₃)₂ | H | CF₂CF₂CF₃ |
| CH₂CH₂CH₂CClFCClF₂ | CON(CH₃)₂ | CH₃ | CF₃ |
| CH₂CH₂CH₂CClFCClF₂ | CON(CH₃)₂ | CH₃ | CF₂CF₃ |
| CH₂CH₂CH₂CClFCClF₂ | CON(CH₃)₂ | CH₃ | CF₂CF₂CF₃ |
| CH₂CH₂CH₂CClFCClF₂ | CON(CH₃)₂ | CH₂CH₃ | CF₃ |
| CH₂CH₂CH₂CClFCClF₂ | CON(CH₃)₂ | CH₂CH₃ | CF₂CF₃ |
| CH₂CH₂CH₂CClFCClF₂ | CON(CH₃)₂ | CH₂CH₃ | CF₂CF₂CF₃ |
| CH₂CH₂CH₂CClFCClF₂ | CON(CH₃)₂ | F | CF₃ |
| CH₂CH₂CH₂CClFCClF₂ | CON(CH₃)₂ | F | CF₂CF₃ |
| CH₂CH₂CH₂CClFCClF₂ | CON(CH₃)₂ | F | CF₂CF₂CF₃ |
| CH₂CH₂CH₂CClFCClF₂ | CON(CH₃)₂ | Cl | CF₃ |
| CH₂CH₂CH₂CClFCClF₂ | CON(CH₃)₂ | Cl | CF₂CF₃ |
| CH₂CH₂CH₂CClFCClF₂ | CON(CH₃)₂ | Cl | CF₂CF₂CF₃ |
| CH₂CH₂CH₂CClFCClF₂ | C(S)OCH₃ | H | CF₃ |
| CH₂CH₂CH₂CClFCClF₂ | C(S)OCH₃ | H | CF₂CF₃ |
| CH₂CH₂CH₂CClFCClF₂ | C(S)OCH₃ | H | CF₂CF₂CF₃ |
| CH₂CH₂CH₂CClFCClF₂ | C(S)OCH₃ | CH₃ | CF₃ |
| CH₂CH₂CH₂CClFCClF₂ | C(S)OCH₃ | CH₃ | CF₂CF₃ |
| CH₂CH₂CH₂CClFCClF₂ | C(S)OCH₃ | CH₃ | CF₂CF₂CF₃ |
| CH₂CH₂CH₂CClFCClF₂ | C(S)OCH₃ | CH₂CH₃ | CF₃ |
| CH₂CH₂CH₂CClFCClF₂ | C(S)OCH₃ | CH₂CH₃ | CF₂CF₃ |
| CH₂CH₂CH₂CClFCClF₂ | C(S)OCH₃ | CH₂CH₃ | CF₂CF₂CF₃ |
| CH₂CH₂CH₂CClFCClF₂ | C(S)OCH₃ | F | CF₃ |
| CH₂CH₂CH₂CClFCClF₂ | C(S)OCH₃ | F | CF₂CF₃ |
| CH₂CH₂CH₂CClFCClF₂ | C(S)OCH₃ | F | CF₂CF₂CF₃ |
| CH₂CH₂CH₂CClFCClF₂ | C(S)OCH₃ | Cl | CF₃ |
| CH₂CH₂CH₂CClFCClF₂ | C(S)OCH₃ | Cl | CF₂CF₃ |
| CH₂CH₂CH₂CClFCClF₂ | C(S)OCH₃ | Cl | CF₂CF₂CF₃ |

TABLE 38

| R¹ | R² | R³ | R⁴ |
|---|---|---|---|
| CH₂CH₂CH₂CClFCClF₂ | C(S)NH₂ | H | CF₃ |
| CH₂CH₂CH₂CClFCClF₂ | C(S)NH₂ | H | CF₂CF₃ |
| CH₂CH₂CH₂CClFCClF₂ | C(S)NH₂ | H | CF₂CF₂CF₃ |
| CH₂CH₂CH₂CClFCClF₂ | C(S)NH₂ | CH₃ | CF₃ |
| CH₂CH₂CH₂CClFCClF₂ | C(S)NH₂ | CH₃ | CF₂CF₃ |
| CH₂CH₂CH₂CClFCClF₂ | C(S)NH₂ | CH₃ | CF₂CF₂CF₃ |
| CH₂CH₂CH₂CClFCClF₂ | C(S)NH₂ | CH₂CH₃ | CF₃ |
| CH₂CH₂CH₂CClFCClF₂ | C(S)NH₂ | CH₂CH₃ | CF₂CF₃ |
| CH₂CH₂CH₂CClFCClF₂ | C(S)NH₂ | CH₂CH₃ | CF₂CF₂CF₃ |
| CH₂CH₂CH₂CClFCClF₂ | C(S)NH₂ | F | CF₃ |
| CH₂CH₂CH₂CClFCClF₂ | C(S)NH₂ | F | CF₂CF₃ |
| CH₂CH₂CH₂CClFCClF₂ | C(S)NH₂ | F | CF₂CF₂CF₃ |
| CH₂CH₂CH₂CBrF₂ | C(S)NH₂ | Cl | CF₃ |
| CH₂CH₂CH₂CBrF₂ | C(S)NH₂ | Cl | CF₂CF₃ |
| CH₂CH₂CH₂CBrF₂ | C(S)NH₂ | Cl | CF₂CF₂CF₃ |
| CH₂CH₂CH₂CBrF₂ | C(S)NH(CH₃) | H | CF₃ |
| CH₂CH₂CH₂CBrF₂ | C(S)NH(CH₃) | H | CF₂CF₃ |
| CH₂CH₂CH₂CBrF₂ | C(S)NH(CH₃) | H | CF₂CF₂CF₃ |
| CH₂CH₂CH₂CBrF₂ | C(S)NH(CH₃) | CH₃ | CF₃ |
| CH₂CH₂CH₂CBrF₂ | C(S)NH(CH₃) | CH₃ | CF₂CF₃ |
| CH₂CH₂CH₂CBrF₂ | C(S)NH(CH₃) | CH₃ | CF₂CF₂CF₃ |
| CH₂CH₂CH₂CBrF₂ | C(S)NH(CH₃) | CH₂CH₃ | CF₃ |
| CH₂CH₂CH₂CBrF₂ | C(S)NH(CH₃) | CH₂CH₃ | CF₂CF₃ |
| CH₂CH₂CH₂CBrF₂ | C(S)NH(CH₃) | CH₂CH₃ | CF₂CF₂CF₃ |
| CH₂CH₂CH₂CBrF₂ | C(S)NH(CH₃) | F | CF₃ |
| CH₂CH₂CH₂CBrF₂ | C(S)NH(CH₃) | F | CF₂CF₃ |
| CH₂CH₂CH₂CBrF₂ | C(S)NH(CH₃) | F | CF₂CF₂CF₃ |
| CH₂CH₂CH₂CBrF₂ | C(S)NH(CH₃) | Cl | CF₃ |
| CH₂CH₂CH₂CBrF₂ | C(S)NH(CH₃) | Cl | CF₂CF₃ |
| CH₂CH₂CH₂CBrF₂ | C(S)NH(CH₃) | Cl | CF₂CF₂CF₃ |

TABLE 39

| R¹ | R² | R³ | R⁴ |
|---|---|---|---|
| CH₂CH₂CH₂CBrF₂ | C(S)N(CH₃)₂ | H | CF₃ |
| CH₂CH₂CH₂CBrF₂ | C(S)N(CH₃)₂ | H | CF₂CF₃ |
| CH₂CH₂CH₂CBrF₂ | C(S)N(CH₃)₂ | H | CF₂CF₂CF₃ |
| CH₂CH₂CH₂CBrF₂ | C(S)N(CH₃)₂ | CH₃ | CF₃ |
| CH₂CH₂CH₂CBrF₂ | C(S)N(CH₃)₂ | CH₃ | CF₂CF₃ |
| CH₂CH₂CH₂CBrF₂ | C(S)N(CH₃)₂ | CH₃ | CF₂CF₂CF₃ |
| CH₂CH₂CH₂CBrF₂ | C(S)N(CH₃)₂ | CH₂CH₃ | CF₃ |
| CH₂CH₂CH₂CBrF₂ | C(S)N(CH₃)₂ | CH₂CH₃ | CF₂CF₃ |
| CH₂CH₂CH₂CBrF₂ | C(S)N(CH₃)₂ | CH₂CH₃ | CF₂CF₂CF₃ |
| CH₂CH₂CH₂CBrF₂ | C(S)N(CH₃)₂ | F | CF₃ |
| CH₂CH₂CH₂CBrF₂ | C(S)N(CH₃)₂ | F | CF₂CF₃ |
| CH₂CH₂CH₂CBrF₂ | C(S)N(CH₃)₂ | F | CF₂CF₂CF₃ |
| CH₂CH₂CH₂CBrF₂ | C(S)N(CH₃)₂ | Cl | CF₃ |
| CH₂CH₂CH₂CBrF₂ | C(S)N(CH₃)₂ | Cl | CF₂CF₃ |
| CH₂CH₂CH₂CBrF₂ | C(S)N(CH₃)₂ | Cl | CF₂CF₂CF₃ |
| CH₂CH₂CH₂CF₂CBrF₂ | CN | H | CF₃ |
| CH₂CH₂CH₂CF₂CBrF₂ | CN | H | CF₂CF₃ |
| CH₂CH₂CH₂CF₂CBrF₂ | CN | H | CF₂CF₂CF₃ |
| CH₂CH₂CH₂CF₂CBrF₂ | CN | CH₃ | CF₃ |
| CH₂CH₂CH₂CF₂CBrF₂ | CN | CH₃ | CF₂CF₃ |
| CH₂CH₂CH₂CF₂CBrF₂ | CN | CH₃ | CF₂CF₂CF₃ |
| CH₂CH₂CH₂CF₂CBrF₂ | CN | CH₂CH₃ | CF₃ |
| CH₂CH₂CH₂CF₂CBrF₂ | CN | CH₂CH₃ | CF₂CF₃ |
| CH₂CH₂CH₂CF₂CBrF₂ | CN | CH₂CH₃ | CF₂CF₂CF₃ |
| CH₂CH₂CH₂CF₂CBrF₂ | CN | F | CF₃ |
| CH₂CH₂CH₂CF₂CBrF₂ | CN | F | CF₂CF₃ |
| CH₂CH₂CH₂CF₂CBrF₂ | CN | F | CF₂CF₂CF₃ |
| CH₂CH₂CH₂CF₂CBrF₂ | CN | Cl | CF₃ |
| CH₂CH₂CH₂CF₂CBrF₂ | CN | Cl | CF₂CF₃ |
| CH₂CH₂CH₂CF₂CBrF₂ | CN | Cl | CF₂CF₂CF₃ |

TABLE 40

| R¹ | R² | R³ | R⁴ |
|---|---|---|---|
| CH₂CH₂CH₂CF₂CBrF₂ | CO₂CH₃ | H | CF₃ |
| CH₂CH₂CH₂CF₂CBrF₂ | CO₂CH₃ | H | CF₂CF₃ |
| CH₂CH₂CH₂CF₂CBrF₂ | CO₂CH₃ | H | CF₂CF₂CF₃ |
| CH₂CH₂CH₂CF₂CBrF₂ | CO₂CH₃ | CH₃ | CF₃ |
| CH₂CH₂CH₂CF₂CBrF₂ | CO₂CH₃ | CH₃ | CF₂CF₃ |
| CH₂CH₂CH₂CF₂CBrF₂ | CO₂CH₃ | CH₃ | CF₂CF₂CF₃ |
| CH₂CH₂CH₂CF₂CBrF₂ | CO₂CH₃ | CH₂CH₃ | CF₃ |
| CH₂CH₂CH₂CF₂CBrF₂ | CO₂CH₃ | CH₂CH₃ | CF₂CF₃ |
| CH₂CH₂CH₂CF₂CBrF₂ | CO₂CH₃ | CH₂CH₃ | CF₂CF₂CF₃ |
| CH₂CH₂CH₂CF₂CBrF₂ | CO₂CH₃ | F | CF₃ |
| CH₂CH₂CH₂CF₂CBrF₂ | CO₂CH₃ | F | CF₂CF₃ |
| CH₂CH₂CH₂CF₂CBrF₂ | CO₂CH₃ | F | CF₂CF₂CF₃ |
| CH₂CH₂CH₂CF₂CBrF₂ | CO₂CH₃ | Cl | CF₃ |
| CH₂CH₂CH₂CF₂CBrF₂ | CO₂CH₃ | Cl | CF₂CF₃ |
| CH₂CH₂CH₂CF₂CBrF₂ | CO₂CH₃ | Cl | CF₂CF₂CF₃ |
| CH₂CH₂CH₂CF₂CBrF₂ | CO₂C(CH₃)₃ | H | CF₃ |
| CH₂CH₂CH₂CF₂CBrF₂ | CO₂C(CH₃)₃ | H | CF₂CF₃ |
| CH₂CH₂CH₂CF₂CBrF₂ | CO₂C(CH₃)₃ | H | CF₂CF₂CF₃ |
| CH₂CH₂CH₂CF₂CBrF₂ | CO₂C(CH₃)₃ | CH₃ | CF₃ |
| CH₂CH₂CH₂CF₂CBrF₂ | CO₂C(CH₃)₃ | CH₃ | CF₂CF₃ |
| CH₂CH₂CH₂CF₂CBrF₂ | CO₂C(CH₃)₃ | CH₃ | CF₂CF₂CF₃ |
| CH₂CH₂CH₂CF₂CBrF₂ | CO₂C(CH₃)₃ | CH₂CH₃ | CF₃ |
| CH₂CH₂CH₂CF₂CBrF₂ | CO₂C(CH₃)₃ | CH₂CH₃ | CF₂CF₃ |
| CH₂CH₂CH₂CF₂CBrF₂ | CO₂C(CH₃)₃ | CH₂CH₃ | CF₂CF₂CF₃ |
| CH₂CH₂CH₂CF₂CBrF₂ | CO₂C(CH₃)₃ | F | CF₃ |
| CH₂CH₂CH₂CF₂CBrF₂ | CO₂C(CH₃)₃ | F | CF₂CF₃ |
| CH₂CH₂CH₂CF₂CBrF₂ | CO₂C(CH₃)₃ | F | CF₂CF₂CF₃ |
| CH₂CH₂CH₂CF₂CBrF₂ | CO₂C(CH₃)₃ | Cl | CF₃ |
| CH₂CH₂CH₂CF₂CBrF₂ | CO₂C(CH₃)₃ | Cl | CF₂CF₃ |
| CH₂CH₂CH₂CF₂CBrF₂ | CO₂C(CH₃)₃ | Cl | CF₂CF₂CF₃ |

TABLE 41

| R¹ | R² | R³ | R⁴ |
|---|---|---|---|
| CH₂CH₂CH₂CF₂CBrF₂ | CONH₂ | H | CF₃ |
| CH₂CH₂CH₂CF₂CBrF₂ | CONH₂ | H | CF₂CF₃ |
| CH₂CH₂CH₂CF₂CBrF₂ | CONH₂ | H | CF₂CF₂CF₃ |
| CH₂CH₂CH₂CF₂CBrF₂ | CONH₂ | CH₃ | CF₃ |
| CH₂CH₂CH₂CF₂CBrF₂ | CONH₂ | CH₃ | CF₂CF₃ |
| CH₂CH₂CH₂CF₂CBrF₂ | CONH₂ | CH₃ | CF₂CF₂CF₃ |
| CH₂CH₂CH₂CF₂CBrF₂ | CONH₂ | CH₂CH₃ | CF₃ |
| CH₂CH₂CH₂CF₂CBrF₂ | CONH₂ | CH₂CH₃ | CF₂CF₃ |
| CH₂CH₂CH₂CF₂CBrF₂ | CONH₂ | CH₂CH₃ | CF₂CF₂CF₃ |
| CH₂CH₂CH₂CF₂CBrF₂ | CONH₂ | F | CF₃ |
| CH₂CH₂CH₂CF₂CBrF₂ | CONH₂ | F | CF₂CF₃ |
| CH₂CH₂CH₂CF₂CBrF₂ | CONH₂ | F | CF₂CF₂CF₃ |
| CH₂CH₂CH₂CF₂CBrF₂ | CONH₂ | Cl | CF₃ |
| CH₂CH₂CH₂CF₂CBrF₂ | CONH₂ | Cl | CF₂CF₃ |
| CH₂CH₂CH₂CF₂CBrF₂ | CONH₂ | Cl | CF₂CF₂CF₃ |
| CH₂CH₂CH₂CF₂CBrF₂ | CONH(CH₃) | H | CF₃ |
| CH₂CH₂CH₂CF₂CBrF₂ | CONH(CH₃) | H | CF₂CF₃ |
| CH₂CH₂CH₂CF₂CBrF₂ | CONH(CH₃) | H | CF₂CF₂CF₃ |
| CH₂CH₂CH₂CF₂CBrF₂ | CONH(CH₃) | CH₃ | CF₃ |
| CH₂CH₂CH₂CF₂CBrF₂ | CONH(CH₃) | CH₃ | CF₂CF₃ |
| CH₂CH₂CH₂CF₂CBrF₂ | CONH(CH₃) | CH₃ | CF₂CF₂CF₃ |
| CH₂CH₂CH₂CF₂CBrF₂ | CONH(CH₃) | CH₂CH₃ | CF₃ |
| CH₂CH₂CH₂CF₂CBrF₂ | CONH(CH₃) | CH₂CH₃ | CF₂CF₃ |
| CH₂CH₂CH₂CF₂CBrF₂ | CONH(CH₃) | CH₂CH₃ | CF₂CF₂CF₃ |
| CH₂CH₂CH₂CF₂CBrF₂ | CONH(CH₃) | F | CF₃ |
| CH₂CH₂CH₂CF₂CBrF₂ | CONH(CH₃) | F | CF₂CF₃ |
| CH₂CH₂CH₂CF₂CBrF₂ | CONH(CH₃) | F | CF₂CF₂CF₃ |
| CH₂CH₂CH₂CF₂CBrF₂ | CONH(CH₃) | Cl | CF₃ |
| CH₂CH₂CH₂CF₂CBrF₂ | CONH(CH₃) | Cl | CF₂CF₃ |
| CH₂CH₂CH₂CF₂CBrF₂ | CONH(CH₃) | Cl | CF₂CF₂CF₃ |

TABLE 42

| R¹ | R² | R³ | R⁴ |
|---|---|---|---|
| CH₂CH₂CH₂CF₂CBrF₂ | CONH(CH₂CH₃) | H | CF₃ |
| CH₂CH₂CH₂CF₂CBrF₂ | CONH(CH₂CH₃) | H | CF₂CF₃ |
| CH₂CH₂CH₂CF₂CBrF₂ | CONH(CH₂CH₃) | H | CF₂CF₂CF₃ |
| CH₂CH₂CH₂CF₂CBrF₂ | CONH(CH₂CH₃) | CH₃ | CF₃ |
| CH₂CH₂CH₂CF₂CBrF₂ | CONH(CH₂CH₃) | CH₃ | CF₂CF₃ |
| CH₂CH₂CH₂CF₂CBrF₂ | CONH(CH₂CH₃) | CH₃ | CF₂CF₂CF₃ |

TABLE 42-continued

| R¹ | R² | R³ | R⁴ |
|---|---|---|---|
| CH₂CH₂CH₂CF₂CBrF₂ | CONH(CH₂CH₃) | CH₂CH₃ | CF₃ |
| CH₂CH₂CH₂CF₂CBrF₂ | CONH(CH₂CH₃) | CH₂CH₃ | CF₂CF₃ |
| CH₂CH₂CH₂CF₂CBrF₂ | CONH(CH₂CH₃) | CH₂CH₃ | CF₂CF₂CF₃ |
| CH₂CH₂CH₂CF₂CBrF₂ | CONH(CH₂CH₃) | F | CF₃ |
| CH₂CH₂CH₂CF₂CBrF₂ | CONH(CH₂CH₃) | F | CF₂CF₃ |
| CH₂CH₂CH₂CF₂CBrF₂ | CONH(CH₂CH₃) | F | CF₂CF₂CF₃ |
| CH₂CH₂CH₂CF₂CBrF₂ | CONH(CH₂CH₃) | Cl | CF₃ |
| CH₂CH₂CH₂CF₂CBrF₂ | CONH(CH₂CH₃) | Cl | CF₂CF₃ |
| CH₂CH₂CH₂CF₂CBrF₂ | CONH(CH₂CH₃) | Cl | CF₂CF₂CF₃ |
| CH₂CH₂CH₂CF₂CBrF₂ | CON(CH₃)₂ | H | CF₃ |
| CH₂CH₂CH₂CF₂CBrF₂ | CON(CH₃)₂ | H | CF₂CF₃ |
| CH₂CH₂CH₂CF₂CBrF₂ | CON(CH₃)₂ | H | CF₂CF₂CF₃ |
| CH₂CH₂CH₂CF₂CBrF₂ | CON(CH₃)₂ | CH₃ | CF₃ |
| CH₂CH₂CH₂CF₂CBrF₂ | CON(CH₃)₂ | CH₃ | CF₂CF₃ |
| CH₂CH₂CH₂CF₂CBrF₂ | CON(CH₃)₂ | CH₃ | CF₂CF₂CF₃ |
| CH₂CH₂CH₂CF₂CBrF₂ | CON(CH₃)₂ | CH₂CH₃ | CF₃ |
| CH₂CH₂CH₂CF₂CBrF₂ | CON(CH₃)₂ | CH₂CH₃ | CF₂CF₃ |
| CH₂CH₂CH₂CF₂CBrF₂ | CON(CH₃)₂ | CH₂CH₃ | CF₂CF₂CF₃ |
| CH₂CH₂CH₂CF₂CBrF₂ | CON(CH₃)₂ | F | CF₃ |
| CH₂CH₂CH₂CF₂CBrF₂ | CON(CH₃)₂ | F | CF₂CF₃ |
| CH₂CH₂CH₂CF₂CBrF₂ | CON(CH₃)₂ | F | CF₂CF₂CF₃ |
| CH₂CH₂CH₂CF₂CBrF₂ | CON(CH₃)₂ | Cl | CF₃ |
| CH₂CH₂CH₂CF₂CBrF₂ | CON(CH₃)₂ | Cl | CF₂CF₃ |
| CH₂CH₂CH₂CF₂CBrF₂ | CON(CH₃)₂ | Cl | CF₂CF₂CF₃ |

TABLE 43

| R¹ | R² | R³ | R⁴ |
|---|---|---|---|
| CH₂CH₂CH₂CF₂CBrF₂ | C(S)OCH₃ | H | CF₃ |
| CH₂CH₂CH₂CF₂CBrF₂ | C(S)OCH₃ | H | CF₂CF₃ |
| CH₂CH₂CH₂CF₂CBrF₂ | C(S)OCH₃ | H | CF₂CF₂CF₃ |
| CH₂CH₂CH₂CF₂CBrF₂ | C(S)OCH₃ | CH₃ | CF₃ |
| CH₂CH₂CH₂CF₂CBrF₂ | C(S)OCH₃ | CH₃ | CF₂CF₃ |
| CH₂CH₂CH₂CF₂CBrF₂ | C(S)OCH₃ | CH₃ | CF₂CF₂CF₃ |
| CH₂CH₂CH₂CF₂CBrF₂ | C(S)OCH₃ | CH₂CH₃ | CF₃ |
| CH₂CH₂CH₂CF₂CBrF₂ | C(S)OCH₃ | CH₂CH₃ | CF₂CF₃ |
| CH₂CH₂CH₂CF₂CBrF₂ | C(S)OCH₃ | CH₂CH₃ | CF₂CF₂CF₃ |
| CH₂CH₂CH₂CF₂CBrF₂ | C(S)OCH₃ | F | CF₃ |
| CH₂CH₂CH₂CF₂CBrF₂ | C(S)OCH₃ | F | CF₂CF₃ |
| CH₂CH₂CH₂CF₂CBrF₂ | C(S)OCH₃ | F | CF₂CF₂CF₃ |
| CH₂CH₂CH₂CF₂CBrF₂ | C(S)OCH₃ | Cl | CF₃ |
| CH₂CH₂CH₂CF₂CBrF₂ | C(S)OCH₃ | Cl | CF₂CF₃ |
| CH₂CH₂CH₂CF₂CBrF₂ | C(S)OCH₃ | Cl | CF₂CF₂CF₃ |
| CH₂CH₂CH₂CF₂CBrF₂ | C(S)NH₂ | H | CF₃ |
| CH₂CH₂CH₂CF₂CBrF₂ | C(S)NH₂ | H | CF₂CF₃ |
| CH₂CH₂CH₂CF₂CBrF₂ | C(S)NH₂ | H | CF₂CF₂CF₃ |
| CH₂CH₂CH₂CF₂CBrF₂ | C(S)NH₂ | CH₃ | CF₃ |
| CH₂CH₂CH₂CF₂CBrF₂ | C(S)NH₂ | CH₃ | CF₂CF₃ |
| CH₂CH₂CH₂CF₂CBrF₂ | C(S)NH₂ | CH₃ | CF₂CF₂CF₃ |
| CH₂CH₂CH₂CF₂CBrF₂ | C(S)NH₂ | CH₂CH₃ | CF₃ |
| CH₂CH₂CH₂CF₂CBrF₂ | C(S)NH₂ | CH₂CH₃ | CF₂CF₃ |
| CH₂CH₂CH₂CF₂CBrF₂ | C(S)NH₂ | CH₂CH₃ | CF₂CF₂CF₃ |
| CH₂CH₂CH₂CF₂CBrF₂ | C(S)NH₂ | F | CF₃ |
| CH₂CH₂CH₂CF₂CBrF₂ | C(S)NH₂ | F | CF₂CF₃ |
| CH₂CH₂CH₂CF₂CBrF₂ | C(S)NH₂ | F | CF₂CF₂CF₃ |
| CH₂CH₂CH₂CF₂CBrF₂ | C(S)NH₂ | Cl | CF₃ |
| CH₂CH₂CH₂CF₂CBrF₂ | C(S)NH₂ | Cl | CF₂CF₃ |
| CH₂CH₂CH₂CF₂CBrF₂ | C(S)NH₂ | Cl | CF₂CF₂CF₃ |

TABLE 44

| R¹ | R² | R³ | R⁴ |
|---|---|---|---|
| CH₂CH₂CH₂CF₂CBrF₂ | C(S)NH(CH₃) | H | CF₃ |
| CH₂CH₂CH₂CF₂CBrF₂ | C(S)NH(CH₃) | H | CF₂CF₃ |
| CH₂CH₂CH₂CF₂CBrF₂ | C(S)NH(CH₃) | H | CF₂CF₂CF₃ |
| CH₂CH₂CH₂CF₂CBrF₂ | C(S)NH(CH₃) | CH₃ | CF₃ |
| CH₂CH₂CH₂CF₂CBrF₂ | C(S)NH(CH₃) | CH₃ | CF₂CF₃ |
| CH₂CH₂CH₂CF₂CBrF₂ | C(S)NH(CH₃) | CH₃ | CF₂CF₂CF₃ |
| CH₂CH₂CH₂CF₂CBrF₂ | C(S)NH(CH₃) | CH₂CH₃ | CF₃ |
| CH₂CH₂CH₂CF₂CBrF₂ | C(S)NH(CH₃) | CH₂CH₃ | CF₂CF₃ |
| CH₂CH₂CH₂CF₂CBrF₂ | C(S)NH(CH₃) | CH₂CH₃ | CF₂CF₂CF₃ |

TABLE 44-continued

| R¹ | R² | R³ | R⁴ |
|---|---|---|---|
| CH₂CH₂CH₂CF₂CBrF₂ | C(S)NH(CH₃) | F | CF₃ |
| CH₂CH₂CH₂CF₂CBrF₂ | C(S)NH(CH₃) | F | CF₂CF₃ |
| CH₂CH₂CH₂CF₂CBrF₂ | C(S)NH(CH₃) | F | CF₂CF₂CF₃ |
| CH₂CH₂CH₂CF₂CBrF₂ | C(S)NH(CH₃) | Cl | CF₃ |
| CH₂CH₂CH₂CF₂CBrF₂ | C(S)NH(CH₃) | Cl | CF₂CF₃ |
| CH₂CH₂CH₂CF₂CBrF₂ | C(S)NH(CH₃) | Cl | CF₂CF₂CF₃ |
| CH₂CH₂CH₂CF₂CBrF₂ | C(S)N(CH₃)₂ | H | CF₃ |
| CH₂CH₂CH₂CF₂CBrF₂ | C(S)N(CH₃)₂ | H | CF₂CF₃ |
| CH₂CH₂CH₂CF₂CBrF₂ | C(S)N(CH₃)₂ | H | CF₂CF₂CF₃ |
| CH₂CH₂CH₂CF₂CBrF₂ | C(S)N(CH₃)₂ | CH₃ | CF₃ |
| CH₂CH₂CH₂CF₂CBrF₂ | C(S)N(CH₃)₂ | CH₃ | CF₂CF₃ |
| CH₂CH₂CH₂CF₂CBrF₂ | C(S)N(CH₃)₂ | CH₃ | CF₂CF₂CF₃ |
| CH₂CH₂CH₂CF₂CBrF₂ | C(S)N(CH₃)₂ | CH₂CH₃ | CF₃ |
| CH₂CH₂CH₂CF₂CBrF₂ | C(S)N(CH₃)₂ | CH₂CH₃ | CF₂CF₃ |
| CH₂CH₂CH₂CF₂CBrF₂ | C(S)N(CH₃)₂ | CH₂CH₃ | CF₂CF₂CF₃ |
| CH₂CH₂CH₂CF₂CBrF₂ | C(S)N(CH₃)₂ | F | CF₃ |
| CH₂CH₂CH₂CF₂CBrF₂ | C(S)N(CH₃)₂ | F | CF₂CF₃ |
| CH₂CH₂CH₂CF₂CBrF₂ | C(S)N(CH₃)₂ | F | CF₂CF₂CF₃ |
| CH₂CH₂CH₂CF₂CBrF₂ | C(S)N(CH₃)₂ | Cl | CF₃ |
| CH₂CH₂CH₂CF₂CBrF₂ | C(S)N(CH₃)₂ | Cl | CF₂CF₃ |
| CH₂CH₂CH₂CF₂CBrF₂ | C(S)N(CH₃)₂ | Cl | CF₂CF₂CF₃ |

TABLE 45

| R¹ | R² | R³ | R⁴ |
|---|---|---|---|
| CH₂CH₂CH₂CH₂CClFCBrF₂ | CN | H | CF₃ |
| CH₂CH₂CH₂CH₂CClFCBrF₂ | CN | H | CF₂CF₃ |
| CH₂CH₂CH₂CH₂CClFCBrF₂ | CN | H | CF₂CF₂CF₃ |
| CH₂CH₂CH₂CH₂CClFCBrF₂ | CN | CH₃ | CF₃ |
| CH₂CH₂CH₂CH₂CClFCBrF₂ | CN | CH₃ | CF₂CF₃ |
| CH₂CH₂CH₂CH₂CClFCBrF₂ | CN | CH₃ | CF₂CF₂CF₃ |
| CH₂CH₂CH₂CH₂CClFCBrF₂ | CN | CH₂CH₃ | CF₃ |
| CH₂CH₂CH₂CH₂CClFCBrF₂ | CN | CH₂CH₃ | CF₂CF₃ |
| CH₂CH₂CH₂CH₂CClFCBrF₂ | CN | CH₂CH₃ | CF₂CF₂CF₃ |
| CH₂CH₂CH₂CH₂CClFCBrF₂ | CN | F | CF₃ |
| CH₂CH₂CH₂CH₂CClFCBrF₂ | CN | F | CF₂CF₃ |
| CH₂CH₂CH₂CH₂CClFCBrF₂ | CN | F | CF₂CF₂CF₃ |
| CH₂CH₂CH₂CH₂CClFCBrF₂ | CN | Cl | CF₃ |
| CH₂CH₂CH₂CH₂CClFCBrF₂ | CN | Cl | CF₂CF₃ |
| CH₂CH₂CH₂CH₂CClFCBrF₂ | CN | Cl | CF₂CF₂CF₃ |
| CH₂CH₂CH₂CH₂CClFCBrF₂ | CO₂CH₃ | H | CF₃ |
| CH₂CH₂CH₂CH₂CClFCBrF₂ | CO₂CH₃ | H | CF₂CF₃ |
| CH₂CH₂CH₂CH₂CClFCBrF₂ | CO₂CH₃ | H | CF₂CF₂CF₃ |
| CH₂CH₂CH₂CH₂CClFCBrF₂ | CO₂CH₃ | CH₃ | CF₃ |
| CH₂CH₂CH₂CH₂CClFCBrF₂ | CO₂CH₃ | CH₃ | CF₂CF₃ |
| CH₂CH₂CH₂CH₂CClFCBrF₂ | CO₂CH₃ | CH₃ | CF₂CF₂CF₃ |
| CH₂CH₂CH₂CH₂CClFCBrF₂ | CO₂CH₃ | CH₂CH₃ | CF₃ |
| CH₂CH₂CH₂CH₂CClFCBrF₂ | CO₂CH₃ | CH₂CH₃ | CF₂CF₃ |
| CH₂CH₂CH₂CH₂CClFCBrF₂ | CO₂CH₃ | CH₂CH₃ | CF₂CF₂CF₃ |
| CH₂CH₂CH₂CH₂CClFCBrF₂ | CO₂CH₃ | F | CF₃ |
| CH₂CH₂CH₂CH₂CClFCBrF₂ | CO₂CH₃ | F | CF₂CF₃ |
| CH₂CH₂CH₂CH₂CClFCBrF₂ | CO₂CH₃ | F | CF₂CF₂CF₃ |
| CH₂CH₂CH₂CH₂CClFCBrF₂ | CO₂CH₃ | Cl | CF₃ |
| CH₂CH₂CH₂CH₂CClFCBrF₂ | CO₂CH₃ | Cl | CF₂CF₃ |
| CH₂CH₂CH₂CH₂CClFCBrF₂ | CO₂CH₃ | Cl | CF₂CF₂CF₃ |

TABLE 46

| R¹ | R² | R³ | R⁴ |
|---|---|---|---|
| CH₂CH₂CH₂CH₂CClFCBrF₂ | CO₂C(CH₃)₃ | H | CF₃ |
| CH₂CH₂CH₂CH₂CClFCBrF₂ | CO₂C(CH₃)₃ | H | CF₂CF₃ |
| CH₂CH₂CH₂CH₂CClFCBrF₂ | CO₂C(CH₃)₃ | H | CF₂CF₂CF₃ |
| CH₂CH₂CH₂CH₂CClFCBrF₂ | CO₂C(CH₃)₃ | CH₃ | CF₃ |
| CH₂CH₂CH₂CH₂CClFCBrF₂ | CO₂C(CH₃)₃ | CH₃ | CF₂CF₃ |
| CH₂CH₂CH₂CH₂CClFCBrF₂ | CO₂C(CH₃)₃ | CH₃ | CF₂CF₂CF₃ |
| CH₂CH₂CH₂CH₂CClFCBrF₂ | CO₂C(CH₃)₃ | CH₂CH₃ | CF₃ |
| CH₂CH₂CH₂CH₂CClFCBrF₂ | CO₂C(CH₃)₃ | CH₂CH₃ | CF₂CF₃ |
| CH₂CH₂CH₂CH₂CClFCBrF₂ | CO₂C(CH₃)₃ | CH₂CH₃ | CF₂CF₂CF₃ |
| CH₂CH₂CH₂CH₂CClFCBrF₂ | CO₂C(CH₃)₃ | F | CF₃ |
| CH₂CH₂CH₂CH₂CClFCBrF₂ | CO₂C(CH₃)₃ | F | CF₂CF₃ |
| CH₂CH₂CH₂CH₂CClFCBrF₂ | CO₂C(CH₃)₃ | F | CF₂CF₂CF₃ |

TABLE 46-continued

| R$^1$ | R$^2$ | R$^3$ | R$^4$ |
|---|---|---|---|
| CH$_2$CH$_2$CH$_2$CH$_2$CClFCBrF$_2$ | CO$_2$C(CH$_3$)$_3$ | Cl | CF$_3$ |
| CH$_2$CH$_2$CH$_2$CH$_2$CClFCBrF$_2$ | CO$_2$C(CH$_3$)$_3$ | Cl | CF$_2$CF$_3$ |
| CH$_2$CH$_2$CH$_2$CH$_2$CClFCBrF$_2$ | CO$_2$C(CH$_3$)$_3$ | Cl | CF$_2$CF$_2$CF$_3$ |
| CH$_2$CH$_2$CH$_2$CH$_2$CClFCBrF$_2$ | CONH$_2$ | H | CF$_3$ |
| CH$_2$CH$_2$CH$_2$CH$_2$CClFCBrF$_2$ | CONH$_2$ | H | CF$_2$CF$_3$ |
| CH$_2$CH$_2$CH$_2$CH$_2$CClFCBrF$_2$ | CONH$_2$ | H | CF$_2$CF$_2$CF$_3$ |
| CH$_2$CH$_2$CH$_2$CH$_2$CClFCBrF$_2$ | CONH$_2$ | CH$_3$ | CF$_3$ |
| CH$_2$CH$_2$CH$_2$CH$_2$CClFCBrF$_2$ | CONH$_2$ | CH$_3$ | CF$_2$CF$_3$ |
| CH$_2$CH$_2$CH$_2$CH$_2$CClFCBrF$_2$ | CONH$_2$ | CH$_3$ | CF$_2$CF$_2$CF$_3$ |
| CH$_2$CH$_2$CH$_2$CH$_2$CClFCBrF$_2$ | CONH$_2$ | CH$_2$CH$_3$ | CF$_3$ |
| CH$_2$CH$_2$CH$_2$CH$_2$CClFCBrF$_2$ | CONH$_2$ | CH$_2$CH$_3$ | CF$_2$CF$_3$ |
| CH$_2$CH$_2$CH$_2$CH$_2$CClFCBrF$_2$ | CONH$_2$ | CH$_2$CH$_3$ | CF$_2$CF$_2$CF$_3$ |
| CH$_2$CH$_2$CH$_2$CH$_2$CClFCBrF$_2$ | CONH$_2$ | F | CF$_3$ |
| CH$_2$CH$_2$CH$_2$CH$_2$CClFCBrF$_2$ | CONH$_2$ | F | CF$_2$CF$_3$ |
| CH$_2$CH$_2$CH$_2$CH$_2$CClFCBrF$_2$ | CONH$_2$ | F | CF$_2$CF$_2$CF$_3$ |
| CH$_2$CH$_2$CH$_2$CH$_2$CClFCBrF$_2$ | CONH$_2$ | Cl | CF$_3$ |
| CH$_2$CH$_2$CH$_2$CH$_2$CClFCBrF$_2$ | CONH$_2$ | Cl | CF$_2$CF$_3$ |
| CH$_2$CH$_2$CH$_2$CH$_2$CClFCBrF$_2$ | CONH$_2$ | Cl | CF$_2$CF$_2$CF$_3$ |

TABLE 47

| R$^1$ | R$^2$ | R$^3$ | R$^4$ |
|---|---|---|---|
| CH$_2$CH$_2$CH$_2$CH$_2$CClFCBrF$_2$ | CONH(CH$_3$) | H | CF$_3$ |
| CH$_2$CH$_2$CH$_2$CH$_2$CClFCBrF$_2$ | CONH(CH$_3$) | H | CF$_2$CF$_3$ |
| CH$_2$CH$_2$CH$_2$CH$_2$CClFCBrF$_2$ | CONH(CH$_3$) | H | CF$_2$CF$_2$CF$_3$ |
| CH$_2$CH$_2$CH$_2$CH$_2$CClFCBrF$_2$ | CONH(CH$_3$) | CH$_3$ | CF$_3$ |
| CH$_2$CH$_2$CH$_2$CH$_2$CClFCBrF$_2$ | CONH(CH$_3$) | CH$_3$ | CF$_2$CF$_3$ |
| CH$_2$CH$_2$CH$_2$CH$_2$CClFCBrF$_2$ | CONH(CH$_3$) | CH$_3$ | CF$_2$CF$_2$CF$_3$ |
| CH$_2$CH$_2$CH$_2$CH$_2$CClFCBrF$_2$ | CONH(CH$_3$) | CH$_2$CH$_3$ | CF$_3$ |
| CH$_2$CH$_2$CH$_2$CH$_2$CClFCBrF$_2$ | CONH(CH$_3$) | CH$_2$CH$_3$ | CF$_2$CF$_3$ |
| CH$_2$CH$_2$CH$_2$CH$_2$CClFCBrF$_2$ | CONH(CH$_3$) | CH$_2$CH$_3$ | CF$_2$CF$_2$CF$_3$ |
| CH$_2$CH$_2$CH$_2$CH$_2$CClFCBrF$_2$ | CONH(CH$_3$) | F | CF$_3$ |
| CH$_2$CH$_2$CH$_2$CH$_2$CClFCBrF$_2$ | CONH(CH$_3$) | F | CF$_2$CF$_3$ |
| CH$_2$CH$_2$CH$_2$CH$_2$CClFCBrF$_2$ | CONH(CH$_3$) | F | CF$_2$CF$_2$CF$_3$ |
| CH$_2$CH$_2$CH$_2$CH$_2$CClFCBrF$_2$ | CONH(CH$_3$) | Cl | CF$_3$ |
| CH$_2$CH$_2$CH$_2$CH$_2$CClFCBrF$_2$ | CONH(CH$_3$) | Cl | CF$_2$CF$_3$ |
| CH$_2$CH$_2$CH$_2$CH$_2$CClFCBrF$_2$ | CONH(CH$_3$) | Cl | CF$_2$CF$_2$CF$_3$ |
| CH$_2$CH$_2$CH$_2$CH$_2$CClFCBrF$_2$ | CONH(CH$_2$CH$_3$) | H | CF$_3$ |
| CH$_2$CH$_2$CH$_2$CH$_2$CClFCBrF$_2$ | CONH(CH$_2$CH$_3$) | H | CF$_2$CF$_3$ |
| CH$_2$CH$_2$CH$_2$CH$_2$CClFCBrF$_2$ | CONH(CH$_2$CH$_3$) | H | CF$_2$CF$_2$CF$_3$ |
| CH$_2$CH$_2$CH$_2$CH$_2$CClFCBrF$_2$ | CONH(CH$_2$CH$_3$) | CH$_3$ | CF$_3$ |
| CH$_2$CH$_2$CH$_2$CH$_2$CClFCBrF$_2$ | CONH(CH$_2$CH$_3$) | CH$_3$ | CF$_2$CF$_3$ |
| CH$_2$CH$_2$CH$_2$CH$_2$CClFCBrF$_2$ | CONH(CH$_2$CH$_3$) | CH$_3$ | CF$_2$CF$_2$CF$_3$ |
| CH$_2$CH$_2$CH$_2$CH$_2$CClFCBrF$_2$ | CONH(CH$_2$CH$_3$) | CH$_2$CH$_3$ | CF$_3$ |
| CH$_2$CH$_2$CH$_2$CH$_2$CClFCBrF$_2$ | CONH(CH$_2$CH$_3$) | CH$_2$CH$_3$ | CF$_2$CF$_3$ |
| CH$_2$CH$_2$CH$_2$CH$_2$CClFCBrF$_2$ | CONH(CH$_2$CH$_3$) | CH$_2$CH$_3$ | CF$_2$CF$_2$CF$_3$ |
| CH$_2$CH$_2$CH$_2$CH$_2$CClFCBrF$_2$ | CONH(CH$_2$CH$_3$) | F | CF$_3$ |
| CH$_2$CH$_2$CH$_2$CH$_2$CClFCBrF$_2$ | CONH(CH$_2$CH$_3$) | F | CF$_2$CF$_3$ |
| CH$_2$CH$_2$CH$_2$CH$_2$CClFCBrF$_2$ | CONH(CH$_2$CH$_3$) | F | CF$_2$CF$_2$CF$_3$ |
| CH$_2$CH$_2$CH$_2$CH$_2$CClFCBrF$_2$ | CONH(CH$_2$CH$_3$) | Cl | CF$_3$ |
| CH$_2$CH$_2$CH$_2$CH$_2$CClFCBrF$_2$ | CONH(CH$_2$CH$_3$) | Cl | CF$_2$CF$_3$ |
| CH$_2$CH$_2$CH$_2$CH$_2$CClFCBrF$_2$ | CONH(CH$_2$CH$_3$) | Cl | CF$_2$CF$_2$CF$_3$ |

TABLE 48

| R$^1$ | R$^2$ | R$^3$ | R$^4$ |
|---|---|---|---|
| CH$_2$CH$_2$CH$_2$CH$_2$CClFCBrF$_2$ | CON(CH$_3$)$_2$ | H | CF$_3$ |
| CH$_2$CH$_2$CH$_2$CH$_2$CClFCBrF$_2$ | CON(CH$_3$)$_2$ | H | CF$_2$CF$_3$ |
| CH$_2$CH$_2$CH$_2$CH$_2$CClFCBrF$_2$ | CON(CH$_3$)$_2$ | H | CF$_2$CF$_2$CF$_3$ |
| CH$_2$CH$_2$CH$_2$CH$_2$CClFCBrF$_2$ | CON(CH$_3$)$_2$ | CH$_3$ | CF$_3$ |
| CH$_2$CH$_2$CH$_2$CH$_2$CClFCBrF$_2$ | CON(CH$_3$)$_2$ | CH$_3$ | CF$_2$CF$_3$ |
| CH$_2$CH$_2$CH$_2$CH$_2$CClFCBrF$_2$ | CON(CH$_3$)$_2$ | CH$_3$ | CF$_2$CF$_2$CF$_3$ |
| CH$_2$CH$_2$CH$_2$CH$_2$CClFCBrF$_2$ | CON(CH$_3$)$_2$ | CH$_2$CH$_3$ | CF$_3$ |
| CH$_2$CH$_2$CH$_2$CH$_2$CClFCBrF$_2$ | CON(CH$_3$)$_2$ | CH$_2$CH$_3$ | CF$_2$CF$_3$ |
| CH$_2$CH$_2$CH$_2$CH$_2$CClFCBrF$_2$ | CON(CH$_3$)$_2$ | CH$_2$CH$_3$ | CF$_2$CF$_2$CF$_3$ |
| CH$_2$CH$_2$CH$_2$CH$_2$CClFCBrF$_2$ | CON(CH$_3$)$_2$ | F | CF$_3$ |
| CH$_2$CH$_2$CH$_2$CH$_2$CClFCBrF$_2$ | CON(CH$_3$)$_2$ | F | CF$_2$CF$_3$ |
| CH$_2$CH$_2$CH$_2$CH$_2$CClFCBrF$_2$ | CON(CH$_3$)$_2$ | F | CF$_2$CF$_2$CF$_3$ |
| CH$_2$CH$_2$CH$_2$CH$_2$CClFCBrF$_2$ | CON(CH$_3$)$_2$ | Cl | CF$_3$ |
| CH$_2$CH$_2$CH$_2$CH$_2$CClFCBrF$_2$ | CON(CH$_3$)$_2$ | Cl | CF$_2$CF$_3$ |
| CH$_2$CH$_2$CH$_2$CH$_2$CClFCBrF$_2$ | CON(CH$_3$)$_2$ | Cl | CF$_2$CF$_2$CF$_3$ |

TABLE 48-continued

| R$^1$ | R$^2$ | R$^3$ | R$^4$ |
|---|---|---|---|
| CH$_2$CH$_2$CH$_2$CH$_2$CClFCBrF$_2$ | C(S)OCH$_3$ | H | CF$_3$ |
| CH$_2$CH$_2$CH$_2$CH$_2$CClFCBrF$_2$ | C(S)OCH$_3$ | H | CF$_2$CF$_3$ |
| CH$_2$CH$_2$CH$_2$CH$_2$CClFCBrF$_2$ | C(S)OCH$_3$ | H | CF$_2$CF$_2$CF$_3$ |
| CH$_2$CH$_2$CH$_2$CH$_2$CClFCBrF$_2$ | C(S)OCH$_3$ | CH$_3$ | CF$_3$ |
| CH$_2$CH$_2$CH$_2$CH$_2$CClFCBrF$_2$ | C(S)OCH$_3$ | CH$_3$ | CF$_2$CF$_3$ |
| CH$_2$CH$_2$CH$_2$CH$_2$CClFCBrF$_2$ | C(S)OCH$_3$ | CH$_3$ | CF$_2$CF$_2$CF$_3$ |
| CH$_2$CH$_2$CH$_2$CH$_2$CClFCBrF$_2$ | C(S)OCH$_3$ | CH$_2$CH$_3$ | CF$_3$ |
| CH$_2$CH$_2$CH$_2$CH$_2$CClFCBrF$_2$ | C(S)OCH$_3$ | CH$_2$CH$_3$ | CF$_2$CF$_3$ |
| CH$_2$CH$_2$CH$_2$CH$_2$CClFCBrF$_2$ | C(S)OCH$_3$ | CH$_2$CH$_3$ | CF$_2$CF$_2$CF$_3$ |
| CH$_2$CH$_2$CH$_2$CH$_2$CClFCBrF$_2$ | C(S)OCH$_3$ | F | CF$_3$ |
| CH$_2$CH$_2$CH$_2$CH$_2$CClFCBrF$_2$ | C(S)OCH$_3$ | F | CF$_2$CF$_3$ |
| CH$_2$CH$_2$CH$_2$CH$_2$CClFCBrF$_2$ | C(S)OCH$_3$ | F | CF$_2$CF$_2$CF$_3$ |
| CH$_2$CH$_2$CH$_2$CH$_2$CClFCBrF$_2$ | C(S)OCH$_3$ | Cl | CF$_3$ |
| CH$_2$CH$_2$CH$_2$CH$_2$CClFCBrF$_2$ | C(S)OCH$_3$ | Cl | CF$_2$CF$_3$ |
| CH$_2$CH$_2$CH$_2$CH$_2$CClFCBrF$_2$ | C(S)OCH$_3$ | Cl | CF$_2$CF$_2$CF$_3$ |

TABLE 49

| R$^1$ | R$^2$ | R$^3$ | R$^4$ |
|---|---|---|---|
| CH$_2$CH$_2$CH$_2$CH$_2$CClFCBrF$_2$ | C(S)NH$_2$ | H | CF$_3$ |
| CH$_2$CH$_2$CH$_2$CH$_2$CClFCBrF$_2$ | C(S)NH$_2$ | H | CF$_2$CF$_3$ |
| CH$_2$CH$_2$CH$_2$CH$_2$CClFCBrF$_2$ | C(S)NH$_2$ | H | CF$_2$CF$_2$CF$_3$ |
| CH$_2$CH$_2$CH$_2$CH$_2$CClFCBrF$_2$ | C(S)NH$_2$ | CH$_3$ | CF$_3$ |
| CH$_2$CH$_2$CH$_2$CH$_2$CClFCBrF$_2$ | C(S)NH$_2$ | CH$_3$ | CF$_2$CF$_3$ |
| CH$_2$CH$_2$CH$_2$CH$_2$CClFCBrF$_2$ | C(S)NH$_2$ | CH$_3$ | CF$_2$CF$_2$CF$_3$ |
| CH$_2$CH$_2$CH$_2$CH$_2$CClFCBrF$_2$ | C(S)NH$_2$ | CH$_2$CH$_3$ | CF$_3$ |
| CH$_2$CH$_2$CH$_2$CH$_2$CClFCBrF$_2$ | C(S)NH$_2$ | CH$_2$CH$_3$ | CF$_2$CF$_3$ |
| CH$_2$CH$_2$CH$_2$CH$_2$CClFCBrF$_2$ | C(S)NH$_2$ | CH$_2$CH$_3$ | CF$_2$CF$_2$CF$_3$ |
| CH$_2$CH$_2$CH$_2$CH$_2$CClFCBrF$_2$ | C(S)NH$_2$ | F | CF$_3$ |
| CH$_2$CH$_2$CH$_2$CH$_2$CClFCBrF$_2$ | C(S)NH$_2$ | F | CF$_2$CF$_3$ |
| CH$_2$CH$_2$CH$_2$CH$_2$CClFCBrF$_2$ | C(S)NH$_2$ | F | CF$_2$CF$_2$CF$_3$ |
| CH$_2$CH$_2$CH$_2$CH$_2$CClFCBrF$_2$ | C(S)NH$_2$ | Cl | CF$_3$ |
| CH$_2$CH$_2$CH$_2$CH$_2$CClFCBrF$_2$ | C(S)NH$_2$ | Cl | CF$_2$CF$_3$ |
| CH$_2$CH$_2$CH$_2$CH$_2$CClFCBrF$_2$ | C(S)NH$_2$ | Cl | CF$_2$CF$_2$CF$_3$ |

TABLE 49-continued

| R¹ | R² | R³ | R⁴ |
|---|---|---|---|
| CH₂CH₂CH₂CH₂CClFCBrF₂ | C(S)NH(CH₃) | H | CF₃ |
| CH₂CH₂CH₂CH₂CClFCBrF₂ | C(S)NH(CH₃) | H | CF₂CF₃ |
| CH₂CH₂CH₂CH₂CClFCBrF₂ | C(S)NH(CH₃) | H | CF₂CF₂CF₃ |
| CH₂CH₂CH₂CH₂CClFCBrF₂ | C(S)NH(CH₃) | CH₃ | CF₃ |
| CH₂CH₂CH₂CH₂CClFCBrF₂ | C(S)NH(CH₃) | CH₃ | CF₂CF₃ |
| CH₂CH₂CH₂CH₂CClFCBrF₂ | C(S)NH(CH₃) | CH₃ | CF₂CF₂CF₃ |
| CH₂CH₂CH₂CH₂CClFCBrF₂ | C(S)NH(CH₃) | CH₂CH₃ | CF₃ |
| CH₂CH₂CH₂CH₂CClFCBrF₂ | C(S)NH(CH₃) | CH₂CH₃ | CF₂CF₃ |
| CH₂CH₂CH₂CH₂CClFCBrF₂ | C(S)NH(CH₃) | CH₂CH₃ | CF₂CF₂CF₃ |
| CH₂CH₂CH₂CH₂CClFCBrF₂ | C(S)NH(CH₃) | F | CF₃ |
| CH₂CH₂CH₂CH₂CClFCBrF₂ | C(S)NH(CH₃) | F | CF₂CF₃ |
| CH₂CH₂CH₂CH₂CClFCBrF₂ | C(S)NH(CH₃) | F | CF₂CF₂CF₃ |
| CH₂CH₂CH₂CH₂CClFCBrF₂ | C(S)NH(CH₃) | Cl | CF₃ |
| CH₂CH₂CH₂CH₂CClFCBrF₂ | C(S)NH(CH₃) | Cl | CF₂CF₃ |
| CH₂CH₂CH₂CH₂CClFCBrF₂ | C(S)NH(CH₃) | Cl | CF₂CF₂CF₃ |

TABLE 50

| R¹ | R² | R³ | R⁴ |
|---|---|---|---|
| CH₂CH₂CH₂CH₂CClFCBrF₂ | C(S)N(CH₃)₂ | H | CF₃ |
| CH₂CH₂CH₂CH₂CClFCBrF₂ | C(S)N(CH₃)₂ | H | CF₂CF₃ |
| CH₂CH₂CH₂CH₂CClFCBrF₂ | C(S)N(CH₃)₂ | H | CF₂CF₂CF₃ |
| CH₂CH₂CH₂CH₂CClFCBrF₂ | C(S)N(CH₃)₂ | CH₃ | CF₃ |
| CH₂CH₂CH₂CH₂CClFCBrF₂ | C(S)N(CH₃)₂ | CH₃ | CF₂CF₃ |
| CH₂CH₂CH₂CH₂CClFCBrF₂ | C(S)N(CH₃)₂ | CH₃ | CF₂CF₂CF₃ |
| CH₂CH₂CH₂CH₂CClFCBrF₂ | C(S)N(CH₃)₂ | CH₂CH₃ | CF₃ |
| CH₂CH₂CH₂CH₂CClFCBrF₂ | C(S)N(CH₃)₂ | CH₂CH₃ | CF₂CF₃ |
| CH₂CH₂CH₂CH₂CClFCBrF₂ | C(S)N(CH₃)₂ | CH₂CH₃ | CF₂CF₂CF₃ |
| CH₂CH₂CH₂CH₂CClFCBrF₂ | C(S)N(CH₃)₂ | F | CF₃ |
| CH₂CH₂CH₂CH₂CClFCBrF₂ | C(S)N(CH₃)₂ | F | CF₂CF₃ |
| CH₂CH₂CH₂CH₂CClFCBrF₂ | C(S)N(CH₃)₂ | F | CF₂CF₂CF₃ |
| CH₂CH₂CH₂CH₂CClFCBrF₂ | C(S)N(CH₃)₂ | Cl | CF₃ |
| CH₂CH₂CH₂CH₂CClFCBrF₂ | C(S)N(CH₃)₂ | Cl | CF₂CF₃ |
| CH₂CH₂CH₂CH₂CClFCBrF₂ | C(S)N(CH₃)₂ | Cl | CF₂CF₂CF₃ |

A compound represented by the formula (I-B):

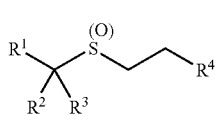

(I-B)

wherein R¹, R², R³ and R⁴ represent combinations shown in the above Table 1 to Table 50.

A compound represented by the formula (I-C):

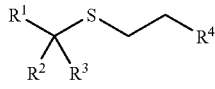

(I-C)

wherein R¹, R², R³ and R⁴ represent combinations shown in the above Table 1 to Table 50.

Next, a production example of an intermediate for producing the compound of the present invention is shown as Reference Production Example.

Reference Production Example 1

To a solution of 10 g of methyl thioglycolate and 21 g of 1-iodo-3,3,3-trifluoropropane in 200 ml of N,N-dimethylformamide, 13 g of potassium carbonate was added under ice-cooling, and then stirred at room temperature for 20 hours. To the reaction mixture, 10% hydrochloric acid was added, followed by extraction with ethyl acetate. The organic layer was washed sequentially with 10% hydrochloric acid and a saturated sodium chloride aqueous solution, dried over anhydrous magnesium sulfate, and then concentrated under reduced pressure. The obtained residue was dissolved in 100 ml of glacial acetic acid, and 50 ml of peracetic acid (32% (w/w) acetic acid solution) was added thereto under ice-cooling. The mixture was stirred at 60° C. for 16 hours. The reaction mixture was allowed to stand near room temperature, poured into water and then extracted with ethyl acetate. The organic layer was washed sequentially with a saturated sodium hydrogen carbonate aqueous solution and a saturated sodium chloride aqueous solution, dried over anhydrous magnesium sulfate, and then concentrated under reduced pressure. The obtained residue was subjected to silica gel chromatography to obtain 14.1 g of methyl (3,3,3-trifluoropropylsulfonyl) acetate. Methyl (3,3,3-trifluoropropylsulfonyl)acetate:

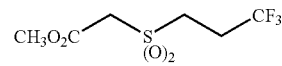

¹H-NMR (CDCl₃, TMS): δ (ppm) 4.05 (s, 2H), 3.84 (s, 3H), 3.49-3.57 (m, 2H), 2.66-2.79 (m, 2H).

Next, Formulation Examples are shown. The term "part(s)" means part(s) by weight.

Formulation Example 1

Nine parts of any one of the present compounds (1) to (6) is dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsion.

Formulation Example 2

Five parts of the present compound (1) and 4 parts of a compound selected from the following group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsion.

The group [A]:

aluminum phosphide, butathiofos, cadusafos, chlorethoxyfos, chlorfenvinphos, chlorpyrifos, chlorpyrifos-methyl, cyanophos (CYAP), diazinon, DCIP (dichlorodiisopropyl ether), dichlofenthion (ECP), dichlorvos (DDVP), dimethoate, dimethylvinphos, disulfoton, EPN, ethion, ethoprophos, etrimfos, fenthion (MPP), fenitrothion (MEP), fosthiazate, formothion, hydrogen phosphide, isofenphos, isoxathion, malathion, mesulfenfos, methidathion (DMTP), monocrotophos, naled (BRP), oxydeprofos (ESP), parathion, phosalone, phosmet (PMP), pirimiphos-methyl, pyridafenthion, quinalphos, phenthoate (PAP), profenofos, propaphos, prothiofos, pyraclorfos, salithion, sulprofos, tebupirimfos, temephos, tetrachlorvinphos, terbufos, thiometon, trichlorphon (DEP), vamidothion, phorate, cadusafos; alanycarb, bendiocarb, benfuracarb, BPMC, carbaryl, carbofuran, carbosulfan, cloethocarb, ethiofencarb, fenobucarb, fenothiocarb, fenoxycarb, furathiocarb, isoprocarb (MIPC), metolcarb, methomyl, methiocarb, NAC, oxamyl, pirimicarb, propoxur (PHC), XMC, thiodicarb, xylylcarb, aldicarb;

acrinathrin, allethrin, benfluthrin, beta-cyfluthrin, bifenthrin, cycloprothrin, cyfluthrin, cyhalothrin, empenthrin, deltamethrin, esfenvalerate, ethofenprox, fenvalerate, flucythrinate, flufenoprox, flumethrin, fluvalinate, halfenprox, imiprothrin, prallethrin, pyrethrins, resmethrin, sigma-cypermethrin, silafluofen, tefluthrin, tralomethrin, transfluthrin, tetramethrin, lambda-cyhalothrin, gamma-cyhalothrin, furamethrin, tau-fluvalinate, 2,3,5,6-tetrafluoro-4-methylbenzyl 2,2-dimethyl-3-(1-propenyl)cyclopropanecarboxylate, 2,3,5,6tetrafluoro-4-(methoxymethyl) benzyl 2,2-dimethyl-3-(2-methyl-1-propenyl)cyclopropanecarboxylate, 2,3,5,6-tetrafluoro-4-(methoxymethyl)benzyl 2,2-dimethyl-3-(2-cyano -1- propenyl)cyclopropanecarboxylate,2,3,5,6-tetrafluoro-4-(methoxymethyl)benzyl 2,2,3,3-tetramethylcyclopropanecarboxylate; cartap, bensultap, thiocyclam, monosultap, bisultap; imidacloprid, nitenpyram, acetamiprid, thiamethoxam, thiacloprid; chlorfluazuron, bistrifluron, diafenthiuron, diflubenzuron, fluazuron, flucycloxuron, flufenoxuron, hexaflumuron, lufenuron, novaluron, noviflumuron, teflubenzuron, triflumuron, triazuron;

acetoprole, fipronil, vaniliprole, pyriprole, pyrafluprole, and the like; chromafenozide, halofenozide, methoxyfenozide, tebufenozide; aldrin, dieldrin, dienochlor, endosulfan, methoxychlor; nicotine sulfate;

aveimectin-B, bromopropylate, buprofezin, chlorphenapyr, cyromazine, D-D (1,3-dichloropropene), emamectin-benzoate, fenazaquin, flupyrazofos, hydroprene, methoprene, indoxacarb, metoxadiazone, milbemycin-A, pymetrozine, pyridalyl, spinosad, sulfluramid, tolfenpyrad, triazamate, flubendiamide, lepimectin, arsenic acid, benclothiaz, calcium cyanamide, calcium polysulfide, chlordane, DDT, DSP, flufenerim, flonicamid, flurimfen, formetanate, metam-ammonium, metam-sodium, methyl bromide, potassium oleate, protrifenbute, spiromesifen, sulfur, metaflumizone, spirotetramat, pyrifluquinazone, chlorantraniliprole, tralopyril, a compound represented by the following formula (A):

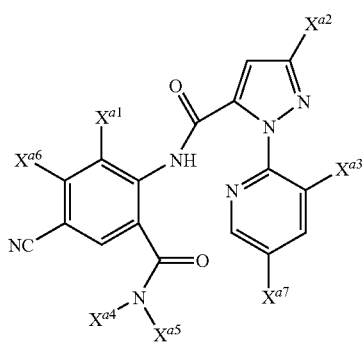

wherein $X^{a1}$ represents methyl, chlorine, bromine or fluorine, $X^{a2}$ represents fluorine, chlorine, bromine, C1-C4 haloalkyl or C1-C4 haloalkoxy, $X^{a3}$ represents fluorine, chlorine or bromine, $X^{a4}$ represents optionally substituted C1-C4 alkyl, optionally substituted C3-C4 alkenyl, optionally substituted C3-C4 alkynyl, optionally substituted C3-05 cycloalkyl or hydrogen, $X^{a5}$ represents hydrogen or methyl, $X^{a6}$ represents hydrogen, fluorine or chlorine, and $X^{a5}$ represents hydrogen, fluorine or chlorine;

a compound represented by the following formula (B):

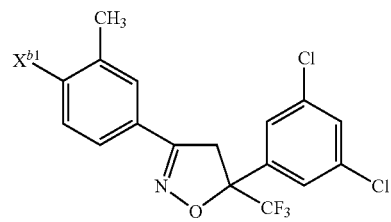

wherein $X^{b1}$ represents $X^{b2}$—NH—C(=O), $X^{b2}$—C(=O)—NH, $X^{b3}$—S(O), optionally substituted pyrrol-1-yl, optionally substituted imidazol-1-yl, optionally substituted pyrazol-1-yl, or optionally substituted 1,2,4-triazol-1-yl, $X^{b2}$ represents optionally substituted C1-C4 haloalkyl such as 2,2,2-trifluoroethyl or optionally substituted C3-C6 cycloalkyl such as cyclopropyl, and $X^{b3}$ represents optionally substituted C1-C4 alkyl such as methyl;

a compound represented by the following formula (C):

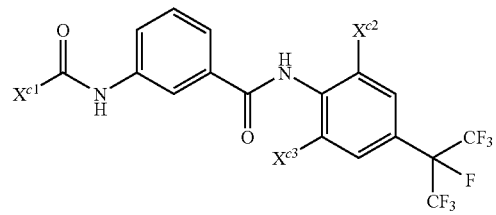

wherein $X^{c1}$ represents optionally substituted C1-C4 alkyl such as 3,3,3-trifluoropropyl, optionally substituted C1-C4 alkoxy such as 2,2,2-trichloroethoxy or optionally substituted phenyl such as phenyl, $X^{c2}$ represents methyl or trifluoromethylthio, and $X^{c3}$ represents methyl or halogen;

acequinocyl, amitraz, benzoximate, bifenazate, bromopropylate, chinomethionat, chlorobenzilate, CPCBS (chlorfenson), clofentezine, cyflumetofen, kelthane (dicofol), fenbutatin oxide, fenothiocarb, fenpyroximate, fluacrypyrim, fluproxyfen, hexythiazox, propargite (BPPS), pyridaben, pyrimidifen, tebufenpyrad, tetradifon, spirodiclofen, spiromesifen, spirotetramat, amidoflumet, and cyenopyrafen.

Formulation Example 3

Five parts of the present compound (2) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsion.

Formulation Example 4

Five parts of the present compound (3) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsion.

Formulation Example 5

Five parts of the present compound (4) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsion.

Formulation Example 6

Five parts of the present compound (5) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsion.

Formulation Example 7

Five parts of the present compound (6) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsion.

Formulation Example 8

Five parts of SORPOL 5060 (registered trade name for TOHO Chemical Industry Co., LTD.) is added to 40 parts of any one of the present compounds (1) to (6) and mixed thoroughly. Then, 32 parts of CARPLEX #80 (registered trade name for Shionogi & Co., Ltd., synthetic anhydrous silicon oxide fine powder) and 23 parts of 300 mesh diatomaceous earth are added thereto and mixed with a juice mixer to obtain a wettable powder.

Formulation Example 9

Three parts of any one of the present compounds (1) to (6), 5 parts of synthetic hydrous silicon oxide fine powder, 5 parts of sodium dodecylbenzenesulfonate, 30 parts of bentonite and 57 parts of clay are mixed by stirring thoroughly. To this mixture an appropriate amount of water is added. The mixture is further stirred, granulated with a granulator, and then air-dried to obtain a granule.

Formulation Example 10

Four point five parts of any one of the present compounds (1) to (6), 1 part of synthetic hydrous silicon oxide fine powder, 1 part of Dorires B (manufactured by Sankyo) as a flocculant, and 7 parts of clay are mixed thoroughly with a mortar and then by stirring with a juice mixer. To the resultant mixture 86.5 parts of cut clay is added and mixed by stirring thoroughly to obtain a powder.

Formulation Example 11

Ten parts of any one of the present compounds (1) to (6), 35 parts of white carbon containing 50 parts of polyoxyethylene alkylether sulfate ammonium salt, and 55 parts of water are mixed and then finely-divided by a wet grinding method to obtain a preparation.

Formulation Example 12

Zero point five part of any one of the present compounds (1) to (6) is dissolved in 10 parts of dichloromethane. This solution is mixed with 89.5 parts of Isopar M (isoparaffin: registered trade name for Exxon Chemical) to obtain an oil.

Formulation Example 13

Zero point one part of any one of the present compounds (1) to (6) and 49.9 parts of NEO-THIOZOL (Chuo Kasei Co., Ltd.) are placed in an aerosol can. An aerosol valve is fitted to the can and the can is then charged with 25 parts of dimethyl ether and 25 parts of LPG. An actuator is fitted to the can to obtain an oily aerosol.

Formulation Example 14

An aerosol container is charged with 0.6 parts of any one of the present compounds (1) to (6), 0.01 part of BHT, 5 parts of xylene, a mixture of 3.39 parts of a deodorized kerosine and 1 part of an emulsifying agent [Atmos 300 (registered trade name for Atmos Chemical Ltd.)] and 50 parts of distilled water. A valve part is attached to the container and the container is then charged with 40 parts of a propellant (LPG) through the valve under increased pressure to obtain an aqueous aerosol.

Formulation Example 15

Five parts of any one of the present compounds (1) to (6) is dissolved in 80 parts of diethylene glycol monoethyl ether. Thereto 15 parts of propylene carbonate is mixed to obtain a spot-on liquid formulation.

Formulation Example 16

Ten parts of any one of the present compounds (1) to (6) is dissolved in 70 parts of diethylene glycol monoethyl ether. Thereto 20 parts of 2-octyldodecanol is mixed to obtain a pour-on liquid formulation.

Formulation Example 17

To 0.5 parts of any one of the present compounds (1) to (6) are added 60 parts of NIKKOL TEALS-42 (a 42% aqueous solution of triethanolamine lauryl sulfate, Nikko Chemicals) and 20 parts of propylene glycol. The mixture is stirred well to obtain a homogeneous solution. Thereto 19.5 parts of water is added and mixed by stirring thoroughly to obtain a homogeneous shampoo formulation.

Formulation Example 18

A porous ceramic plate with a length of 4.0 cm, a width of 0.4 cm and a thickness of 1.2 cm is impregnated with a solution of 0.1 g of any one of the present compounds (1) to (6) in 2 ml of propylene glycol to obtain a heating-type smoking agent.

Formulation Example 19

Five parts of any one of the present compounds (1) to (6) and 95 parts of an ethylene-methyl methacrylate copolymer (the proportion of methyl methacrylate in the copolymer: 10% by weight, ACRYFT WD301, Sumitomo Chemical) are melted and kneaded in a sealed pressure kneader (Moriyama Manufacturing Co., Ltd.). The obtained kneaded product is extruded through a molding die using an extruder to obtain a molded bar with a length of 15 cm and a diameter of 3 mm.

Formulation Example 20

Five parts of any one of the present compounds (1) to (6) and 95 parts of a flexible polyvinyl chloride resin are melted and kneaded in a sealed pressure kneader (Moriyama Manufacturing Co., Ltd.). The obtained kneaded product is extruded through a molding die using an extruder to obtain a molded bar with a length of 15 cm and a diameter of 3 mm.

Next, effectiveness of the compound of the present invention as the active ingredient of a pesticidal composition will be shown by Test Examples.

Test Example 1

Preparations of the present compounds (1), (2), (3), (5) and (6) obtained according to Formulation Example 11 were diluted so that the active ingredient concentration was 55.6 ppm to obtain test solutions.

At the same time, 50 g of culture soil, Bonsol No. 2 (manufactured by Sumitomo Chemical Co., Ltd.) was put into a polyethylene cup with five holes of 5 mm diameter at the bottom, and 10 to 15 seeds of rice were planted therein. The rice plants were grown until the second foliage leaf was developed, and then treated with 45 ml of the test solution by allowing the plants to absorb the test solution from the bottom of the cup. The rice plants were placed in a greenhouse at 25° C. for 6 days and then cut into the same height of 5 cm. Thirty first-instar larvae of *Nilaparvata lugens* were released into the greenhouse at 25° C. and left for 6 days. Then, the number of parasitic *Nilaparvata lugens* on the rice plants was examined.

As a result, on the plants treated with the present compounds (1), (2), (3), (5) and (6), the number of the parasitic pests was 3 or smaller.

Test Example 2

Preparations of the present compounds (2), (3), (5) and (6) obtained according to Formulation Example 11 were diluted so that the active ingredient concentration was 500 ppm to obtain test solutions.

A filter paper having a diameter of 5.5 cm was spread on the bottom of a polyethylene cup having a diameter of 5.5 cm and 0.7 ml of the test solution was added dropwise onto the filter paper. As a bait 30 mg of sucrose was uniformly placed on the filter paper. Into the polyethylene cup, 10 female imagoes of *Musca domestica* were released and the cup was sealed with a lid. After 24 hours, the number of surviving *Musca domestica* was examined and the death rate of the pest was calculated.

As a result, in treatments with the present compounds (2), (3), (5) and (6), the death rate of the pest was 70% or more.

Test Example 3

Preparations of the present compounds (2), (3), (5) and (6) obtained according to Formulation Example 11 were diluted so that the active ingredient concentration was 500 ppm to obtain test solutions.

A filter paper having a diameter of 5.5 cm was spread on the bottom of a polyethylene cup having a diameter of 5.5 cm and 0.7 ml of the test solution was added dropwise onto the filter paper. As a bait 30 mg of sucrose was uniformly placed on the filter paper. Into the polyethylene cup, 2 male imagoes of *Blattella germanica* were released and the cup was sealed with a lid. After 6 days, the number of surviving *Blattella germanica* was examined and the death rate of the pest was calculated.

As a result, in treatments with the present compounds (2), (3), (5) and (6), the death rate of the pest was 100%.

Test Example 4

Preparations of the present compounds (1), (2), (3), (4), (5) and (6) obtained according to Formulation Example 11 were diluted so that the active ingredient concentration was 500 ppm to obtain test solutions.

To 100 mL of ion-exchanged water, 0.7 ml of the test solution was added (active ingredient concentration: 3.5 ppm). Into the solution, 20 last-instar larvae of *Culex pipiens pallens* were released. After one day, the number of surviving *Culex pipiens pallens* was examined and the death rate of the pest was calculated.

As a result, in treatments with the present compounds (1), (2), (3), (4), (5) and (6), the death rate of the pest was 90% or more.

INDUSTRIAL APPLICABILITY

The compound of the present invention is useful as an active ingredient of a pesticidal composition.

The invention claimed is:

1. An organic sulfur compound represented by the formula (I):

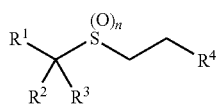

wherein $R^1$ represents a C3-C6 alkyl group substituted with at least one fluorine atom and at least one atom selected from the group consisting of a chlorine atom, a bromine atom and an iodine atom, $R^2$ represents $C(=Q)N(R^6)_2$, $R^3$ represents a hydrogen atom, a halogen atom or a C1-C4 alkyl group, $R^4$ represents a C1-C5 fluoroalkyl group, Q represents an oxygen atom or a sulfur atom, $R^5$ represents a C1-C4 alkyl group, $R^6$'s each independently represent a hydrogen atom or a C1-C4 alkyl group, or two $R^6$'s are bonded to each other at their terminals to form a C2-C7 alkylene group, and n represents 0, 1 or 2.

2. The organic sulfur compound according to claim 1, wherein n is 2.

3. The organic sulfur compound according to claim 1 or 2, wherein Q is an oxygen atom.

4. The organic sulfur compound according to claim 1 or 2, wherein $R^2$ is a cyano group.

5. The organic sulfur compound according to claim 1 or 2, wherein $R^2$ is $C(=Q)N(R^6)_2$, and $R^6$'s are each independently a hydrogen atom or a C1-C4 alkyl group.

6. The organic sulfur compound according to claim 1 or 2, wherein $R^2$ is $C(=Q)N(R^6)_2$, and $R^6$ is a hydrogen atom.

7. The organic sulfur compound according to claim 1, wherein $R^3$ is a halogen atom.

8. A pesticidal composition comprising the organic sulfur compound according to claim 1 as an active ingredient.

9. A method for controlling harmful arthropods comprising applying an effective amount of the organic sulfur compound according to claim 1 to harmful arthropods or a place where harmful arthropods inhabit.

* * * * *